(12) United States Patent
Nonni et al.

(10) Patent No.: US 9,511,167 B2
(45) Date of Patent: *Dec. 6, 2016

(54) MODIFIED CELLULOSE FROM CHEMICAL KRAFT FIBER AND METHODS OF MAKING AND USING THE SAME

(71) Applicant: GP Cellulose GMbH, Zug (CH)

(72) Inventors: Arthur J. Nonni, Peachtree City, GA (US); Charles E. Courchene, Snellville, GA (US); Christopher Michael Slone, Atlanta, GA (US); Peter R. Abitz, Decatur, GA (US); Darold Tippey, Atlanta, GA (US)

(73) Assignee: GP Cellulose GmbH, Zug (CH)

( * ) Notice: Subject to any disclaimer, the term of this patent is extended or adjusted under 35 U.S.C. 154(b) by 53 days.

This patent is subject to a terminal disclaimer.

(21) Appl. No.: 13/840,915

(22) Filed: Mar. 15, 2013

(65) Prior Publication Data

US 2013/0204218 A1    Aug. 8, 2013

Related U.S. Application Data

(63) Continuation-in-part of application No. 13/322,419, filed as application No. PCT/US2010/036763 on May 28, 2010, now Pat. No. 8,778,136.

(60) Provisional application No. 61/182,000, filed on May 28, 2009.

(51) Int. Cl.
*A61L 15/20* (2006.01)
*A61L 15/28* (2006.01)
*A61L 15/48* (2006.01)

(52) U.S. Cl.
CPC ........... *A61L 15/20* (2013.01); *A61L 15/28* (2013.01); *A61L 15/48* (2013.01)

(58) Field of Classification Search
CPC .......... D21C 9/163; D21H 11/04; D21H 11/20
See application file for complete search history.

(56) References Cited

U.S. PATENT DOCUMENTS

| | | |
|---|---|---|
| 1,298,552 A | 3/1919 | Ornstein |
| 1,298,553 A | 3/1919 | Ornstein |
| 1,298,554 A | 3/1919 | Ornstein |
| 1,860,431 A | 5/1932 | Richter |
| 2,112,116 A | 3/1938 | Richter |
| 2,178,696 A | 11/1939 | Muskat et al. |
| 2,212,338 A | 8/1940 | Bown |
| 2,368,527 A | 1/1945 | Edelstein |
| 2,512,338 A | 6/1950 | Klug et al. |
| 2,749,336 A | 6/1956 | Boddicker et al. |
| 2,975,169 A | 3/1961 | Cranford et al. |
| 2,978,446 A | 4/1961 | Battista et al. |
| 3,251,731 A | 5/1966 | Gard et al. |
| 3,308,012 A | 3/1967 | Tobar |
| 3,313,641 A | 4/1967 | Borchert |
| 3,707,148 A | 12/1972 | Bryce |
| 3,728,213 A | 4/1973 | Hinz |
| 3,728,331 A | 4/1973 | Savage |
| 3,868,955 A | 3/1975 | Steiger et al. |
| 3,975,206 A | 8/1976 | Lotzgesell et al. |
| 4,022,965 A | 5/1977 | Goheen et al. |
| 4,100,094 A | 7/1978 | Burns et al. |
| 4,222,819 A | 9/1980 | Fossum et al. |
| 4,270,976 A | 6/1981 | Sandstrom et al. |
| 4,372,314 A | 2/1983 | Wall |
| 4,410,397 A | 10/1983 | Kempf |
| 4,427,490 A | 1/1984 | Eckert |
| 4,444,621 A | 4/1984 | Lindahl |
| 4,454,005 A | 6/1984 | Stofko et al. |
| 4,470,212 A | 9/1984 | Stafford et al. |
| 4,599,138 A | 7/1986 | Lindahl |
| 4,614,646 A | 9/1986 | Christiansen |
| 4,619,663 A | 10/1986 | Tatin |
| 4,661,205 A | 4/1987 | Ow et al. |
| H479 H | 6/1988 | Wood et al. |
| 4,756,799 A | 7/1988 | Bengtsson et al. |
| 4,783,239 A | 11/1988 | Rich |
| 4,838,944 A | 6/1989 | Kruger |

(Continued)

FOREIGN PATENT DOCUMENTS

| | | |
|---|---|---|
| AU | B53648/90 | 7/1992 |
| CA | 1129161 | 8/1982 |

(Continued)

OTHER PUBLICATIONS

International Paper, https://web.archive.org/web/20051107013141/http://www.internationalpaper.com/Paper/Paper%20Products/Pulp/Southern_Bleached_So.html, Nov. 7, 2005.*
Achwal, W.B. et al., Viscosity Measurements on Chemically Modified Celluloses; I&EC Product Research and Development, vol. 6, No. 4 (Dec. 1967), pp. 278-281.
Ahgren, L., The Action of Fenton's Reagent on Dextran, Die Starke 27, Jahrg. 1975, No. 4, pp. 121-123.
Andrews, D.H., et al., The Bleaching of Pulp, TAPPI Press, Third Ed. (1979), pp. 211-220.
Argyropoulos, D., et al., Nitrogen-Centered Activators of Peroxide-Reinforced Oxygen Delignification, Ind. Eng. Chem. Res., American Chemical Society, Feb. 4, 2004, pp. 1200-1205.
Birtwell, C., et al., The Chemical Analysis of Cotton-Oxycellulose, Part I, Journal of the Textile Institute Transactions (1925); 16:1; T13-T52.
Blattner, R., et al., Effects of Iron, Copper, and Chromate Ions on the Oxidative Degradation of Cellulose Model Compounds, Carbohydrate Research, vol. 138 (1985); pp. 73-82.

(Continued)

*Primary Examiner* — Michael H Wilson
*Assistant Examiner* — Eric Yaary
(74) *Attorney, Agent, or Firm* — Ram W. Sabnis

(57) ABSTRACT

A modified kraft pulp fiber with unique properties is provided. The modified fiber can be a modified bleached kraft fiber that is almost indistinguishable from its conventional counterpart, except that it has a low degree of polymerization (DP). Methods for making the modified fiber and products made from it are also provided. The method can be a one step acidic, iron catalyzed peroxide treatment process that can be incorporated into a single stage of a multi-stage bleaching process. The products can be chemical cellulose feedstocks, microcrystalline cellulose feedstocks, fluff pulps and products made from them.

23 Claims, 2 Drawing Sheets

(56) References Cited

U.S. PATENT DOCUMENTS

| | | |
|---|---|---|
| 4,869,783 A | 9/1989 | Prusas et al. |
| 4,875,974 A | 10/1989 | Rich |
| 4,889,595 A | 12/1989 | Herron et al. |
| 5,002,635 A | 3/1991 | Gentile, Jr. et al. |
| 5,015,245 A | 5/1991 | Noda |
| 5,026,589 A | 6/1991 | Schechtman |
| 5,087,324 A | 2/1992 | Awofeso et al. |
| 5,284,703 A | 2/1994 | Everhart et al. |
| 5,296,099 A | 3/1994 | Griggs et al. |
| 5,300,358 A | 4/1994 | Evers |
| 5,302,248 A | 4/1994 | Weinstock et al. |
| H1340 H | 7/1994 | Yetter et al. |
| 5,346,589 A | 9/1994 | Braunstein et al. |
| 5,383,964 A | 1/1995 | Suc et al. |
| 5,447,602 A | 9/1995 | Sajbel et al. |
| 5,460,924 A | 10/1995 | Buchanan et al. |
| 5,480,984 A | 1/1996 | Angerer et al. |
| 5,522,967 A | 6/1996 | Shet |
| 5,529,662 A | 6/1996 | Tan et al. |
| 5,536,625 A | 7/1996 | Buchanan et al. |
| 5,552,019 A | 9/1996 | Weinstock et al. |
| 5,558,658 A | 9/1996 | Menard et al. |
| 5,562,645 A | 10/1996 | Tanzer et al. |
| 5,580,485 A | 12/1996 | Feringa et al. |
| 5,593,543 A | 1/1997 | Balos et al. |
| 5,607,546 A | 3/1997 | Hoglund et al. |
| 5,630,906 A | 5/1997 | Boe et al. |
| 5,639,348 A | 6/1997 | Payton et al. |
| 5,698,688 A | 12/1997 | Smith et al. |
| 5,703,225 A | 12/1997 | Shet et al. |
| 5,708,618 A | 1/1998 | Toda et al. |
| 5,766,159 A | 6/1998 | Martin et al. |
| 5,853,428 A | 12/1998 | Collins et al. |
| 5,863,389 A | 1/1999 | White et al. |
| 5,876,625 A | 3/1999 | Collins et al. |
| 5,994,531 A | 11/1999 | Doenges et al. |
| 6,010,594 A | 1/2000 | Henricson et al. |
| 6,063,982 A | 5/2000 | Martin et al. |
| 6,099,586 A | 8/2000 | Collins et al. |
| 6,100,441 A | 8/2000 | Blomstrom et al. |
| 6,136,223 A | 10/2000 | Collins et al. |
| 6,146,494 A | 11/2000 | Seger et al. |
| 6,165,318 A | 12/2000 | Paren et al. |
| 6,210,801 B1 | 4/2001 | Luo et al. |
| 6,214,164 B1 | 4/2001 | Rantala |
| 6,214,976 B1 | 4/2001 | Watanabe et al. |
| 6,221,487 B1 | 4/2001 | Luo et al. |
| 6,228,126 B1 | 5/2001 | Cimecioglu et al. |
| 6,235,392 B1 | 5/2001 | Luo et al. |
| 6,241,779 B1 | 6/2001 | Collins et al. |
| 6,258,207 B1 | 7/2001 | Pan |
| 6,302,997 B1 | 10/2001 | Hurter et al. |
| 6,306,253 B2 | 10/2001 | Henricson |
| 6,306,334 B1 | 10/2001 | Luo et al. |
| 6,319,361 B1 | 11/2001 | Smith et al. |
| 6,331,354 B1 | 12/2001 | Sealey, II et al. |
| 6,368,456 B1 | 4/2002 | Cimecioglu et al. |
| 6,379,494 B1 | 4/2002 | Jewell et al. |
| 6,398,908 B1 | 6/2002 | Hermansson et al. |
| 6,399,854 B1 | 6/2002 | Vartiainen |
| 6,432,266 B1 | 8/2002 | Fukushima et al. |
| 6,436,238 B1 | 8/2002 | Pitkanen et al. |
| 6,440,523 B1 | 8/2002 | Sealey, II et al. |
| 6,440,547 B1 | 8/2002 | Luo et al. |
| 6,444,314 B1 | 9/2002 | Luo et al. |
| 6,458,245 B1 | 10/2002 | Hoglund et al. |
| 6,471,727 B2 | 10/2002 | Luo et al. |
| 6,491,788 B2 | 12/2002 | Sealey, II et al. |
| 6,511,930 B1 | 1/2003 | Luo et al. |
| 6,514,380 B1 | 2/2003 | Laine et al. |
| 6,514,613 B2 | 2/2003 | Luo et al. |
| 6,515,049 B1 | 2/2003 | Doenges et al. |
| 6,518,419 B1 | 2/2003 | Van Der Lugt et al. |
| 6,524,348 B1 | 2/2003 | Jewell et al. |
| 6,528,163 B2 | 3/2003 | Sealey, II et al. |
| 6,540,876 B1 | 4/2003 | Cimecioglu et al. |
| 6,541,627 B1 | 4/2003 | Ono et al. |
| 6,562,195 B2 | 5/2003 | Cimecioglu et al. |
| 6,582,559 B2 | 6/2003 | Thornton et al. |
| 6,586,588 B1 | 7/2003 | Cimecioglu et al. |
| 6,596,033 B1 | 7/2003 | Luo et al. |
| 6,605,181 B1 | 8/2003 | Bergqvist et al. |
| 6,605,350 B1 | 8/2003 | Sealey, II et al. |
| 6,627,749 B1 | 9/2003 | Kumar |
| 6,632,328 B2 | 10/2003 | Wan et al. |
| 6,635,755 B1 | 10/2003 | Jaschinski et al. |
| 6,685,856 B2 | 2/2004 | Sealey, II et al. |
| 6,686,039 B2 | 2/2004 | Sealey, II et al. |
| 6,686,040 B2 | 2/2004 | Sealey, II et al. |
| 6,686,464 B1 | 2/2004 | Harding et al. |
| 6,689,378 B1 | 2/2004 | Sun et al. |
| 6,692,827 B2 | 2/2004 | Luo et al. |
| 6,695,950 B1 | 2/2004 | Cimecioglu et al. |
| 6,699,358 B1 | 3/2004 | Evans et al. |
| 6,706,237 B2 | 3/2004 | Luo et al. |
| 6,706,876 B2 | 3/2004 | Luo et al. |
| 6,716,976 B1 | 4/2004 | Jetten et al. |
| 6,743,332 B2 | 6/2004 | Haynes et al. |
| 6,765,042 B1 | 7/2004 | Thornton et al. |
| 6,770,168 B1 | 8/2004 | Stigsson |
| 6,770,576 B2 | 8/2004 | Cook et al. |
| 6,770,755 B1 | 8/2004 | Gunnars et al. |
| 6,773,552 B1 | 8/2004 | Albert et al. |
| 6,773,648 B2 | 8/2004 | Luo et al. |
| 6,793,686 B2 | 9/2004 | Cimecioglu et al. |
| 6,797,113 B2 | 9/2004 | Sealey, II et al. |
| 6,821,383 B2 | 11/2004 | Shore et al. |
| 6,824,645 B2 | 11/2004 | Jaschinski et al. |
| 6,849,156 B2 | 2/2005 | Besemer et al. |
| 6,852,904 B2 | 2/2005 | Sun et al. |
| 6,861,023 B2 | 3/2005 | Sealey, II et al. |
| 6,872,821 B2 | 3/2005 | Cimecioglu et al. |
| 6,881,299 B2 | 4/2005 | Parrish et al. |
| 6,896,725 B2 | 5/2005 | Thornton et al. |
| 6,916,402 B2 | 7/2005 | Shannon et al. |
| 6,916,466 B2 | 7/2005 | Besemer et al. |
| 6,923,889 B2 | 8/2005 | Huuskonen et al. |
| 6,924,369 B2 | 8/2005 | Doenges et al. |
| 6,936,710 B2 | 8/2005 | Bragt et al. |
| 6,939,961 B1 | 9/2005 | Schlesiger |
| 6,958,108 B1 | 10/2005 | Vuorinen |
| 6,987,181 B2 | 1/2006 | Jaschinski et al. |
| 7,001,483 B2 | 2/2006 | Severeid et al. |
| 7,019,191 B2 | 3/2006 | Looney et al. |
| 7,022,837 B2 | 4/2006 | Harding et al. |
| 7,067,444 B2 | 6/2006 | Luo et al. |
| 7,083,704 B2 | 8/2006 | Sealey, II et al. |
| 7,090,744 B2 | 8/2006 | Sealey, II et al. |
| 7,094,317 B2 | 8/2006 | Lundberg et al. |
| 7,161,005 B2 | 1/2007 | Schlingloff et al. |
| 7,247,722 B2 | 7/2007 | Cimecioglu et al. |
| 7,252,837 B2 | 8/2007 | Guo et al. |
| 7,279,071 B2 | 10/2007 | Williams et al. |
| 7,279,177 B2 | 10/2007 | Looney et al. |
| 7,326,317 B2 | 2/2008 | Westermark et al. |
| 7,390,566 B2 | 6/2008 | Luo et al. |
| 7,411,110 B2 | 8/2008 | Sawyer et al. |
| 7,455,902 B2 | 11/2008 | Weerawarna et al. |
| 7,456,285 B2 | 11/2008 | Schlingloff et al. |
| 7,520,958 B2 | 4/2009 | Tan et al. |
| 7,541,396 B2 | 6/2009 | Luo et al. |
| 7,589,051 B2 | 9/2009 | Erazo-Majewicz et al. |
| 7,608,167 B2 | 10/2009 | Luo et al. |
| 7,692,004 B2 | 4/2010 | Schlingloff et al. |
| 7,700,764 B2 | 4/2010 | Heijnesson-Hulten |
| 7,708,214 B2 | 5/2010 | Medoff |
| 7,727,945 B2 | 6/2010 | Rodrigues et al. |
| 7,867,358 B2 | 1/2011 | Medoff |
| 7,867,359 B2 | 1/2011 | Medoff |
| 7,939,101 B2 | 5/2011 | Obae et al. |
| 7,947,292 B2 | 5/2011 | Besemer et al. |
| 7,955,536 B2 | 6/2011 | Sawyer et al. |
| 7,971,809 B2 | 7/2011 | Medoff |
| 7,976,676 B2 | 7/2011 | Yin et al. |

(56) References Cited

U.S. PATENT DOCUMENTS

| | | |
|---|---|---|
| 8,007,635 B2 | 8/2011 | Tan et al. |
| 8,029,896 B2 | 10/2011 | Kumamoto et al. |
| 8,044,013 B2 | 10/2011 | Schlingloff et al. |
| 8,057,636 B2 | 11/2011 | Vinson et al. |
| 8,084,391 B2 | 12/2011 | Weerawarna |
| 8,282,774 B2 | 10/2012 | Tan et al. |
| 8,372,765 B2 | 2/2013 | Braig et al. |
| 8,497,410 B2 | 7/2013 | Leithem et al. |
| 2001/0025695 A1 | 10/2001 | Patt et al. |
| 2001/0028955 A1 | 10/2001 | Luo et al. |
| 2001/0050153 A1 | 12/2001 | Wajer et al. |
| 2002/0005262 A1 | 1/2002 | Cimecioglu et al. |
| 2002/0034638 A1 | 3/2002 | Sealey, II et al. |
| 2002/0098317 A1 | 7/2002 | Jaschinski et al. |
| 2002/0134521 A1 | 9/2002 | Shannon et al. |
| 2002/0144796 A1 | 10/2002 | Wan et al. |
| 2002/0165110 A1 | 11/2002 | Reinhardt et al. |
| 2003/0019596 A1 | 1/2003 | Ragauskas et al. |
| 2003/0024661 A1 | 2/2003 | Shore et al. |
| 2003/0026828 A1 | 2/2003 | Besemer et al. |
| 2003/0084983 A1 | 5/2003 | Rangachari et al. |
| 2003/0208175 A1 | 11/2003 | Gross et al. |
| 2004/0024375 A1* | 2/2004 | Litvay .................. 604/378 |
| 2004/0101546 A1 | 5/2004 | Gorman et al. |
| 2004/0118533 A1 | 6/2004 | Shannon et al. |
| 2004/0154761 A1 | 8/2004 | Duggirala et al. |
| 2004/0154765 A1 | 8/2004 | Huuskonen et al. |
| 2004/0166144 A1 | 8/2004 | Besemer et al. |
| 2004/0260082 A1 | 12/2004 | Van der Wilden et al. |
| 2004/0265371 A1 | 12/2004 | Looney et al. |
| 2005/0000628 A1* | 1/2005 | Norrby ............ A61F 13/15593 156/177 |
| 2005/0028956 A1 | 2/2005 | Winslow |
| 2005/0051288 A1 | 3/2005 | Yin |
| 2005/0061455 A1 | 3/2005 | Tan et al. |
| 2005/0084412 A1 | 4/2005 | MacDonald et al. |
| 2006/0004335 A1 | 1/2006 | Wang et al. |
| 2006/0065377 A1 | 3/2006 | Luo |
| 2006/0070711 A1 | 4/2006 | Luo |
| 2006/0144535 A1 | 7/2006 | Nguyen et al. |
| 2006/0159733 A1 | 7/2006 | Pendharkar et al. |
| 2006/0260773 A1* | 11/2006 | Tan et al. .................. 162/70 |
| 2007/0000627 A1 | 1/2007 | Tan et al. |
| 2007/0051481 A1* | 3/2007 | Tan .................. D21C 1/02 162/17 |
| 2007/0119556 A1 | 5/2007 | Tan et al. |
| 2007/0125507 A1 | 6/2007 | Walter et al. |
| 2007/0143932 A1 | 6/2007 | Buchert et al. |
| 2007/0163735 A1 | 7/2007 | Buchert et al. |
| 2007/0190110 A1 | 8/2007 | Pameijer et al. |
| 2007/0199668 A1 | 8/2007 | Scarpello et al. |
| 2007/0272377 A1 | 11/2007 | Mei et al. |
| 2008/0188636 A1 | 8/2008 | Argyropoulos et al. |
| 2008/0294132 A1 | 11/2008 | Tan et al. |
| 2008/0308239 A1 | 12/2008 | Hart et al. |
| 2009/0044345 A1 | 2/2009 | Schlingloff et al. |
| 2009/0054863 A1 | 2/2009 | Tan et al. |
| 2009/0165968 A1 | 7/2009 | Tan et al. |
| 2009/0312537 A1 | 12/2009 | Medoff |
| 2010/0055437 A1 | 3/2010 | Fink et al. |
| 2010/0124583 A1 | 5/2010 | Medoff |
| 2010/0206501 A1 | 8/2010 | Medoff |
| 2010/0233481 A1 | 9/2010 | Isogai et al. |
| 2010/0282422 A1 | 11/2010 | Miyawaki et al. |
| 2010/0316863 A1 | 12/2010 | Kumamoto et al. |
| 2010/0320156 A1 | 12/2010 | Olaiya et al. |
| 2011/0139383 A1 | 6/2011 | Medoff |
| 2011/0287275 A1 | 11/2011 | Tan et al. |
| 2012/0004194 A1 | 1/2012 | Lu et al. |
| 2012/0175073 A1 | 7/2012 | Nonni et al. |
| 2013/0066291 A1 | 3/2013 | Tan et al. |

FOREIGN PATENT DOCUMENTS

| | | |
|---|---|---|
| CA | 1190360 | 7/1985 |
| CA | 2469922 | 6/2004 |
| DE | 19620241 | 11/1997 |
| DE | 10123665 | 11/2002 |
| EP | 0091412 | 10/1983 |
| EP | 0172135 | 2/1986 |
| EP | 0480469 | 4/1992 |
| EP | 0716182 | 6/1996 |
| EP | 0647158 | 8/1997 |
| EP | 0845966 | 3/2000 |
| EP | 0999222 | 5/2000 |
| EP | 1077282 | 2/2001 |
| EP | 1077285 | 2/2001 |
| EP | 1106732 | 6/2001 |
| EP | 1154074 | 11/2001 |
| EP | 1156065 | 11/2001 |
| EP | 1093467 | 3/2002 |
| EP | 0889997 | 7/2002 |
| EP | 0923635 | 2/2003 |
| EP | 1300420 | 4/2003 |
| EP | 0787231 | 5/2003 |
| EP | 1424085 | 6/2003 |
| EP | 1228099 | 9/2003 |
| EP | 1025305 | 11/2003 |
| EP | 1068376 | 11/2003 |
| EP | 0511695 | 6/2004 |
| EP | 1430911 | 6/2004 |
| EP | 1155039 | 7/2004 |
| EP | 0863158 | 11/2004 |
| EP | 1077286 | 2/2005 |
| EP | 1541590 | 6/2005 |
| EP | 1278913 | 11/2005 |
| EP | 1155040 | 4/2006 |
| EP | 1383857 | 5/2006 |
| EP | 1245722 | 6/2006 |
| EP | 1230456 | 7/2006 |
| EP | 1676863 | 7/2006 |
| EP | 1311717 | 8/2006 |
| EP | 1137672 | 12/2006 |
| EP | 1743906 | 1/2007 |
| EP | 1668180 | 8/2007 |
| EP | 1862587 | 12/2007 |
| EP | 2084325 | 4/2010 |
| EP | 2216345 | 8/2010 |
| EP | 2226414 | 9/2010 |
| EP | 2236665 | 10/2010 |
| EP | 1694711 | 12/2010 |
| EP | 1583567 | 3/2012 |
| FR | 2688787 | 9/1993 |
| GB | 555985 | 9/1943 |
| JP | 58054089 | 3/1983 |
| JP | 2001-115389 | 4/2001 |
| JP | 2003-026701 | 1/2003 |
| JP | 2003-096681 | 4/2003 |
| RU | 2268327 | 5/2005 |
| WO | WO 92/14760 | 9/1992 |
| WO | WO 94/21690 | 9/1994 |
| WO | WO 95/06157 | 3/1995 |
| WO | WO 95/26438 | 10/1995 |
| WO | WO 95/34628 | 12/1995 |
| WO | WO 95/35406 | 12/1995 |
| WO | WO 95/35408 | 12/1995 |
| WO | WO 96/09434 | 3/1996 |
| WO | WO 96/20667 | 7/1996 |
| WO | WO 96/38111 | 12/1996 |
| WO | WO 97/22749 | 6/1997 |
| WO | WO 97/30208 | 8/1997 |
| WO | WO 98/03626 | 1/1998 |
| WO | WO 98/56981 | 12/1998 |
| WO | WO 99/09244 | 2/1999 |
| WO | WO 99/47733 | 9/1999 |
| WO | WO 99/57158 | 11/1999 |
| WO | WO 99/57370 | 11/1999 |
| WO | WO 00/26257 | 5/2000 |
| WO | WO 00/32245 | 6/2000 |
| WO | WO 00/47812 | 8/2000 |
| WO | WO 00/50462 | 8/2000 |

(56) References Cited

FOREIGN PATENT DOCUMENTS

| | | |
|---|---|---|
| WO | WO 00/50463 | 8/2000 |
| WO | WO 00/65145 | 11/2000 |
| WO | WO 01/29309 | 4/2001 |
| WO | WO 01/34656 | 5/2001 |
| WO | WO 01/34657 | 5/2001 |
| WO | WO 01/83887 | 11/2001 |
| WO | WO 01/88236 | 11/2001 |
| WO | WO 02/48196 | 6/2002 |
| WO | WO 02/48197 | 6/2002 |
| WO | WO 02/49565 | 6/2002 |
| WO | WO 02/086206 | 10/2002 |
| WO | WO 02/088289 | 11/2002 |
| WO | WO 02/095129 | 11/2002 |
| WO | WO 03/006739 | 1/2003 |
| WO | WO 03/042451 | 5/2003 |
| WO | WO 03/051410 | 6/2003 |
| WO | WO 08/051410 | 6/2003 |
| WO | WO 2004/062703 | 7/2004 |
| WO | WO 2005/028744 | 3/2005 |
| WO | WO 2005/058972 | 6/2005 |
| WO | WO 2005/068074 | 7/2005 |
| WO | WO 2006/102543 | 9/2006 |
| WO | WO 2006/119392 | 11/2006 |
| WO | WO 2006/125517 | 11/2006 |
| WO | WO 2006/127880 | 11/2006 |
| WO | WO 2007/042192 | 4/2007 |
| WO | WO 2007/090461 | 8/2007 |
| WO | WO 2008/010187 | 1/2008 |
| WO | WO 2008/098037 | 8/2008 |
| WO | WO 2008/153565 | 12/2008 |
| WO | WO 2008/154073 | 12/2008 |
| WO | WO 2009/134746 | 11/2009 |
| WO | WO 2010/025224 | 3/2010 |
| WO | WO 2011/002956 | 1/2011 |
| WO | WO 2011/088889 | 7/2011 |
| WO | WO 2011/089123 | 7/2011 |
| WO | WO 2011/090425 | 7/2011 |
| WO | WO 2010/138941 | 12/2012 |
| WO | WO 2013/000074 | 1/2013 |

OTHER PUBLICATIONS

Bradg, P.L., et al., TEMPCO-mediated oxidation of polysaccharides: survey of methods and applications, Topics in Catalysis, vol. 27, Nos. 1-4, Feb. 2004, pp. 49-66.
Burgess, "Relationships Between Colour Production in Cellulose and the Chemical Changes Brought About by Bleaching," Transcript of a Lecture given at the Meeting of the Book and Paper Specialty Group, AIC Annual Meeting, Milwaukee, May 27-30, 1982 (http://cool.conversation-us.org/coolaic/sg/bpg/annual/v01/bp01-05.html).
Calvini, P., et al., Viscometric determination of a dialdehyde content in periodate oxycellulose, Part I, Methodology; Cellulose, vol. 11 (2004), pp. 99-107.
Carboxyl Content of Pulp, T237 cm-98; TAPPI (1998), pp. 1-3.
Chandra, S., et al., Kinetics of Carbohydrates and Lignin Degradation and Formation of Carbonyl and Carboxyl Groups in Low Consistency Ozonation of Softwood Pulps, International Pulp Bleaching Conference (1985), pp. 28-35.
Copper Number of Pulp, Paper, and Paperboad, T430 cm-98, TAPPI (1999), pp. 1-4.
De Belder, A.N., et al., The Oxidation of Glycosides, ACTA Chemical Scandinavica 17 (1963), pp. 1012-1014.
Dang et al., "Alkaline peroxide treatment of ECF bleached softwood kraft pulps. Part 1. Characterizing the effect of alkaline peroxide treatment on carboxyl groups of fibers," Holzforschung, vol. 61, pp. 445-450, 2007.
Dang, "The Investigation of Carboxyl Groups of Pulp Fibers During Kraft Pulping, Alkaline Peroxide Bleaching, and TEMPO-mediated Oxication," Georgia Insitute of Technology, Aug. 2007.
Easty et al., "Estimation of Pulp Yield in Continuous Digesters from Carbohydrate and Lignin Determinations," TAPPI Journal 65(12):78-80 (1982).
Edwards et al., "Research and Development of Active Cotton Wound Dressings," 2004 Beltwide Cotton Conferences, San Antonio TX.
Ellefsen, O., Viscosity Measurements on Chemically Modified Cellulose, Journal of Polymer Science: Part C, No. 2 (1963), pp. 321-330.
Emery, J., et al., Iron-Catalyzed Oxidation of Wood Carbohydrates, Wood Science and Technology, vol. 8 (1974), pp. 127-137.
English-Language Abstract of JP 2003-096681, published Apr. 3, 2003.
Fellers, C., et al., Ageing/Degradation of Paper, Report No. 1E, FoU-projecktet for papperskonservering, Stockholm, Sep. 1989, pp. 1-137.
Fibersource.com, "Cellulose," [retrieved Sep. 12, 2013 from http://www.fibersource.com/F-tutor/cellulose-htm], 5 pages.
Filho et al., "Hydrogen Peroxide in Chemical Pulp Bleaching an overview," 2002 Congreso Iberoamericana de investigacion en cellulose y papel, CIADICYP pp. 1-27.
Georgia-Pacific West, Permit Renewal Response to Comments 2001.
Gierer, J., Formation and Involvement of Superoxide (Ow-HO2) and Hydroxyl (OH) Radicals in TCF Bleaching Processes: A Review, Department of Pulp and Paper Chemistry and Technology, The Royal Institute of Technology; Stockholm, Holzforschung, vol. 51, No. 1(1997); pp. 34-46.
Gilbert, B., et al., The Oxidation of Some Polysaccharides by the Hydroxyl Radical: An E.S.R. Investigation, Carbohydrate Research, vol. 125 (1984); pp. 217-235.
Godsay, M.P., et al., Physico-Chemical Properties of Ozone Oxidized Kraft Pulps, TAPPI, 1984 Oxygen Delignification Symposium, pp. 55-69.
Grant, J. Wood Pulp, A New Series of Plant Books, vol. II, Chronica Botanica Company, 1938; pp. 158-169.
Gullichsen, "Chemical Pulping," Papermaking Science and Technology, Book 6A, pp. A635-A665, 1992.
Halliwell, G., Catalytic Decomposition of Cellulose Under Biological Conditions; Biochem. J. (1965), vol. 95, pp. 35-40.
International Preliminary Report on Patentability dated Nov. 29, 2011, issued in priority PCT Application No. PCT/US2010/036763.
International Search Report dated Apr. 7, 2011, in International No. PCT/US2010/03673.
Isogai, A., et al., Preparation of polyuronic acid from cellulose by TEMPO-mediated oxidation, Cellulose (1998), vol. 5, pp. 153-164.
Ivanov, V.I., et al., Chemical changes produces in the cellulose macromolecule by oxidizing agents, Bulletin of the Academy of Sciences of the USSR, Mar.-Apr. 1953, vol. 2, Issue 2, pp. 341-350.
Kennedy et al., The Chemistry and Processing of Wood and Plant Fibrous Materials, p. 155, Woodhead Publishing Ltd, Abington Hall, Abington, Cambridge CBI 6AH, England (1996).
Keshk, S., Homogenous reactions of cellulose from different natural sources, Carbohydrate Polymers, vol. 74, (2008), pp. 942-945.
Kirk, T.K., et al., Characteristics of Cotton Cellulose Depolymerized by a Brown-Rot Fungus, by Acid, or by Chemical Oxidants, Holzforschung, vol. 45, No. 4 (1991), pp. 239-244.
Kishimoto, T., et al., No-Chlorine Bleaching of Kraft Pulp, Holzforschung, vol. 52 (1998), pp. 180-184.
Koenigs, J., Hydrogen Peroxide and Iron: A Proposed system for Decomposition of Wood by Brown-Rot Basidiomycetes, Journal of Society of Wood and Technology, vol. 6, No. 1, Spring 1974, pp. 66-80.
Kubelka et al., "Delignification with Acidic Hydrogen Peroxide Activated by Molybdate," Journal of Pulp and Paper Science: vol. 18, No. 3, May 1992, pp. J108-J114.
Launer, H.F., et al., Failure of Alkaline Methods to Measure Degree of Polymerization of Carbohydrates, Analytical Chemistry, vol. 33, No. 1, Jan. 1961, pp. 79-83.
Lenntech, B.V., http://www.lentech.com/Fenton-reaction.htm [downloaded from www.archive.org], Jun. 28, 2003 [retrieved Sep. 12, 2013], whole document.
Luc Lapierre et al., "The Effect of Magnesium Ions and Chelants on Peroxide Bleaching," Holzforschung, vol. 57, No. 6, pp. 627-633, 2003.

(56) References Cited

OTHER PUBLICATIONS

Moody, G.J., The Action of Hydrogen Peroxide on Carbohydrates and Related Compounds, Advances in Carbohydrate Chemistry, Academic Press, vol. 19 (1964), pp. 149-179.
Morton, J.H., The Chemistry and Processing of Wood and Plant Fibrous Materials, Woodhead Publishing Ltd. (1996), pp. 151-158.
Mussatto, S., et al., Hydrogen peroxide bleaching of cellulose pulps obtained from brewer's spent grain, Cellulose (2008), vol. 15, pp. 641-649.
Nevell, T.P., Effect of Manganese (II), Cobalt (II), and Copper (I) Hydroxides on the Kinetics of the Oxidation of Cellulose by Hypochlorite; Textile Research Journal (1985), pp. 270-280.
Perng, Y., et al., The effect of metal complexes in the electrochemically mediated oxygen bleaching of wood pulp, TAPPI Journal (1993) vol. 76, No. 10, pp. 139-147.
Qian et al., Journal of Wood Chemistry and Technology (2002), vol. 22, No. 4, pp. 267-284.
Qian, "The Chemical Mechanism of a Brown-Rot Decay Mimtic System and its Applicationi n paper Recycling Processes," [Chapter 4: The Effects of Chelator Mediated Fenton System on the Fiber and Paper Properties of Hardwood Kraft Pulp], 2001, *Electronic Theses and Dissertations*, Paper 505.
Ragauskas, Copper Number—Carbonyl Content of Pulp Fibers (document "date created" May 12, 2007) Retrieved from http://rbi.gatech.edu/faculty/ragauskas_art/technical_reviews/Copper%20Number.pdf.
Rahmawat et al., "Pulp bleaching by hydrogen peroxide activated with copper 2,2_-dipyridylamine and 4-aminopyridine complexes," 2005, Chemical Engineering Journal, vol. 112, pp. 167-171.
Rapson, W.H., et al., Carbonyl Groups in Cellulose and Colour Reversion, Pulp and Paper Magazine of Canada, Jul. 1957, pp. 151-157.
Rapson, W.H., The Role of pH in Bleaching Pulp, TAPPI, vol. 39, No. 5, May 1956, pp. 284-294.
Rohrling et al., "A novel method for the determination of carbonyl groups in cellulosics by fluorescence labeling. 2. Validation and applications," Biomacromolecules Sep.-Oct. 2002; 3(5): 969-975.
Ruuttunen et al., "Concomitant Usage of Transition Metal Polyanions as Catalysts in Oxygen Delignification: Laboratory Bleaching Trials," 2006, Appita Jornal, p. 1-14.
Saito, T., et al., Cellulose Nanofibers Prepared by TEMPO-Mediated Oxidation of Native Cellulose, Biomacromolecules (2007), vol. 8, pp. 2485-2491.
Shenai, "Studies in Chemically Modified Celluloses. IX. Oxidation of Cellulose in the Presence of Chelating Agents," 1976, Journal of Applied Polymer Science, vol. 20, pp. 385-391.
Sihtola, H., et al., Comparison and Conversion of Viscosity and DP-Values Determined by Different Methods, Paper and Timber, vol. 45, No. 1 (1963), pp. 225-232.
Smook, Handbook for Pulp and Paper Technologists, 1992, Angus Wilde Publications, $2^{nd}$ edition, Chapter 16, pp. 228-263.
Smook, Handbook for Pulp Paper Technologists, 1992, Angus Wilde Publications, $2^{nd}$ Edition, Chapter 13, pp. 194-208.
Smook, Handbook of Pulp and Paper Terminology, 1990, pp. 89-90.
Song et al., Novel antiviral activity of dialdehyde starch, Electronic J. Biotech., vol. 12, No. 2, 2009.
Suchy et al., "Catalysis and Activation of Oxygen and Peroxide Delignification of Chemical Pulps; A Review," Miscellaneous Report, Pulp and Paper Research Institute of Canada, 1999, pp. 1-32.
Sun et al., "The effect of metal ions on the reaction of hydrogen peroxide with Kraft lignin model compounds," 1999, Can. J. Chem., vol. 77, pp. 667-675.
Tanaka, N., et al., Effect of Oxalic Acid on the Oxidative Breakdown of Cellulose by the Fenton Reaction, Kyoto University, 1994), pp. 8-10.
Viscosity of pulp (capillary viscometer method), T230 om-99, TAPPI (1999), pp. 1-9.
Walker, C., Selectivity of Iron-Based Catalysts in a Polymeric Model System for Biomimetic Bleaching, The Institute of Paper Science and Technology, Sep. 1994, p. 196.
Whitmore, P.M., et al., Determination of the Cellulose Scission Route in the Hydrolytic and Oxcidative Degradation of Paper, Restaurator, vol. 15 (1994), pp. 26-45.
Wojciak et al., "Direct Characterization of Hydrogen Peroxide Bleached Thermomechanial Pulp Using Spectroscopic Methods," J. Phys. Chem. A., vol. 111, pp. 10530-10536, 2007.
Zeronian et al., "Bleaching of cellulose by hydrogen peroxide," Cellulose, 1995, pp. 265-272.
Office Action in co-pending U.S. Appl. No. 13/322,419 dated May 22, 2013.
Office Action in co-pending U.S. Appl. No. 13/322,419 dated Oct. 22, 2012.
Office Action in co-pending U.S. Appl. No. 13/322,419 dated Nov. 22, 2013.
Office Action in co-pending U.S. Appl. No. 13/314,493 dated Jan. 23, 2015.
Office Action in co-pending U.S. Appl. No. 13/314,493 dated Mar. 13, 2013.
Office Action in co-pending U.S. Appl. No. 13/314,493 dated Jun. 4, 2014.
Office Action in co-pending U.S. Appl. No. 13/314,493 dated Aug. 24, 2012.
Office Action in co-pending U.S. Appl. No. 13/619,504 dated Jan. 26, 2015.
Office Action in co-pending U.S. Appl. No. 13/619,504 dated Sep. 10, 2014.
Office Action in co-pending U.S. Appl. No. 13/800,941 dated Jan. 2, 2015.
Office Action in co-pending U.S. Appl. No. 13/828,705 dated Jan. 2, 2015.
Office Action in co-pending U.S. Appl. No. 13/840,857 dated Jan. 14, 2015.
Office Action in co-pending U.S. Appl. No. 13/619,504 dated Jul. 30, 2015.
Office Action in co-pending U.S. Appl. No. 13/800,941 dated Aug. 12, 2015.
Office Action in co-pending U.S. Appl. No. 13/828,705 dated Aug. 13, 2015.
Office Action in co-pending U.S. Appl. No. 13/840,857 dated Aug. 12, 2015.
Examiner's Answer to Appeal Brief in co-pending U.S. Appl. No. 13/314,493 dated Jan. 4, 2016.
Office Action in co-pending U.S. Appl. No. 13/619,504 dated Feb. 2, 2016.
Office Action in co-pending U.S. Appl. No. 13/800,941 dated Feb. 19, 2016.
Office Action in co-pending U.S. Appl. No. 13/828,705 dated Feb. 25, 2016.
Office Action in co-pending U.S. Appl. No. 13/840,857 dated Feb. 10, 2016.
ESM 055B01 "Aldehyde and Carboxyl Content of Pulp" Method Summary.

\* cited by examiner

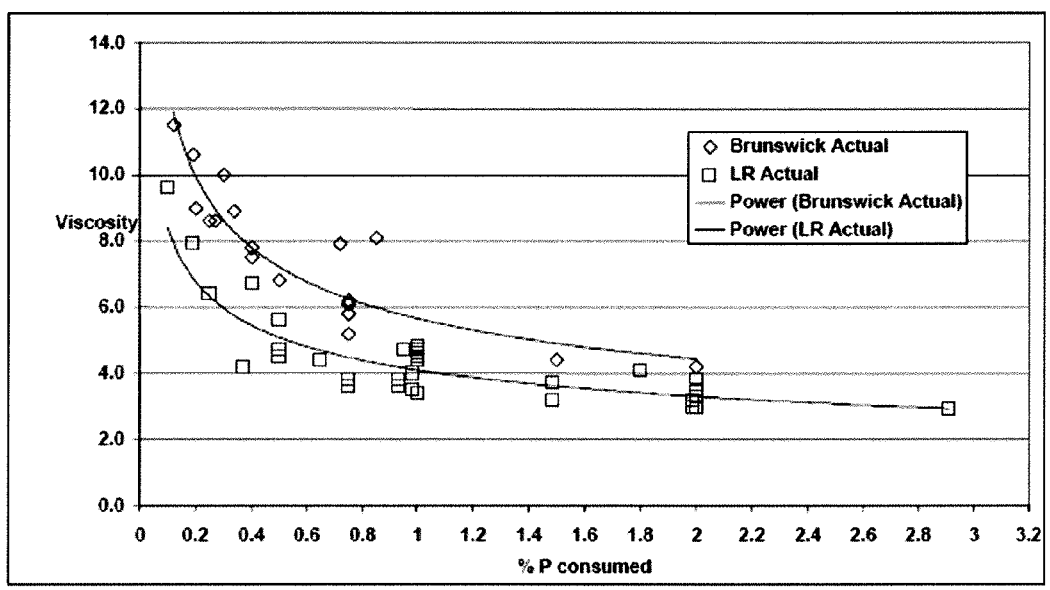
Figure 1. Final 0.5% Capillary CED viscosity as a function of % peroxide (based on pulp) consumed.

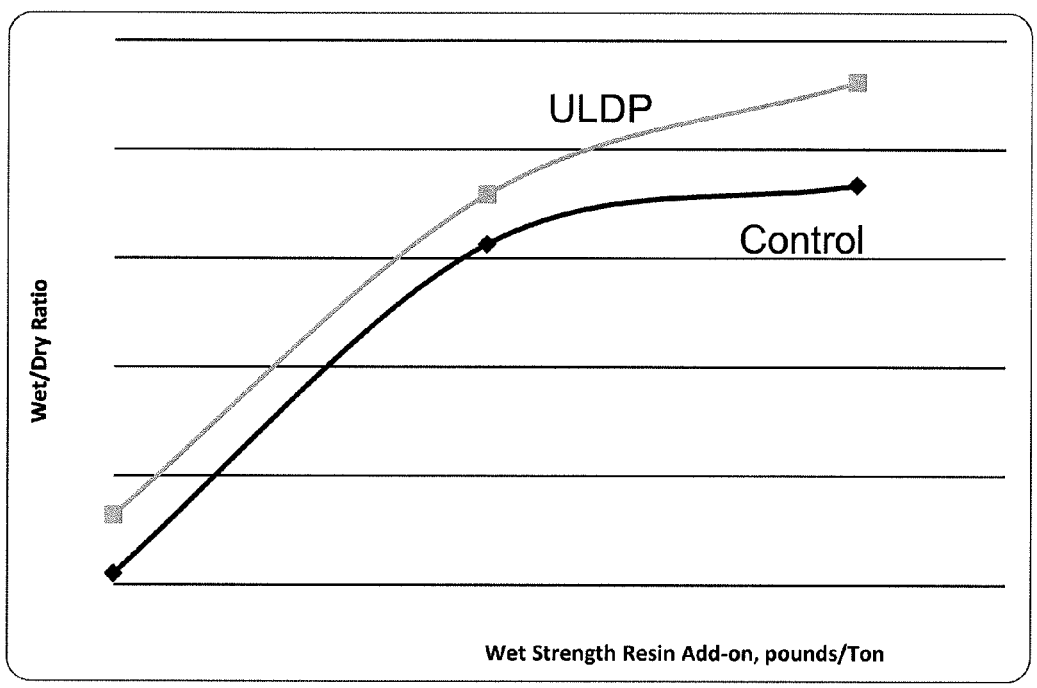
Figure 2. Wet/Dry strength ratio given as a function of wet strength resin level.

MODIFIED CELLULOSE FROM CHEMICAL KRAFT FIBER AND METHODS OF MAKING AND USING THE SAME

This application is a continuation-in-part of U.S. application Ser. No. 13/322,419, filed Nov. 23, 2011, which is a national stage entry under 35 U.S.C. §371 from PCT International Application No. PCT/US2010/036763, filed May 28, 2010, and claims priority to and the benefit of the filing date of U.S. Provisional Application No. 61/182,000, filed May 28, 2009, the subject matter of all of which is incorporated herein by reference.

TECHNICAL FIELD

This disclosure relates to the chemical modification of cellulose fiber. More particularly, this disclosure relates to chemically modified cellulose fiber derived from bleached kraft pulp that exhibits a unique set of characteristics, improving its performance over standard cellulose fiber derived from kraft pulp and making it useful in applications that have heretofore been limited to expensive fibers (e.g., cotton or high alpha content sulfite pulp). Specifically, the chemically modified bleached kraft fiber may exhibit one or more of the following beneficial characteristics, including but not limited to, improved odor control, improved compressibility, and/or improved brightness. The chemically modified bleached kraft fiber may exhibit one or more of these beneficial characteristics while also maintaining one or more other characteristics of the non-chemically modified bleached kraft fiber, for example, maintaining fiber length and/or freeness.

This disclosure further relates to chemically modified cellulose fiber derived from bleached softwood and/or hardwood kraft pulp that exhibits a low or ultra low degree of polymerization, making it suitable for use as fluff pulp in absorbent products, as a chemical cellulose feedstock in the production of cellulose derivatives including cellulose ethers and esters, and in consumer products. As used herein "degree of polymerization" may be abbreviated "DP." This disclosure still further relates to cellulose derived from a chemically modified kraft fiber having a level-off degree of polymerization of less than about 80. More specifically, the chemically modified kraft fiber described herein, exhibiting a low or ultra low degree of polymerization (herein referred to as "LDP" or "ULDP"), can be treated by acid or alkaline hydrolysis to further reduce the degree of polymerization to less than about 80, for instance to less than about 50, to make it suitable for a variety of downstream applications.

This disclosure also relates to methods for producing the improved fiber described. This disclosure provides, in part, a method for simultaneously increasing the carboxylic and aldehydic functionality of kraft fibers. The fiber, described, is subjected to a catalytic oxidation treatment. In some embodiments, the fiber is oxidized with iron or copper and then further bleached to provide a fiber with beneficial brightness characteristics, for example brightness comparable to standard bleached fiber. Further, at least one process is disclosed that can provide the improved beneficial characteristics mentioned above, without the introduction of costly added steps for post-treatment of the bleached fiber. In this less costly embodiment, the fiber can be treated in a single stage of a kraft process, such as a kraft bleaching process. Still a further embodiment relates to a five-stage bleaching process comprising a sequence of $D_0E1$ $D1E2D2$, where stage four (E2) comprises the catalytic oxidation treatment.

Finally, this disclosure relates to consumer products, cellulose derivatives (including cellulose ethers and esters), and microcrystalline cellulose all produced using the chemically modified cellulose fiber as described.

BACKGROUND

Cellulose fiber and derivatives are widely used in paper, absorbent products, food or food-related applications, pharmaceuticals, and in industrial applications. The main sources of cellulose fiber are wood pulp and cotton. The cellulose source and the cellulose processing conditions generally dictate the cellulose fiber characteristics, and therefore, the fiber's applicability for certain end uses. A need exists for cellulose fiber that is relatively inexpensive to process, yet is highly versatile, enabling its use in a variety of applications.

Cellulose exists generally as a polymer chain comprising hundreds to tens of thousands of glucose units. Various methods of oxidizing cellulose are known. In cellulose oxidation, hydroxyl groups of the glycosides of the cellulose chains can be converted, for example, to carbonyl groups such as aldehyde groups or carboxylic acid groups. Depending on the oxidation method and conditions used, the type, degree, and location of the carbonyl modifications may vary. It is known that, certain oxidation conditions may degrade the cellulose chains themselves, for example by cleaving the glycosidic rings in the cellulose chain, resulting in depolymerization. In most instances, depolymerized cellulose not only has a reduced viscosity, but also has a shorter fiber length than the starting cellulosic material. When cellulose is degraded, such as by depolymerizing and/or significantly reducing the fiber length and/or the fiber strength, it may be difficult to process and/or may be unsuitable for many downstream applications. A need remains for methods of modifying cellulose fiber that may improve both carboxylic acid and aldehyde functionalities, which methods do not extensively degrade the cellulose fiber. This disclosure provides unique methods that resolve one or more of these deficiencies.

Various attempts have been made to oxidize cellulose to provide both carboxylic and aldehydic functionality to the cellulose chain without degrading the cellulose fiber. In traditional cellulose oxidation methods, it may be difficult to control or limit the degradation of the cellulose when aldehyde groups are present on the cellulose. Previous attempts at resolving these issues have included the use of multi-step oxidation processes, for instance site-specifically modifying certain carbonyl groups in one step and oxidizing other hydroxyl groups in another step, and/or providing mediating agents and/or protecting agents, all of which may impart extra cost and by-products to a cellulose oxidation process. Thus, there exists a need for methods of modifying cellulose that are cost effective and/or can be performed in a single step of a process, such as a kraft process.

This disclosure provides novel methods that offer vast improvements over methods attempted in the prior art. Generally, oxidization of cellulose kraft fibers, in the prior art, is conducted after the bleaching process. Surprisingly, the inventors have discovered that it is possible to use the existing stages of a bleaching sequence, particularly the fourth stage of a five stage bleaching sequence, for oxidation of cellulose fibers. Furthermore, surprisingly, the inventors have discovered that a metal catalyst, particularly an iron catalyst, could be used in the bleaching sequence to accomplish this oxidation without interfering with the final product, for example, because the catalyst did not remain bound in the cellulose resulting in easier removal of at least some of the residual iron prior to the end of the bleaching sequence than would have been expected based upon the knowledge in the art. Moreover, unexpectedly, the inventors have discovered that such methods could be conducted without substantially degrading the fibers.

It is known in the art that cellulose fiber, including kraft pulp, may be oxidized with metals and peroxides and/or peracids. For instance, cellulose may be oxidized with iron and peroxide ("Fenton's reagent"). See Kishimoto et al., Holzforschung, vol. 52, no. 2 (1998), pp. 180-184. Metals and peroxides, such as Fenton's reagent, are relatively inexpensive oxidizing agents, making them somewhat desirable for large scale applications, such as kraft processes. In the case of Fenton's reagent, it is known that this oxidation method can degrade cellulose under acidic conditions. Thus, it would not have been expected that Fenton's reagent could be used in a kraft process without extensive degradation of the fibers, for example with an accompanying loss in fiber length, at acidic conditions. To prevent degradation of cellulose, Fenton's reagent is often used under alkaline conditions, where the Fenton reaction is drastically inhibited. However, additional drawbacks may exist to using Fenton's reagent under alkaline conditions. For example, the cellulose may nonetheless be degraded or discolored. In kraft pulp processing, the cellulose fiber is often bleached in multi-stage sequences, which traditionally comprise strongly acidic and strongly alkaline bleaching steps, including at least one alkaline step at or near the end of the bleaching sequence. Therefore, contrary to what was known in the art, it was quite surprising that fiber oxidized with iron in an acidic stage of a kraft bleaching process could result in fiber with enhanced chemical properties, but without physical degradation or discoloration.

Thus there is a need for a low cost and/or single step oxidation that could impart both aldehyde and carboxylic functionalities to a cellulose fiber, such as a fiber derived from kraft pulp, without extensively degrading the cellulose and/or rendering the cellulose unsuitable for many downstream applications. Moreover, there remains a need for imparting high levels of carbonyl groups, such as carboxylic acid, ketone, and aldehyde groups, to cellulose fiber. For example, it would be desirable to use an oxidant under conditions that do not inhibit the oxidation reaction, unlike the use of Fenton's reagent at alkaline pH for instance, to impart high levels of carbonyl groups. The present inventors have overcome many difficulties of the prior art, providing methods that meet these needs.

In addition to the difficulties in controlling the chemical structure of cellulose oxidation products, and the degradation of those products, it is known that the method of oxidation may affect other properties, including chemical and physical properties and/or impurities in the final products. For instance, the method of oxidation may affect the degree of crystallinity, the hemi-cellulose content, the color, and/or the levels of impurities in the final product. Ultimately, the method of oxidation may impact the ability to process the cellulose product for industrial or other applications.

Bleaching of wood pulp is generally conducted with the aim of selectively increasing the whiteness or brightness of the pulp, typically by removing lignin and other impurities, without negatively affecting physical properties. Bleaching of chemical pulps, such as kraft pulps, generally requires several different bleaching stages to achieve a desired brightness with good selectivity. Typically, a bleaching sequence employs stages conducted at alternating pH ranges. This alternation aids in the removal of impurities generated in the bleaching sequence, for example, by solubilizing the products of lignin breakdown. Thus, in general, it is expected that using a series of acidic stages in a bleaching sequence, such as three acidic stages in sequence, would not provide the same brightness as alternating acidic/alkaline stages, such as acidic-alkaline-acidic. For instance, a typical DEDED sequence produces a brighter product than a DEDAD sequence (where A refers to an acid treatment). Accordingly, a sequence that does not have an intervening alkaline stage, yet produces a product with comparable brightness, would not be expected by a person of skill in the art.

Generally, while it is known that certain bleaching sequences may have advantages over others in a kraft process, the reasons behind any advantages are less well understood. With respect to oxidation, no studies have shown any preference for oxidation in a particular stage of a multi-stage sequence or any recognition that fiber properties can be affected by post oxidation stages/treatments. For instance, the prior art does not disclose any preference for a later stage oxidation over an earlier stage oxidation. In some embodiments, the disclosure provides methods uniquely performed in particular stages (e.g., later stages of a bleaching process) that have benefits in the kraft process and that result in fibers having a unique set of physical and chemical characteristics.

In addition, with respect to brightness in a kraft bleaching process, it is known that metals, in particular transition metals naturally present in the pulp starting material, are detrimental to the brightness of the product. Thus, bleaching sequences frequently aim to remove certain transition metals from a final product to achieve a target brightness. For example, chelants may be employed to remove naturally occurring metal from a pulp. Thus, because there is emphasis on removing the metals naturally present in the pulp, a person of skill in the art would generally not add any metals to a bleaching sequence as that would compound the difficulties in achieving a brighter product.

With respect to iron, moreover, addition of this material to a pulp leads to significant discoloration, akin to the discoloration present when, for example, burning paper. This discoloration, like the discoloration of burnt paper, has heretofore been believed to be non-reversible. Thus, it has been expected that upon discoloring a wood pulp with added iron, the pulp would suffer a permanent loss in brightness that could not be recovered with additional bleaching.

Thus, while is known that iron or copper and peroxide can inexpensively oxidize cellulose, heretofore they have not been employed in pulp bleaching processes in a manner that achieves a comparable brightness to a standard sequence not employing an iron or copper oxidation step. Generally, their use in pulp bleaching processes has been avoided. Surprisingly, the inventors have overcome these difficulties, and in some embodiments, provide a novel method of inexpensively oxidizing cellulose with iron or copper in a pulp bleaching processes. In some embodiments, the methods disclosed herein result in products that have characteristics that are very surprising and contrary to those predicted based on the teachings of the prior art. Thus, the methods of the disclosure may provide products that are superior to the products of the prior art and can be more cost-effectively produced.

For instance, it is generally understood in the art that metals, such as iron, bind well to cellulose and cannot be removed by normal washing. Typically, removing iron from cellulose is difficult and costly, and requires additional processing steps. The presence of high levels of residual iron in a cellulose product is known to have several drawbacks, particularly in pulp and papermaking applications. For instance, iron may lead to discoloration of the final product and/or may be unsuitable for applications in which the final product is in contact with the skin, such as in diapers and wound dressings. Thus, the use of iron in a kraft bleaching process would be expected to suffer from a number of drawbacks.

Heretofore, oxidation treatment of kraft fiber to improve functionality has often been limited to oxidation treatment after the fiber was bleached. Moreover, known processes for rendering a fiber more aldehydic also cause a concomitant loss in fiber brightness or quality. Furthermore, known processes that result in enhanced aldehydic functionality of the fiber also result in a loss of carboxylic functionality. The methods of this disclosure do not suffer from one or more of those drawbacks.

Kraft fiber, produced by a chemical kraft pulping method, provides an inexpensive source of cellulose fiber that generally maintains its fiber length through pulping, and generally provides final products with good brightness and strength characteristics. As such, it is widely used in paper applications. However, standard kraft fiber has limited applicability in downstream applications, such as cellulose derivative production, due to the chemical structure of the cellulose resulting from standard kraft pulping and bleaching. In general, standard kraft fiber contains too much residual hemi-cellulose and other naturally occurring materials that may interfere with the subsequent physical and/or chemical modification of the fiber. Moreover, standard kraft fiber has limited chemical functionality, and is generally rigid and not highly compressible.

The rigid and coarse nature of kraft fiber can require the layering or addition of different types of materials, such as cotton, in applications that require contact with human skin, for example, diapers, hygiene products, and tissue products. Accordingly, it may be desirable to provide a cellulose fiber with better flexibility and/or softness to reduce the requirement of using other materials, for example, in a multilayered product.

Cellulose fiber in applications that involve absorption of bodily waste and/or fluids, for example, diapers, adult incontinence products, wound dressings, sanitary napkins, and/or tampons, is often exposed to ammonia present in bodily waste and/or ammonia generated by bacteria associated with bodily waste and/or fluids. It may be desirable in such applications to use a cellulose fiber which not only provides bulk and absorbency, but which also has odor reducing and/or antibacterial properties, e.g., can reduce odor from nitrogenous compounds, such as ammonia ($NH_3$). Heretofore, modification of kraft fiber by oxidation to improve its odor control capability invariably came with an undesirable decrease in brightness. A need exists for an inexpensive modified kraft fiber that exhibits good absorbency characteristics and/or odor control capabilities while maintaining good brightness characteristics.

In today's market, consumers desire absorbent products, for example, diapers, adult incontinence products, and sanitary napkins, that are thinner. Ultra-thin product designs require lower fiber weight and can suffer from a loss of product integrity if the fiber used is too short. Chemical modification of kraft fiber can result in loss of fiber length making it unacceptable for use in certain types of products, e.g., ultra-thin products. More specifically, kraft fiber treated to improve aldehyde functionality, which is associated with improved odor control, may suffer from a loss of fiber length during chemical modification making it unsuitable for use in ultra-thin product designs. A need exists for an inexpensive fiber that exhibits compressibility without a loss in fiber length which makes it uniquely suited to ultra-thin designs (i.e., the product maintains good absorbency based upon the amount of fiber that can be compressed into a smaller space while maintaining product integrity at lower fiber weights).

Traditionally, cellulose sources that were useful in the production of absorbent products or tissue were not also useful in the production of downstream cellulose derivatives, such as cellulose ethers and cellulose esters. The production of low viscosity cellulose derivatives from high viscosity cellulose raw materials, such as standard kraft fiber, required additional manufacturing steps that would add significant cost while imparting unwanted by-products and reducing the overall quality of the cellulose derivative. Cotton linter and high alpha cellulose content sulfite pulps, which generally have a high degree of polymerization, are generally used in the manufacture of cellulose derivatives such as cellulose ethers and esters. However, production of cotton linters and sulfite fiber with a high degree of polymerization and/or viscosity is expensive due to the cost of the starting material, in the case of cotton; the high energy, chemical, and environmental costs of pulping and bleaching, in the case of sulfite pulps; and the extensive purifying processes required, which applies in both cases. In addition to the high cost, there is a dwindling supply of sulfite pulps available to the market. Therefore, these fibers are very expensive, and have limited applicability in pulp and paper applications, for example, where higher DP or higher viscosity pulps may be required. For cellulose derivative manufacturers these pulps constitute a significant portion of their overall manufacturing cost. Thus, there exists a need for low cost fibers, such as a modified kraft fiber, that may be used in the production of cellulose derivatives.

There is also a need for inexpensive cellulose materials that can be used in the manufacture of microcrystalline cellulose. Microcrystalline cellulose is widely used in food, pharmaceutical, cosmetic, and industrial applications, and is a purified crystalline form of partially depolymerized cellulose. The use of kraft fiber in microcrystalline cellulose production, without the addition of extensive post-bleaching processing steps, has heretofore been limited. Microcrystalline cellulose production generally requires a highly purified cellulosic starting material, which is acid hydrolyzed to remove amorphous segments of the cellulose chain. See U.S. Pat. No. 2,978,446 to Battista et al. and U.S. Pat. No. 5,346,589 to Braunstein et al. A low degree of polymerization of the chains upon removal of the amorphous segments of cellulose, termed the "level-off DP," is frequently a starting point for microcrystalline cellulose production and its numerical value depends primarily on the source and the processing of the cellulose fibers. The dissolution of the non-crystalline segments from standard kraft fiber generally degrades the fiber to an extent that renders it unsuitable for most applications because of at least one of 1) remaining impurities; 2) a lack of sufficiently long crystalline segments; or 3) it results in a cellulose fiber having too high a degree of polymerization, typically in the range of 200 to 400, to make it useful in the production of microcrystalline cellulose. Kraft fiber having good purity and/or a lower level-off DP value, for example, would be desirable, as the draft fiber may provide greater versatility in microcrystalline cellulose production and applications.

In the present disclosure, fiber having one or more of the described properties can be produced simply through modification of a typical kraft pulping plus bleaching process.

Fiber of the present disclosure overcomes many of the limitations associated with known modified kraft fiber discussed above.

BRIEF DESCRIPTION OF THE DRAWINGS

FIG. 1 shows a chart of final 0.5% capillary CED viscosity as a function of percent peroxide consumed.

FIG. 2 shows a chart of wet strength to dry strength ratio given as a function of wet strength resin level.

DESCRIPTION

I. Methods

The present disclosure provides novel methods for treating cellulose fiber. In some embodiments, the disclosure provides a method of modifying cellulose fiber, comprising providing cellulose fiber, and oxidizing the cellulose fiber. As used herein, "oxidized," "catalytically oxidized," "catalytic oxidation" and "oxidation" are all understood to be interchangeable and refer to treatment of cellulose fiber with at least a catalytic amount of at least one of iron or copper and at least one peroxide, such as hydrogen peroxide, such that at least some of the hydroxyl groups of the cellulose fibers are oxidized. The phrase "iron or copper" and similarly "iron (or copper)" mean "iron or copper or a combination thereof." In some embodiments, the oxidation comprises simultaneously increasing carboxylic acid and aldehyde content of the cellulose fiber.

The cellulose fiber used in the methods described herein may be derived from softwood fiber, hardwood fiber, and mixtures thereof. In some embodiments, the modified cellulose fiber is derived from softwood, such as southern pine. In some embodiments, the modified cellulose fiber is derived from hardwood, such as eucalyptus. In some embodiments, the modified cellulose fiber is derived from a mixture of softwood and hardwood. In yet another embodiment, the modified cellulose fiber is derived from cellulose fiber that has previously been subjected to all or part of a kraft process, i.e., kraft fiber.

References in this disclosure to "cellulose fiber" or "kraft fiber" are interchangeable except where specifically indicated as different or as one of ordinary skill in the art would understand them to be different.

In at least one embodiment, the method comprises providing cellulose fiber, and oxidizing the cellulose fiber while generally maintaining the fiber length of the cellulose fibers "Fiber length" and "average fiber length" are used interchangeably when used to describe the property of a fiber and mean the length-weighted average fiber length. Therefore, for example, a fiber having an average fiber length of 2 mm should be understood to mean a fiber having a length-weighted average fiber length of 2 mm.

In at least one embodiment, the method comprises providing cellulose fiber, partially bleaching the cellulose fiber, and oxidizing the cellulose fiber. In some embodiments, the oxidation is conducted in the bleaching process. In some embodiments, the oxidation is conducted after the bleaching process.

In at least one embodiment, the method comprises providing the cellulose fiber, and oxidizing cellulose fiber thereby reducing the degree of polymerization of the cellulose fiber.

In at least one embodiment, the method comprises providing cellulose fiber, and oxidizing the cellulose fiber while maintaining the Canadian Standard Freeness ("freeness") of that cellulose fiber.

In at least one embodiment, the method comprises providing cellulose fiber, oxidizing the cellulose fiber, and increasing the brightness of that oxidized cellulose fiber over standard cellulose fiber.

As discussed above, in accordance with the disclosure, oxidation of cellulose fiber involves treating the cellulose fiber with at least a catalytic amount of iron or copper and hydrogen peroxide. In at least one embodiment, the method comprises oxidizing cellulose fiber with iron and hydrogen peroxide. The source of iron can be any suitable source, as a person of skill would recognize, such as for example ferrous sulfate (for example ferrous sulfate heptahydrate), ferrous chloride, ferrous ammonium sulfate, ferric chloride, ferric ammonium sulfate, or ferric ammonium citrate.

In some embodiments, the method comprises oxidizing the cellulose fiber with copper and hydrogen peroxide. Similarly, the source of copper can be any suitable source as a person of skill would recognize. Finally, in some embodiments, the method comprises oxidizing the cellulose fiber with a combination of copper and iron and hydrogen peroxide.

In some embodiments, the disclosure provides a method for treating cellulose fiber, comprising, providing cellulose fiber, pulping the cellulose fiber, bleaching the cellulose fiber, and oxidizing the cellulose fiber.

In some embodiments, the method further comprises oxygen delignifying the cellulose fiber. Oxygen delignification can be performed by any method known to those of ordinary skill in the art. For instance, oxygen delignification may be a conventional two-stage oxygen delignification. It is known, for example, that oxygen delignifying cellulose fiber, such as kraft fiber, may alter the carboxylic acid and/or aldehyde content of the cellulose fiber during processing. In some embodiments, the method comprises oxygen delignifying the cellulose fiber before bleaching the cellulose fiber.

In at least one embodiment, the method comprises oxidizing cellulose fiber in at least one of a kraft pulping step, an oxygen delignification step, and a kraft bleaching step. In a preferred embodiment, the method comprises oxidizing the cellulose fiber in at least one kraft bleaching step. In at least one embodiment, the method comprises oxidizing the cellulose fiber in two or more than one kraft bleaching steps.

When cellulose fiber is oxidized in a bleaching step, cellulose fiber should not be subjected to substantially alkaline conditions in the bleaching process during or after the oxidation. In some embodiments, the method comprises oxidizing cellulose fiber at an acidic pH. In some embodiments, the method comprises providing cellulose fiber, acidifying the cellulose fiber, and then oxidizing the cellulose fiber at acidic pH. In some embodiments, the pH ranges from about 2 to about 6, for example from about 2 to about 5 or from about 2 to about 4.

The pH can be adjusted using any suitable acid, as a person of skill would recognize, for example, sulfuric acid or hydrochloric acid or filtrate from an acidic bleach stage of a bleaching process, such as a chlorine dioxide (D) stage of a multi-stage bleaching process. For example, the cellulose fiber may be acidified by adding an extraneous acid. Examples of extraneous acids are known in the art and include, but are not limited to, sulfuric acid, hydrochloric acid, and carbonic acid. In some embodiments, the cellulose fiber is acidified with acidic filtrate, such as waste filtrate, from a bleaching step. In some embodiments, the acidic filtrate from a bleaching step does not have a high iron content. In at least one embodiment, the cellulose fiber is acidified with acidic filtrate from a D stage of a multi-stage bleaching process.

In some embodiments, the method comprises oxidizing the cellulose fiber in one or more stages of a multi-stage bleaching sequence. In some embodiments, the method comprises oxidizing the cellulose fiber in a single stage of a multi-stage bleaching sequence. In some embodiments, the method comprises oxidizing the cellulose fiber at or near the end of a multi-stage bleaching sequence. In some embodiments, the method comprises oxidizing cellulose fiber in at least the fourth stage of a five-stage bleaching sequence.

In accordance with the disclosure, the multi-stage bleaching sequence can be any bleaching sequence that does not comprise an alkaline bleaching step following the oxidation step. In at least one embodiment, the multi-stage bleaching sequence is a five-stage bleaching sequence. In some embodiments, the bleaching sequence is a DEDED sequence. In some embodiments, the bleaching sequence is a $D_0E1D1E2D2$ sequence. In some embodiments, the bleaching sequence is a $D_0(EoP)D1E2D2$ sequence. In some embodiments the bleaching sequence is a $D_0(EO)D1E2D2$.

The non-oxidation stages of a multi-stage bleaching sequence may include any convention or after discovered series of stages, be conducted under conventional conditions, with the proviso that to be useful in producing the modified fiber described in the present disclosure, no alkaline bleaching step may follow the oxidation step.

In some embodiments, the oxidation is incorporated into the fourth stage of a multi-stage bleaching process. In some embodiments, the method is implemented in a five-stage bleaching process having a sequence of $D_0E1D1E2D2$, and the fourth stage (E2) is used for oxidizing kraft fiber.

In some embodiments, the kappa number increases after oxidation of the cellulose fiber. More specifically, one would typically expect a decrease in kappa number across this bleaching stage based upon the anticipated decrease in material, such as lignin, which reacts with the permanganate reagent. However, in the method as described herein, the kappa number of cellulose fiber may decrease because of the loss of impurities, e.g., lignin; however, the kappa number may increase because of the chemical modification of the fiber. Not wishing to be bound by theory, it is believed that the increased functionality of the modified cellulose provides additional sites that can react with the permanganate reagent. Accordingly, the kappa number of modified kraft fiber is elevated relative to the kappa number of standard kraft fiber.

In at least one embodiment, the oxidation occurs in a single stage of a bleaching sequence after both the iron or copper and peroxide have been added and some retention time provided. An appropriate retention is an amount of time that is sufficient to catalyze the hydrogen peroxide with the iron or copper. Such time will be easily ascertainable by a person of ordinary skill in the art.

In accordance with the disclosure, the oxidation is carried out for a time and at a temperature that is sufficient to produce the desired completion of the reaction. For example, the oxidation may be carried out at a temperature ranging from about 60 to about 80 degrees C., and for a time ranging from about 40 to about 80 minutes. The desired time and temperature of the oxidation reaction will be readily ascertainable by a person of skill in the art.

Advantageously, the cellulose fiber is digested to a target kappa number before bleaching. For example, when the oxidized cellulose is desired for paper grade or fluff pulp cellulose, the cellulose fiber may be digested in a two-vessel hydraulic digester with Lo-Solids™ cooking to a kappa number ranging from about 30 to about 32 before bleaching and oxidizing the cellulose. Alternatively, if oxidized cellulose is desired for cellulose derivative applications, for instance in the manufacture of cellulose ethers, cellulose fiber may be digested to a kappa number ranging from about 20 to about 24 before bleaching and oxidizing the cellulose according to the methods of this disclosure. In some embodiments, the cellulose fiber is digested and delignified in a conventional two-stage oxygen delignification step before bleaching and oxidizing the cellulose fiber. Advantageously, the delignification is carried out to a target kappa number ranging from about 6 to about 8 when the oxidized cellulose is intended for cellulose derivative applications, and a target kappa number ranging from about 12 to about 14 when the oxidized cellulose is intended for paper and/or fluff applications.

In some embodiments, the bleaching process is conducted under conditions to target about 88-90% final ISO brightness, such as ranging from about 85 to about 95%, or from about 88% to about 90%.

The disclosure also provides a method of treating cellulose fiber, comprising providing cellulose fiber, reducing the DP of the cellulose fiber, and maintaining the fiber length of the cellulose fiber. In some embodiments, the cellulose fiber is kraft fiber. In some embodiments, the DP of the cellulose fiber is reduced in a bleaching process. In some embodiments, the DP of the cellulose fiber is reduced at or near the end of a multi-stage bleaching sequence. In some embodiments, the DP is reduced in at least the fourth stage of a multi-stage bleaching sequence. In some embodiments, the DP is reduced in or after the fourth stage of a multi-stage bleaching sequence.

Alternatively, the multi-stage bleaching sequence may be altered to provide more robust bleaching conditions prior to oxidizing the cellulose fiber. In some embodiments, the method comprises providing more robust bleaching conditions prior to the oxidation step. More robust bleaching conditions may allow the degree of polymerization and/or viscosity of the cellulose fiber to be reduced in the oxidation step with lesser amounts of iron or copper and/or hydrogen peroxide. Thus, it may be possible to modify the bleaching sequence conditions so that the brightness and/or viscosity of the final cellulose product can be further controlled. For instance, reducing the amounts of peroxide and metal, while providing more robust bleaching conditions before oxidation, may provide a product with lower viscosity and higher brightness than an oxidized product produced with identical oxidation conditions but with less robust bleaching. Such conditions may be advantageous in some embodiments, particularly in cellulose ether applications.

In some embodiments, the methods of the disclosure further comprise reducing the crystallinity of cellulose fiber so that it is lower than the crystallinity of that cellulose fiber as measured before the oxidation stage. For example, in accordance with the methods of the disclosure, the crystallinity index of the cellulose fiber may be reduced up to 20% relative to the starting crystallinity index as measured before the oxidation stage.

In some embodiments, the methods of the disclosure further comprise treating the modified cellulose fiber with at least one caustic or alkaline substance. For example, in at least one embodiment, a method of treating cellulose fiber comprises providing an oxidized cellulose fiber of the disclosure, exposing the oxidized cellulose fiber to an alkaline or caustic substance, and then dry laying the cellulose product. Without being bound by theory, it is believed that the addition of at least one caustic substance to the modified cellulose may result in a cellulose fiber having very high functionality and very low fiber length.

It is known that cellulose comprising increased aldehyde groups may have advantageous properties in improving the wet strength of cellulose fibers. See, For Example, U.S. Pat. Nos. 6,319,361 to Smith et al., and 6,582,559 to Thornton et al. Such properties may be beneficial, for example, in absorbent material applications. In some embodiments, the disclosure provides a method for improving the wet strength of a product, comprising providing modified cellulose fiber of the disclosure and adding the modified cellulose fiber of the disclosure to a product, such as a paper product. For example, the method may comprise oxidizing cellulose fiber in a bleaching process, further treating the oxidized cellulose fiber with an acidic or caustic substance, and adding the treated fiber to a cellulose product.

In accordance with the disclosure, hydrogen peroxide is added to the cellulose fiber in acidic media in an amount sufficient to achieve the desired oxidation and/or degree of polymerization and/or viscosity of the final cellulose product. For example, peroxide can be added in an amount of from about 0.1 to about 4%, or from about 1% to about 3%, or from about 1% to about 2%, or from about 2% to about 3%, based on the dry weight of the pulp.

Iron or copper are added at least in an amount sufficient to catalyze the oxidation of the cellulose with peroxide. For example, iron can be added in an amount ranging from about 25 to about 200 ppm based on the dry weight of the kraft pulp. A person of skill in the art will be able to readily optimize the amount of iron or copper to achieve the desired level or amount of oxidation and/or degree of polymerization and/or viscosity of the final cellulose product.

In some embodiments, the method further involves adding steam either before or after the addition of hydrogen peroxide.

In some embodiments, the final DP and/or viscosity of the pulp can be controlled by the amount of iron or copper and hydrogen peroxide and the robustness of the bleaching conditions prior to the oxidation step. A person of skill in the art will recognize that other properties of the modified kraft fiber of the disclosure may be affected by the amounts of iron or copper and hydrogen peroxide and the robustness of the bleaching conditions prior to the oxidation step. For example, a person of skill in the art may adjust the amounts of iron or copper and hydrogen peroxide and the robustness of the bleaching conditions prior to the oxidation step to target or achieve a desired brightness in the final product and/or a desired degree of polymerization or viscosity.

In some embodiments, the disclosure provides a method of modifying cellulose fiber, comprising providing cellulose fiber, reducing the degree of polymerization of the cellulose fiber, and maintaining the fiber length of the cellulose fiber.

In some embodiments, the oxidized kraft fiber of the disclosure is not refined. Refining of the oxidized kraft fiber may have a negative impact on its fiber length and integrity, for instance refining the fiber may cause the fiber to fall apart.

In some embodiments, each stage of the five-stage bleaching process includes at least a mixer, a reactor, and a washer (as is known to those of skill in the art).

In some embodiments, a kraft pulp is acidified on a D1 stage washer, the iron source is also added to the kraft pulp on the D1 stage washer, the peroxide is added following the iron source (or copper source) at an addition point in the mixer or pump before the E2 stage tower, the kraft pulp is reacted in the E2 tower and washed on the E2 washer, and steam may optionally be added before the E2 tower in a steam mixer.

In some embodiments, iron (or copper) can be added up until the end of the D1 stage, or the iron (or copper) can also be added at the beginning of the E2 stage, provided that the pulp is acidified first (i.e., prior to addition of the iron) at the D1 stage. Steam may be optionally added either before or after the addition of the peroxide.

In an exemplary embodiment, the method for preparing a low viscosity modified cellulose fiber may involve bleaching kraft pulp in a multi-stage bleaching process and reducing the DP of the pulp at or near a final stage of the multi-stage bleaching process (for example in the 4th stage of a multi-stage bleaching process, for example in the 4th stage of a 5 stage bleaching process) using a treatment with hydrogen peroxide in an acidic media and in the presence of iron. For instance, the final DP of the pulp may be controlled by the appropriate application of the iron or copper and hydrogen peroxide, as further described in the Examples section. In some embodiments, the iron or copper and hydrogen peroxide is provided in amounts and under conditions appropriate for producing a low DP fiber (i.e., a fiber having a DPw ranging from about 1180 to about 1830, or a 0.5% Capillary CED viscosity ranging from about 7 to about 13 mPa·s). In some exemplary embodiments, the iron or copper and hydrogen peroxide may be provided in amounts and under conditions appropriate for producing an ultra low DP fiber (i.e., a fiber having a DPw ranging from about 700 to about 1180, or a 0.5% 0.5% Capillary CED viscosity ranging from about 3.0 to about 7 mPa·s).

For example, in some embodiments, the treatment with hydrogen peroxide in an acidic media with iron or copper may involve adjusting the pH of the kraft pulp to a pH ranging from about 2 to about 5, adding a source of iron to the acidified pulp, and adding hydrogen peroxide to the kraft pulp.

In some embodiments, for example, the method of preparing a modified cellulose fiber within the scope of the disclosure may involve acidifying the kraft pulp to a pH ranging from about 2 to about 5 (using for example sulfuric acid), mixing a source of iron (for example ferrous sulfate, for example ferrous sulfate heptahydrate) with the acidified kraft pulp at an application of from about 25 to about 250 ppm $Fe^{+2}$ based on the dry weight of the kraft pulp at a consistency ranging from about 1% to about 15% and also hydrogen peroxide, which can be added as a solution at a concentration of from about 1% to about 50% by weight and in an amount ranging from about 0.1% to about 1.5% based on the dry weight of the kraft pulp. In some embodiments, the ferrous sulfate solution is mixed with the kraft pulp at a consistency ranging from about 7% to about 15%. In some embodiments the acidic kraft pulp is mixed with the iron source and reacted with the hydrogen peroxide for a time period ranging from about 40 to about 80 minutes at a temperature ranging from about 60 to about 80 degrees C.

In some embodiments, the method of preparing a modified cellulose fiber within the scope of this disclosure involves reducing DP by treating a kraft pulp with hydrogen peroxide in an acidic media in the presence of iron (or copper), wherein the acidic, hydrogen peroxide and iron (or copper) treatment is incorporated into a multi-stage bleaching process. In some embodiments, the treatment with iron, acid and hydrogen peroxide is incorporated into a single stage of the multi-stage bleaching process. In some embodiments, the treatment with iron (or copper), acid and hydrogen peroxide is incorporated into a single stage that is at or near the end of the multi-stage bleaching process. In some embodiments, the treatment with iron (or copper), acid and hydrogen peroxide is incorporated into the fourth stage of a multi-stage bleaching process. For example, the pulp treatment may occur in a single stage, such as the E2 stage, after both the iron (or copper) and peroxide have been added and some retention time provided. In some embodiments, each stage of a five stage bleaching process includes at least a mixer, a reactor, and a washer (as is known to those of skill in the art), and the kraft pulp may be acidified on the D1 stage washer, the iron source may also be added to the kraft pulp on the D1 stage washer, the peroxide may be added following the iron source (or copper source) at an addition point in the mixer or pump before the E2 stage tower, the kraft pulp may be reacted in the E2 tower and washed on the E2 washer, and steam may optionally be added before the E2 tower in a steam mixer. In some embodiments, for example, iron (or copper) can be added up until the end of the D1 stage, or the iron (or copper) could also be added at the beginning of the E2 stage, provided that the pulp is acidified first (i.e., prior to addition of the iron) at the D1 stage, extra acid may be added if needed to bring the pH into the range of from about 3 to about 5, and peroxide may be added after the iron (or copper). Steam may be added either before or after the addition of the peroxide For example, in one embodiment, the above-described five stage bleaching processes conducted with a softwood cellulose starting material may produce modified cellulose fiber having one or more of the following properties: an average fiber length of at least 2.2 mm, a viscosity ranging from about 3.0 mPa·s to less than 13 mPa·s, an S10 caustic solubility ranging from about 16% to about 20%, an S18 caustic solubility ranging from about 14% to about 18%, a carboxyl content ranging from about 2 meq/100 g to about 6 meq/100 g, an aldehyde content ranging from about 1 meq/100 g to about 3 meq/100 g, a carbonyl content of from about 1 to 4, a freeness ranging from about 700 mls to about 760 mls, a fiber strength ranging from about 5 km to about 8 km, and a brightness ranging from about 85 to about 95 ISO. For example, in some embodiments, the above-described exemplary five stage bleaching processes may produce modified cellulose softwood fibers having each of the afore-mentioned properties.

According to another example, wherein the cellulose fiber is a softwood fiber, the above-described exemplary five stage bleaching processes may produce a modified cellulose softwood fiber having an average fiber length that is at least 2.0 mm (for example ranging from about 2.0 mm to about 3.7 mm, or from about 2.2 mm to about 3.7 mm), a viscosity that is less than 13 mPa·s (for example a viscosity ranging from about 3.0 mPa·s to less than 13 mPa·s, or from about 3.0 mPa·s to about 5.5 mPa·s, or from about 3.0 mPa·s to about 7 mPa·s, or from about 7 mPa·s to less than 13 mPa·s), and a brightness of at least 85 (for example ranging from about 85 to about 95).

In some embodiments, the disclosure provides a method for producing fluff pulp, comprising providing modified kraft fiber of the disclosure and then producing a fluff pulp. For example, the method comprises bleaching kraft fiber in a multi-stage bleaching process, oxidizing the fiber in at least the fourth or fifth stage of the multi-stage bleaching process with hydrogen peroxide under acidic conditions and a catalytic amount of iron or copper, and then forming a fluff pulp. In at least one embodiment, the fiber is not refined after the multi-stage bleaching process.

The disclosure also provides a method for reducing odor, such as odor from bodily waste, for example odor from urine or blood. In some embodiments, the disclosure provides a method for controlling odor, comprising providing a modified bleached kraft fiber according to the disclosure, and applying an odorant to the bleached kraft fiber such that the atmospheric amount of odorant is reduced in comparison with the atmospheric amount of odorant upon application of an equivalent amount of odorant to an equivalent weight of standard kraft fiber. In some embodiments the disclosure provides a method for controlling odor comprising inhibiting bacterial odor generation. In some embodiments, the disclosure provides a method for controlling odor comprising absorbing odorants, such as nitrogenous odorants, onto a modified kraft fiber. As used herein, "nitrogenous odorants" is understood to mean odorants comprising at least one nitrogen.

In at least one embodiment, a method of reducing odor comprises providing modified cellulose fiber according to the disclosure, and applying an odorant, such as a nitrogenous compound, for instance ammonia, or an organism that is capable of generating a nitrogenous compound to the modified kraft fiber. In some embodiments, the method further comprises forming a fluff pulp from modified cellulose fiber before adding an odorant to the modified kraft fiber. In some embodiments, the odorant comprises at least one bacteria capable of producing nitrogenous compounds. In some embodiments, the odorant comprises nitrogenous compounds, such as ammonia.

In some embodiments, the method of reducing odor further comprises absorbing ammonia onto modified cellulose fiber. In some embodiments, the method of reducing odor further comprises inhibiting bacterial ammonia production. In some embodiments, the method of inhibiting bacterial ammonia production comprises inhibiting bacterial growth. In some embodiments, the method of inhibiting bacterial ammonia production comprises inhibiting bacterial urea synthesis.

In some embodiments, a method of reducing odor comprises combining modified cellulose fiber with at least one other odor reductant, and then applying an odorant to the modified cellulose fiber combined with odor reductant.

Exemplary odor reductants are known in the art, and include, for example, odor reducing agents, odor masking agents, biocides, enzymes, and urease inhibitors. For instance, modified cellulose fiber may be combined with at least one odor reductant chosen from zeolites, activated carbons, diatomaceous earth, cyclodextrins, clay, chelating agents, such as those containing metal ions, such as copper, silver or zinc ions, ion exchange resins, antibacterial or antimicrobial polymers, and/or aromatizers.

In some embodiments, the modified cellulose fiber is combined with at least one super absorbent polymer (SAP). In some embodiments, the SAP may by an odor reductant. Examples of SAP that can be used in accordance with the disclosure include, but are not limited to, Hysorb™ sold by the company BASF, Aqua Keep® sold by the company Sumitomo, and FAVOR®, sold by the company Evonik.

II. Kraft Fibers

Reference is made herein to "standard," "conventional," or "traditional," kraft fiber, kraft bleached fiber, kraft pulp or kraft bleached pulp. Such fiber or pulp is often described as a reference point for defining the improved properties of the present invention. As used herein, these terms are interchangeable and refer to the fiber or pulp which is identical in composition to and processed in a like manner to the target fiber or pulp without having been subject to any oxidation, either alone or followed by one or more of alkaline or acid treatments (i.e., processed in the standard or conventional manner). As used herein, the term "modified"

refers to fiber that has been subject to an oxidation treatment, either alone or followed by one or more of alkaline or acid treatments.

Physical characteristics (for example, fiber length and viscosity) of the modified cellulose fiber mentioned in the specification are measured in accordance with protocols provided in the Examples section.

The present disclosure provides kraft fiber with low and ultra-low viscosity. Unless otherwise specified, "viscosity" as used herein refers to 0.5% Capillary CED viscosity measured according to TAPPI T230-om99 as referenced in the protocols. Modified kraft fiber of the present invention exhibits unique characteristics which are indicative of the chemical modifications that have been made to it. More specifically, fiber of the present invention exhibits characteristics similar to those of standard kraft fiber, i.e., length and freeness, but also exhibits some very different characteristics which are a function of the increased number of functional groups that are included in the modified fiber. This modified fiber exhibits unique characteristics when subjected to the cited TAPPI test for measuring viscosity. Specifically, the cited TAPPI test treats fiber with a caustic agent as part of the test method. The application of caustic to the modified fiber, as described, causes the modified fiber to hydrolyze differently than standard kraft fiber thus reporting a viscosity which is generally lower than the viscosity of standard kraft fiber. Accordingly, a person of skill in the art will understand that the reported viscosities may be affected by the viscosity measurement method. For purposes of the present invention, the viscosities reported herein as measured by the cited TAPPI method represent the viscosity of the kraft fiber used to calculate the degree of polymerization of the fiber.

Unless otherwise specified, "DP" as used herein refers to average degree of polymerization by weight (DPw) calculated from 0.5% Capillary CED viscosity measured according to TAPPI T230-om99. See, e.g., J. F. Cellucon Conference in *The Chemistry and Processing of Wood and Plant Fibrous Materials*, p. 155, test protocol 8, 1994 (Woodhead Publishing Ltd., Abington Hall, Abinton Cambridge CBI 6AH England, J. F. Kennedy et al. eds.) "Low DP" means a DP ranging from about 1160 to about 1860 or a viscosity ranging from about 7 to about 13 mPa·s. "Ultra low DP" fibers means a DP ranging from about 350 to about 1160 or a viscosity ranging from about 3 to about 7 mPa·s.

Without wishing to be bound by theory, it is believed that the fiber of the present invention presents an artificial Degree of Polymerization when DP is calculated via CED viscosity measured according to TAPPI T230-om99. Specifically, it is believed that the catalytic oxidation treatment of the fiber of the present invention does not break the cellulose down to the extent indicated by the measured DP, but instead largely has the effect of opening up bonds and adding substituents that make the cellulose more reactive, instead of cleaving the cellulose chain. It is further believed that the CED viscosity test (TAPPI T230-om99), which begins with the addition of caustic, has the effect of cleaving the cellulose chain at the new reactive sites, resulting in a cellulose polymer which has a much higher number of shorter segments than are found in the fiber's pre-testing state. This is confirmed by the fact that the fiber length is not significantly diminished during production.

In some embodiments, modified cellulose fiber has a DP ranging from about 350 to about 1860. In some embodiments, the DP ranges from about 710 to about 1860. In some embodiments, the DP ranges from about 350 to about 910. In some embodiments, the DP ranges from about 350 to about 1160. In some embodiments, the DP ranges from about 1160 to about 1860. In some embodiments, the DP is less than 1860, less than 1550, less than 1300, less than 820, or less than 600.

In some embodiments, modified cellulose fiber has a viscosity ranging from about 3.0 mPa·s to about 13 mPa·s. In some embodiments, the viscosity ranges from about 4.5 mPa·s to about 13 mPa·s. In some embodiments, the viscosity ranges from about 3.0 mPa·s to about 5.5 mPa·s. In some embodiments, the viscosity ranges from about 3.0 mPa·s to about 7 mPa·s. In some embodiments, the viscosity ranges from about 7 mPa·s to about 13 mPa·s. In some embodiments, the viscosity is less than 13 mPa·s, less than 10 mPa·s, less than 8 mPa·s, less than 5 mPa·s, or less than 4 mPa·s.

In some embodiments, the modified kraft fiber of the disclosure maintains its freeness during the bleaching process. In some embodiments, the modified cellulose fiber has a "freeness" of at least about 690 mls, such as at least about 700 mls, or about 710 mls, or about 720 mls, or about 730 mls.

In some embodiments, modified kraft fiber of the disclosure maintains its fiber length during the bleaching process.

In some embodiments, when the modified cellulose fiber is a softwood fiber, the modified cellulose fiber has an average fiber length, as measured in accordance with Test Protocol 12, described in the Example section below, that is about 2 mm or greater. In some embodiments, the average fiber length is no more than about 3.7 mm. In some embodiments, the average fiber length is at least about 2.2 mm, about 2.3 mm, about 2.4 mm, about 2.5 mm, about 2.6 mm, about 2.7 mm, about 2.8 mm, about 2.9 mm, about 3.0 mm, about 3.1 mm, about 3.2 mm, about 3.3 mm, about 3.4 mm, about 3.5 mm, about 3.6 mm, or about 3.7 mm. In some embodiments, the average fiber length ranges from about 2 mm to about 3.7 mm, or from about 2.2 mm to about 3.7 mm.

In some embodiments, when the modified cellulose fiber is a hardwood fiber, the modified cellulose fiber has an average fiber length from about 0.75 to about 1.25 mm. For example, the average fiber length may be at least about 0.85 mm, such as about 0.95 mm, or about 1.05 mm, or about 1.15 mm.

In some embodiments, modified kraft fiber of the disclosure has a brightness equivalent to kraft fiber standard kraft fiber. In some embodiments, the modified cellulose fiber has a brightness of at least 85, 86, 87, 88, 89, or 90 ISO. In some embodiments, the brightness is no more than about 92. In some embodiments, the brightness ranges from about 85 to about 92, or from about 86 to about 90, or from about 87 to about 90, or from about 88 to about 90.

In some embodiments, modified cellulose fiber of the disclosure is more compressible and/or embossable than standard kraft fiber. In some embodiments, modified cellulose fiber may be used to produce structures that are thinner and/or have higher density than structures produced with equivalent amounts of standard kraft fiber.

In some embodiments, modified cellulose fiber of the disclosure may be compressed to a density of at least about 0.21 g/cc, for example about 0.22 g/cc, or about 0.23 g/cc, or about 0.24 g/cc. In some embodiments, modified cellulose fiber of the disclosure may be compressed to a density ranging from about 0.21 to about 0.24 g/cc. In at least one embodiment, modified cellulose fiber of the disclosure, upon compression at 20 psi gauge pressure, has a density ranging from about 0.21 to about 0.24 g/cc.

In some embodiments, modified cellulose fiber of the disclosure, upon compression under a gauge pressure of about 5 psi, has a density ranging from about 0.110 to about 0.114 g/cc. For example, modified cellulose fiber of the disclosure, upon compression under a gauge pressure of about 5 psi, may have a density of at least about 0.110 g/cc, for example at least about 0.112 g/cc, or about 0.113 g/cc, or about 0.114 g/cc.

In some embodiments, modified cellulose fiber of the disclosure, upon compression under a gauge pressure of about 10 psi, has a density ranging from about 0.130 to about 0.155 g/cc. For example, the modified cellulose fiber of the disclosure, upon compression under a gauge pressure of about 10 psi, may have a density of at least about 0.130 g/cc, for example at least about 0.135 g/cc, or about 0.140 g/cc, or about 0.145 g/cc, or about 0.150 g/cc.

In some embodiments, modified cellulose fiber of the disclosure can be compressed to a density of at least about 8% higher than the density of standard kraft fiber. In some embodiments, the modified cellulose fiber of the disclosure have a density of about 8% to about 16% higher than the density of standard kraft fiber, for example from about 10% to about 16% higher, or from about 12% to about 16% higher, or from about 13% to about 16% higher, or from about 14% to about 16% higher, or from about 15% to about 16% higher.

In some embodiments, modified kraft fiber of the disclosure has increased carboxyl content relative to standard kraft fiber.

In some embodiments, modified cellulose fiber has a carboxyl content ranging from about 2 meq/100 g to about 9 meq/100 g. In some embodiments, the carboxyl content ranges from about 3 meq/100 g to about 8 meq/100 g. In some embodiments, the carboxyl content is about 4 meq/100 g. In some embodiments, the carboxyl content is at least about 2 meq/100 g, for example, at least about 2.5 meq/100 g, for example, at least about 3.0 meq/100 g, for example, at least about 3.5 meq/100 g, for example, at least about 4.0 meq/100 g, for example, at least about 4.5 meq/100 g, or for example, at least about 5.0 meq/100 g.

Modified kraft fiber of the disclosure has increased aldehyde content relative to standard bleached kraft fiber. In some embodiments, the modified kraft fiber has an aldehyde content ranging from about 1 meq/100 g to about 9 meq/100 g. In some embodiments, the aldehyde content is at least about 1.5 meq/100 g, about 2 meq/100 g, about 2.5 meq/100 g, about 3.0 meq/100 g, about 3.5 meq/100 g, about 4.0 meq/100 g, about 4.5 meq/100 g, or about 5.0 meq/100 g, or at least about 6.5 meq, or at least about 7.0 meq.

In some embodiments, the modified cellulose fiber has a ratio of total aldehyde to carboxyl content of greater than about 0.3, such as greater than about 0.5, such as greater than about 1, such as greater than about 1.4. In some embodiments, the aldehyde to carboxyl ratio ranges from about 0.3 to about 1.5. In some embodiments, the ratio ranges from about 0.3 to about 0.5. In some embodiments, the ratio ranges from about 0.5 to about 1. In some embodiments, the ratio ranges from about 1 to about 1.5.

In some embodiments, modified kraft fiber has higher kink and curl than standard kraft fiber. Modified kraft fiber according to the present invention has a kink index in the range of about 1.3 to about 2.3. For instance, the kink index may range from about 1.5 to about 2.3, or from about 1.7 to about 2.3 or from about 1.8 to about 2.3, or from about 2.0 to about 2.3. Modified kraft fiber according to the present disclosure may have a length weighted curl index in the range of about 0.11 to about 0.23, such as from about 0.15 to about 0.2.

In some embodiments, the crystallinity index of modified kraft fiber is reduced from about 5% to about 20% relative to the crystallinity index of standard kraft fiber, for instance from about 10% to about 20%, or from about 15% to about 20%.

In some embodiments, modified cellulose according to the present disclosure has an R10 value ranging from about 65% to about 85%, for instance from about 70% to about 85%, or from about 75% to about 85%. In some embodiments, modified fiber according to the disclosure has an R18 value ranging from about 75% to about 90%, for instance from about 80% to about 90%, for example from about 80% to about 87%. The R18 and R10 content is described in TAPPI 235. R10 represents the residual undissolved material that is left extraction of the pulp with 10 percent by weight caustic and R18 represents the residual amount of undissolved material left after extraction of the pulp with an 18% caustic solution. Generally, in a 10% caustic solution, hemicellulose and chemically degraded short chain cellulose are dissolved and removed in solution. In contrast, generally only hemicellulose is dissolved and removed in an 18% caustic solution. Thus, the difference between the R10 value and the R18 value, (R=R18−R10), represents the amount of chemically degraded short-chained cellulose that is present in the pulp sample.

Based on one or more of the above-cited properties, such as the kink and curl of the fiber, the increased functionality, and the crystallinity of the modified kraft fiber, a person of skill in the art would expect the modified kraft fiber of the disclosure to have certain characteristics that standard kraft fiber does not possess. For instance, it is believed that kraft fiber of the disclosure may be more flexible than standard kraft fiber, and may elongate and/or bend and/or exhibit elasticity and/or increase wicking. Moreover, without being bound by theory, it is expected that modified kraft fiber may provide a physical structure, for example in a fluff pulp, that would either cause fiber entanglement and fiber/fiber bonding or would entangle materials applied to the pulp, such that they these materials remain in a relatively fixed spatial position within the pulp, retarding their dispersion. Additionally, it is expected, at least because of the reduced crystallinity relative to standard kraft fiber, that modified kraft fiber of the disclosure would be softer than standard kraft fiber, enhancing their applicability in absorbent product applications, for example, such as diaper and bandage applications.

In some embodiments, modified cellulose fiber has an S10 caustic solubility ranging from about 16% to about 30%, or from about 14% to about 16%. In some embodiments, modified cellulose fiber has an S18 caustic solubility ranging from about 14% to about 22%, or from about 14% to about 16%. In some embodiments, modified cellulose fiber has a ΔR (difference between S10 and S18) of about 2.9 or greater. In some embodiments the ΔR is about 6.0 or greater.

In some embodiments, modified cellulose fiber strength, as measured by wet zero span breaking length, ranges from about 4 km to about 10 km, for instance, from about 5 km to about 8 km. In some embodiments, the fiber strength is at least about 4 km, about 5 km, about 6 km, about 7 km, or about 8 km. In some embodiments, the fiber strength ranges from about 5 km to about 7 km, or from about 6 km to about 7 km.

In some embodiments, modified kraft fiber has odor control properties. In some embodiments, modified kraft fiber is capable of reducing the odor of bodily waste, such as urine or menses. In some embodiments modified kraft fiber absorbs ammonia. In some embodiments, modified kraft fiber inhibits bacterial odor production, for example, in some embodiments, modified kraft fiber inhibits bacterial ammonia production.

In at least one embodiment, modified kraft fiber is capable of absorbing odorants, such as nitrogen containing odorants, for example ammonia.

As used herein, the term "odorant" is understood to mean a chemical material that has a smell or odor, or that is capable of interacting with olfactory receptors, or to mean an organism, such as a bacteria, that is capable of generating compounds that generate a smell or odor, for example a bacteria that produces urea.

In some embodiments, modified kraft fiber reduces atmospheric ammonia concentration more than a standard bleached kraft fiber reduces atmospheric ammonia. For example, modified kraft fiber may reduce atmospheric ammonia by absorbing at least part of an ammonia sample applied to modified kraft fiber, or by inhibiting bacterial ammonia production. In at least one embodiment, modified kraft fiber absorbs ammonia and inhibits bacterial ammonia production.

In some embodiments, modified kraft fiber reduces at least about 40% more atmospheric ammonia than standard kraft fibers, for example at least about 50% more, or about 60% more, or about 70% more, or about 75% more, or about 80% more, or about 90% more ammonia than standard kraft fiber.

In some embodiments, modified kraft fiber of the disclosure, after application of 0.12 g of a 50% solution of ammonium hydroxide to about nine grams of modified cellulose and a 45 minute incubation time, reduces atmospheric ammonia concentration in a volume of 1.6 L to less than 150 ppm, for example, less than about 125 ppm, for example less than bout 100 ppm, for example, less than about 75 ppm, for example, less than about 50 ppm.

In some embodiments, modified kraft fiber absorbs from about 5 to about 10 ppm ammonia per gram of fiber. For instance, the modified cellulose may absorb from about 6 to about 10 ppm, or from about 7 to about 10 ppm, or from about 8 to about 10 ppm ammonia per gram of fibers.

In some embodiments, modified kraft fiber has both improved odor control properties and improved brightness compared to standard kraft fiber. In at least one embodiment, modified cellulose fiber has a brightness ranging from about 85 to about 92 and is capable of reducing odor. For example, the modified cellulose may have a brightness ranging from about 85 to about 92, and absorbs from about 5 to about 10 ppm ammonia for every gram of fiber.

In some embodiments, modified cellulose fiber has an MEM Elution Cytotoxicity Test, ISO 10993-5, of less than 2 on a zero to four scale. For example the cytotoxicity may be less than about 1.5 or less than about 1.

It is known that oxidized cellulose, in particular cellulose comprising aldehyde and/or carboxylic acid groups, exhibits anti-viral and/or antimicrobial activity. See, e.g., Song et al., *Novel antiviral activity of dialdehyde starch*, Electronic J. Biotech., Vol. 12, No. 2, 2009; U.S. Pat. No. 7,019,191 to Looney et al. For instance, aldehyde groups in dialdehyde starch are known to provide antiviral activity, and oxidized cellulose and oxidized regenerated cellulose, for instance containing carboxylic acid groups, have frequently been used in wound care applications in part because of their bactericidal and hemostatic properties. Accordingly, in some embodiments, the cellulose fibers of the disclosure may exhibit antiviral and/or antimicrobial activity. In at least one embodiment, modified cellulose fiber exhibits antibacterial activity. In some embodiments, modified cellulose fiber exhibits antiviral activity.

In some embodiments, modified kraft fiber of the disclosure has a level-off DP of less than 200, such as less than about 100, or less than about 80, or less than about 75, or less than about 50 or less than or equal to about 48. Level-off DP can be measured by methods known in the art, for example by methods disclosed in Battista, et al., Level-Off Degree of Polymerization, Division of Cellulose Chemistry, Symposium on Degradation of Cellulose and Cellulose Derivatives, $127^{th}$ Meeting, ACS, Cincinnati, Ohio, March-April 1955.

In some embodiments modified kraft fiber has a kappa number of less than about 2. For example, modified kraft fiber may have a kappa number less than about 1.9. In some embodiments modified kraft fiber has a kappa number ranging from about 0.1 to about 1, such as from about 0.1 to about 0.9, such as from about 0.1 to about 0.8, for example from about 0.1 to about 0.7, for instance from about 0.1 to about 0.6, such as from about 0.1 to about 0.5, or from about 0.2 to about 0.5.

In some embodiments, modified kraft fiber is kraft fiber bleached in a multi-stage process, wherein an oxidation step is followed by at least one bleaching step. In such embodiments, the modified fiber after the at least one bleaching step has a "k number", as measured according to TAPPI UM 251, ranging from about 0.2 to about 1.2. For example, the k number may range from about 0.4 to about 1.2, or from about 0.6 to about 1.2, or from about 0.8 to about 1.2, or from about 1.0 to about 1.2.

In some embodiments, the modified cellulose fiber has a copper number greater than about 2. In some embodiments, the copper number is greater than 2.0. In some embodiments, the copper number is greater than about 2.5. For example, the copper number may be greater than about 3. In some embodiments, the copper number ranges from about 2.5 to about 5.5, such as from about 3 to about 5.5, for instance from about 3 to about 5.2.

In at least one embodiment, the hemicellulose content of the modified kraft fiber is substantially the same as standard unbleached kraft fiber. For example, the hemicellulose content for a softwood kraft fiber may range from about 16% to about 18%. For instance, the hemicellulose content of a hardwood kraft fiber may range from about 18% to about 25%.

III. Further Processing—Acid/Alkaline Hydrolysis

In some embodiments, modified kraft fiber of the disclosure is suitable for production of cellulose derivatives, for example for production of lower viscosity cellulose ethers, cellulose esters, and microcrystalline cellulose. In some embodiments, modified kraft fiber of the disclosure is hydrolyzed modified kraft fiber. As used herein "hydrolyzed modified kraft fiber," hydrolyzed kraft fiber" and the like are understood to mean fiber that has been hydrolyzed with any acid or alkaline treatment know to depolymerized the cellulose chain. In some embodiments, the kraft fiber according to the disclosure is further treated to reduce its viscosity and/or degree of polymerization. For example, the kraft fiber according to the disclosure may be treated with an acid or a base.

In some embodiments, the disclosure provides a method of treating kraft fiber, comprising bleaching kraft fiber according to the disclosure, and then hydrolyzing the bleached kraft fiber. Hydrolysis can be by any method known to those of ordinary skill in the art. In some embodiments, the bleached kraft fiber is hydrolyzed with at least one acid. In some embodiments, the bleached kraft fiber is hydrolyzed with an acid chosen from sulfuric acid, mineral acids, and hydrochloric acid The disclosure also provides a method for producing cellulose ethers. In some embodiments, the method for producing cellulose ethers comprises bleaching kraft fiber in accordance with the disclosure, treating the bleached kraft fiber with at least one alkali agent, such as sodium hydroxide and reacting the fibers with at least one etherying agent.

The disclosure also provides methods for producing cellulose esters. In some embodiments, the method for producing cellulose esters comprises bleaching kraft fiber in accordance with the disclosure, treating the bleached kraft fiber with a catalyst, such as sulfuric acid, then treating the fiber with at least one acetic anhydride or acetic acid. In an alternative embodiment, the method for producing cellulose acetates comprises bleaching kraft fiber in accordance with the disclosure, hydrolyzing the bleached kraft fiber with sulfuric acid, and treating the hydrolyzed kraft fiber with at least one acetic anhydride or acetic acid.

The disclosure also provides methods for producing microcrystalline cellulose. In some embodiments, the method for producing microcrystalline cellulose comprises providing bleached kraft fiber according to the disclosure, hydrolyzing the bleached kraft fiber with at least one acid until the desired DP is reached or under conditions to arrive at the level-off DP. In a further embodiment, the hydrolyzed bleached kraft fiber is mechanically treated, for example by grinding, milling, or shearing. Methods for mechanically treating hydrolyzed kraft fibers in microcrystalline cellulose production are known to persons of skill in the art, and may provide desired particle sizes. Other parameters and conditions for producing microcrystalline cellulose are known, and are described for example in U.S. Pat. Nos. 2,978,446 and 5,346,589.

In some embodiments, modified kraft fiber according to the disclosure is further treated with an alkaline agent or caustic agent to reduce its viscosity and/or degree of polymerization. Alkaline treatment, a pH above about 9, causes dialdehydes to react and undergo a beta-hydroxy elimination. This further modified fiber that has been treated with an alkaline agent, may also be useful in the production of tissue, towel and also other absorbent products and in cellulose derivative applications. In more conventional papermaking, strength agents are often added to the fiber slurry to modify the physical properties of the end products. This alkaline modified fiber may be used to replace some or all of the strength adjusting agent used in the production of tissue and towel.

As described above, there are three types of fiber products that can be prepared by the processes described herein. The first type is fiber that has been treated by catalytic oxidation, which fiber is almost indistinguishable from its conventional counterpart (at least as far as physical and papermaking properties are concerned), yet it has functionality associated with it that gives it one or more of its odor control properties, compressibility, low and ultra low DP, and/or the ability to convert "in-situ" into a low DP/low viscosity fiber under either alkaline or acid hydrolysis conditions, such as the conditions of cellulose derivative production, e.g., ether or acetate production. The physical characteristics and papermaking properties of this type of fiber make it appropriate for use in typical papermaking and absorbent product applications. The increased functionality, e.g., aldehydic and carboxylic, and the properties associated with that functionality, on the other hand, make this fiber more desirable and more versatile than standard kraft fiber.

The second type of fiber is fiber that has been subjected to catalytic oxidation and then has been treated with an alkaline or caustic agent. The alkaline agent causes the fiber to break down at the sites of carbonyl functionality that were added through the oxidation process. This fiber has different physical and papermaking properties than the fiber only subjected to oxidation, but may exhibit the same or similar DP levels since the test used to measure viscosity and thereby DP subjects the fiber to a caustic agent. It would be evident to the skilled artisan that different alkaline agents and levels may provide different DP levels.

The third type of fiber is fiber that has been subjected to catalytic oxidation and then been treated in an acid hydrolysis step. The acid hydrolysis results in a breakdown of the fiber, possibly to levels consistent with its level-off DP.

Fiber produced as described can, in some embodiments, be treated with a surface active agent. The surface active agent for use in the present invention may be solid or liquid. The surface active agent can be any surface active agent, including by not limited to softeners, debonders, and surfactants that is not substantive to the fiber, i.e., which does not interfere with its specific absorption rate. As used herein a surface active agent that is "not substantive" to the fiber exhibits an increase in specific absorption rate of 30% or less as measured using the pfi test as described herein. According to one embodiment, the specific absorption rate is increased by 25% or less, such as 20% or less, such as 15% or less, such as 10% or less. Not wishing to be bound by theory, the addition of surfactant causes competition for the same sites on the cellulose as the test fluid. Thus, when a surfactant is too substantive, it reacts at too many sites reducing the absorption capability of the fiber.

As used herein PFI is measured according to SCAN-C-33:80 Test Standard, Scandinavian Pulp, Paper and Board Testing Committee. The method is generally as follows. First, the sample is prepared using a PFI Pad Former. Turn on the vacuum and feed approximately 3.01 g fluff pulp into the pad former inlet. Turn off the vacuum, remove the test piece and place it on a balance to check the pad mass. Adjust the fluff mass to 3.00+0.01 g and record as Massdry. Place the fluff into the test cylinder. Place the fluff containing cylinder in the shallow perforated dish of an Absorption Tester and turn the water valve on. Gently apply a 500 g load to the fluff pad while lifting the test piece cylinder and promptly press the start button. The Tester will fun for 30 s before the display will read 00.00. When the display reads 20 seconds, record the dry pad height to the nearest 0.5 mm (Heightdry). When the display again reads 00.00, press the start button again to prompt the tray to automatically raise the water and then record the time display (absorption time, T). The Tester will continue to run for 30 seconds. The water tray will automatically lower and the time will run for another 30 S. When the display reads 20 s, record the wet pad height to the nearest 0.5 mm (Heightwet). Remove the sample holder, transfer the wet pad to the balance for measurement of Masswet and shut off the water valve. Specific Absorption Rate (s/g) is T/Massdry. Specific Capacity (g/g) is (Masswet−Massdry)/Massdry. Wet Bulk (cc/g) is [19.64 cm2×Heightwet/3]/10. Dry Bulk is [19.64 cm2×Heightdry/3]/10. The reference standard for comparison with the surfactant treated fiber is an identical fiber without the addition of surfactant.

It is generally recognized that softeners and debonders are often available commercially only as complex mixtures rather than as single compounds. While the following discussion will focus on the predominant species, it should be understood that commercially available mixtures would generally be used in practice. Suitable softener, debonder and surfactants will be readily apparent to the skilled artisan and are widely reported in the literature.

Suitable surfactants include cationic surfactants, anionic, and nonionic surfactants that are not substantive to the fiber. According to one embodiment, the surfactant is a non-ionic surfactant. According to one embodiment, the surfactant is a cationic surfactant. According to one embodiment, the surfactant is a vegetable based surfactant, such as a vegetable based fatty acid, such as a vegetable based fatty acid quaternary ammonium salt. Such compounds include DB999 and DB1009, both available from Cellulose Solutions. Other surfactants may be including, but not limited to Berol 388 an ethoxylated nonylphenol ether from Akzo Nobel, and TQ-2021 and TQ-2028, both from Ashland, Inc.

Biodegradable softeners can be utilized. Representative biodegradable cationic softeners/debonders are disclosed in U.S. Pat. Nos. 5,312,522; 5,415,737; 5,262,007; 5,264,082; and 5,223,096, all of which are incorporated herein by reference in their entirety. The compounds are biodegradable diesters of quaternary ammonia compounds, quaternized amine-esters, and biodegradable vegetable oil based esters functional with quaternary ammonium chloride and diester dierucyldimethyl ammonium chloride and are representative biodegradable softeners.

The surfactant is added in an amount of up to 8 lbs/ton, such as from 2 lbs/ton to 7 lbs/ton, such as from 4 lbs/ton to 7 lbs/ton such as from 6 lbs/ton to 7 lbs/ton.

The surface active agent may be added at any point prior to forming rolls, bales, or sheets of pulp. According to one embodiment, the surface active agent is added just prior to the headbox of the pulp machine, specifically at the inlet of the primary cleaner feed pump.

According to one embodiment, the fiber of the present invention has an improved filterability over the same fiber without the addition of surfactant when utilized in a viscose process. For example, the filterability of a viscose solution comprising fiber of the invention has a filterability that is at least 10% lower than a viscose solution made in the same way with the identical fiber without surfactant, such as at least 15% lower, such as at least 30% lower, such as at least 40% lower. Filterability of the viscose solution is measured by the following method. A solution is placed in a nitrogen pressurized (27 psi) vessel with a 1 and 3/16ths inch filtered orifice on the bottom—the filter media is as follows from outside to inside the vessel: a perforated metal disk, a 20 mesh stainless steel screen, muslin cloth, a Whatman 54 filter paper and a 2 layer knap flannel with the fuzzy side up toward the contents of the vessel. For 40 minutes the solution is allowed to filter through the media, then at 40 minutes for an additional 140 minutes the (so t=0 at 40 minutes) the volume of filtered solution is measured (weight) with the elapsed time as the X coordinate and the weight of filtered viscose as the Y coordinate—the slope of this plot is your filtration number. Recordings to be made at 10 minute intervals. The reference standard for comparison with the surfactant treated fiber is the identical fiber without the addition of surfactant.

According to one embodiment of the invention, the surfactant treated fiber of the invention exhibits a limited increase in specific absorption rate, e.g., less than 30% with a concurrent decrease in filterability, e.g., at least 10%. According to one embodiment, the surfactant treated fiber has an increased specific absorption rate of less than 30% and a decreased filterability of at least 20%, such as at least 30%, such as at least 40%. According to another embodiment, the surfactant treated fiber has an increased specific absorption rate of less than 25% and a decreased filterability of at least 10%, such as at least about 20%, such as at least 30%, such as at least 40%. According to yet another embodiment, the surfactant treated fiber has an increased specific absorption rate of less than 20% and a decreased filterability of at least 10%, such as at least about 20%, such as at least 30%, such as at least 40%. According to another embodiment, the surfactant treated fiber has an increased specific absorption rate of less than 15% and a decreased filterability of at least 10%, such as at least about 20%, such as at least 30%, such as at least 40%. According to still another embodiment, the surfactant treated fiber has an increased specific absorption rate of less than 10% and an decreased filterability of at least 10%, such as at least about 20%, such as at least 30%, such as at least 40%.

IV. Products Made from Kraft Fibers

The present disclosure provides products made from the modified kraft fiber described herein. In some embodiments, the products are those typically made from standard kraft fiber. In other embodiments, the products are those typically made from cotton linter or sulfite pulp. More specifically, modified fiber of the present invention can be used, without further modification, in the production of absorbent products and as a starting material in the preparation of chemical derivatives, such as ethers and esters. Heretofore, fiber has not been available which has been useful to replace both high alpha content cellulose, such as cotton and sulfite pulp, as well as traditional kraft fiber.

Phrases such as "which can be substituted for cotton linter (or sulfite pulp) . . . " and "interchangeable with cotton linter (or sulfite pulp) . . . " and "which can be used in place of cotton linter (or sulfite pulp) . . . " and the like mean only that the fiber has properties suitable for use in the end application normally made using cotton linter (or sulfite pulp). The phrase is not intended to mean that the fiber necessarily has all the same characteristics as cotton linter (or sulfite pulp).

In some embodiments, the products are absorbent products, including, but not limited to, medical devices, including wound care (e.g. bandage), baby diapers nursing pads, adult incontinence products, feminine hygiene products, including, for example, sanitary napkins and tampons, air-laid non-woven products, air-laid composites, "table-top" wipers, napkin, tissue, towel and the like. Absorbent products according to the present disclosure may be disposable. In those embodiments, modified fiber according to the invention can be used as a whole or partial substitute for the bleached hardwood or softwood fiber that is typically used in the production of these products.

In some embodiments, modified cellulose fiber is in the form of fluff pulp and has one or more properties that make the modified cellulose fiber more effective than conventional fluff pulps in absorbent products. More specifically, modified fiber of the present invention may have improved compressibility and improved odor control, both of which make it desirable as a substitute for currently available fluff pulp fiber. Because of the improved compressibility of the fiber of the present disclosure, it is useful in embodiments which seek to produce thinner, more compact absorbent structures. One skilled in the art, upon understanding the compressible nature of the fiber of the present disclosure, could readily envision absorbent products in which this fiber could be used. By way of example, in some embodiments, the disclosure provides an ultrathin hygiene product comprising the modified kraft fibers of the disclosure. Ultra-thin fluff cores are typically used in, for example, feminine hygiene products or baby diapers. Other products which could be produced with the fiber of the present disclosure could be anything requiring an absorbent core or a compressed absorbent layer. When compressed, fiber of the present invention exhibits no or no substantial loss of absorbency, but shows an improvement in flexibility.

According to one embodiment, the absorbent product may be a product, such as a diaper or incontinence device that will absorb and hold urine. Such devices generally contain an absorbent fluff core. The fibers of the present disclosure may be used to produce absorbent devices that can improve both urine wicking and retention thereby resulting in a more comfortable garment or device for the user.

Fibers of the present disclosure can improve vertical wicking, horizontal wicking, and/or 45 degree wicking. According to one embodiment, absorbent products made with fibers of the present disclosure improve vertical wicking over products made from fiber not subjected to an oxidation step by 10%. According to another embodiment, absorbent products made with fibers of the present disclosure improve vertical wicking over products made from fiber not subjected to an oxidation step by 15%. According to yet another embodiment, absorbent products made with fibers of the present disclosure improve vertical wicking over products made from fiber not subjected to an oxidation step by at least 20%. Similar improvements can be seen in horizontal and 45 degree wicking.

Fibers of the present disclosure can improve absorption rate and retention. According to one embodiment, absorbent products made with fibers of the present disclosure improve absorption rate over products made from fiber not subjected to an oxidation step by 10%. According to another embodiment, absorbent products made with fibers of the present disclosure improve absorption rate over products made from fiber not subjected to an oxidation step by 15%. According to yet another embodiment, absorbent products made with fibers of the present disclosure improve absorption rate over products made from fiber not subjected to an oxidation step by 20%. Similar improvements can be seen in horizontal and 45 degree wicking. Similarly, according to one embodiment, absorbent products made with fibers of the present disclosure improve total absorption over products made from fiber not subjected to an oxidation step by 5%. According to another embodiment, absorbent products made with fibers of the present disclosure improve total absorption over products made from fiber not subjected to an oxidation step by 10%. According to yet another embodiment, absorbent products made with fibers of the present disclosure improve total absorption over products made from fiber not subjected to an oxidation step by 15%.

The products as described when compared to products made with fibers not subjected to an oxidation step can exhibit improved flexibility (especially when used in the bending side of a multilayer core), improved dimensional stability after insult, and improved wet and dry strength (especially when placing the disclosed fiber in the top layer of a multilayer core) and elongation.

According to one embodiment, the absorbent core for use in an absorbent device can include one or more layers of fiber that have been treated differently to improve the overall uptake and retention of the device. As used herein, treated refers to any chemical or physical process that changes the absorbency, wicking or retention of the fiber. One common treatment is the addition of a surface active agent. According to one embodiment, the core can have a multitude of layers, for example, 2, 3, 4 or 5. According to one embodiment, fibers of the present invention can be used in any layer of a multi-layer absorbent core and be treated or untreated.

According to another embodiment, the fibers of the present invention are used in the top layer of the absorbent core. As used herein "top" refers to the place on the core that is first insulted with urine and closest to the skin. Likewise "bottom" refers to the layer farthest away from the user. Other layers may be referred to as "intermediate." The fibers of the present disclosure may be used either "untreated," which refers to fiber which has not been post-treated, for example, with a surfactant. The fibers may also be used in a "treated" state, which refers to fibers that have been modified by the inclusion of a surfactant. Treated or untreated fibers may be used in any layer and any combination.

According to one embodiment, fibers of the present invention are used in the top layer of an absorbent core. According to another embodiment, the fibers of the present invention are used in the bottom layer of an absorbent core. According to yet another embodiment, the fibers of the invention are used in the intermediate layer of the absorbent core.

In still another embodiment, fiber of the present disclosure is used in more than one layer of the absorbent core. The fiber of the present disclosure may be used in both the top and bottom layers of the absorbent core. Still further, the fiber of the present disclosure may be used in the top, bottom and intermediate layers of an absorbent core. According to one embodiment, the fibers in the top layer are treated fibers. According to another embodiment, the fibers in the bottom layer are treated fibers. According to yet another embodiment, the fibers in the intermediate layer are treated fibers.

The treated and untreated fibers of the present disclosure may be combined in a single layer or may be used in separate layers of the absorbent core. According to one embodiment, the top layer of the absorbent core comprises fiber of the disclosure that has not been treated and the bottom layer of the absorbent core comprises fiber of the disclosure that has been treated. According to another embodiment, the absorbent core is made with treated fibers of the disclosure in the top layer, untreated fibers of the disclosure in one or more intermediate layers and treated fibers of the disclosure in the bottom layer.

The density of the absorbent core may vary and will typically range from 0.10 g/cm$^3$ to 0.45 g/cm$^3$. According to one embodiment, the absorbent core may have a density of about 0.15 g/cm$^3$. According to another embodiment, the absorbent core may have a density of about 0.20 g/cm$^3$. According to yet another embodiment, the absorbent core may have a density of about 0.25 g/cm$^3$.

Modified fiber of the present invention may, without further modification, also be used in the production of absorbent products including, but not limited to, tissue, towel, napkin and other paper products which are formed on a traditional papermaking machine. Traditional papermaking processes involve the preparation of an aqueous fiber slurry which is typically deposited on a forming wire where the water is thereafter removed. The increased functionality of the modified cellulose fibers of the present disclosure may provide improved product characteristics in products including these modified fibers. For the reasons discussed above, the modified fiber of the present invention may cause the products made therewith to exhibit improvements in strength, likely associated with the increased functionality of the fibers. The modified fiber of the invention may also result in products having improved softness.

In some embodiments, the modified fiber of the present disclosure, without further modification, can be used in the manufacture of cellulose ethers (for example carboxymethylcellulose) and esters as a substitute for fiber with very high DP from about 2950 to about 3980 (i.e., fiber having a viscosity, as measured by 0.5% Capillary CED, ranging from about 30 mPa·s to about 60 mPa·s) and a very high percentage of cellulose (for example 95% or greater) such as those derived from cotton linters and from bleached softwood fibers produced by the acid sulfite pulping process. The modified fiber of the present invention which has not been subjected to acid hydrolysis will generally receive such an acid hydrolysis treatment in the production process for creating cellulose ethers or esters.

As described, the second and third types of fiber are produced through processes that derivatize or hydrolyze the fiber. These fibers can also be useful in the production of absorbent articles, absorbent paper products and cellulose derivatives including ethers and esters.

V. Acid/Alkaline Hydrolyzed Products

In some embodiments, this disclosure provides a modified kraft fiber that can be used as a substitute for cotton linter or sulfite pulp. In some embodiments, this disclosure provides a modified kraft fiber that can be used as a substitute for cotton linter or sulfite pulp, for example in the manufacture of cellulose ethers, cellulose acetates and microcrystalline cellulose.

Without being bound by theory, it is believed that the increase in aldehyde content relative to conventional kraft pulp provides additional active sites for etherification to end-products such as carboxymethylcellulose, methylcellulose, hydroxypropylcellulose, and the like, enabling production of a fiber that can be used for both papermaking and cellulose derivatives.

In some embodiments, the modified kraft fiber has chemical properties that make it suitable for the manufacture of cellulose ethers. Thus, the disclosure provides a cellulose ether derived from a modified kraft fiber as described. In some embodiments, the cellulose ether is chosen from ethylcellulose, methylcellulose, hydroxypropyl cellulose, carboxymethyl cellulose, hydroxypropyl methylcellulose, and hydroxyethyl methyl cellulose. It is believed that the cellulose ethers of the disclosure may be used in any application where cellulose ethers are traditionally used. For example, and not by way of limitation, the cellulose ethers of the disclosure may be used in coatings, inks, binders, controlled release drug tablets, and films.

In some embodiments, the modified kraft fiber has chemical properties that make it suitable for the manufacture of cellulose esters. Thus, the disclosure provides a cellulose ester, such as a cellulose acetate, derived from modified kraft fibers of the disclosure. In some embodiments, the disclosure provides a product comprising a cellulose acetate derived from the modified kraft fiber of the disclosure. For example, and not by way of limitation, the cellulose esters of the disclosure may be used in, home furnishings, cigarettes, inks, absorbent products, medical devices, and plastics including, for example, LCD and plasma screens and windshields.

In some embodiments, the modified kraft fiber has chemical properties that make it suitable for the manufacture of microcrystalline cellulose. Microcrystalline cellulose production requires relatively clean, highly purified starting cellulosic material. As such, traditionally, expensive sulfite pulps have been predominantly used for its production. The present disclosure provides microcrystalline cellulose derived from modified kraft fiber of the disclosure. Thus, the disclosure provides a cost-effective cellulose source for microcrystalline cellulose production. In some embodiments, the microcrystalline cellulose is derived from modified kraft fiber having a DP which is less than about 100, for example, less than about 75 or less than about 50. In some embodiments, the microcrystalline cellulose is derived from modified kraft fiber having an R10 value ranging from about 65% to about 85%, for instance from about 70% to about 85%, or from about 75% to about 85% and an R18 value ranging from about 75% to about 90%, for instance from about 80% to about 90%, for example from about 80% to about 87%.

The modified cellulose of the disclosure may be used in any application that microcrystalline cellulose has traditionally been used. For example, and not by way of limitation, the modified cellulose of the disclosure may be used in pharmaceutical or nutraceutical applications, food applications, cosmetic applications, paper applications, or as a structural composite. For instance, the modified cellulose of the disclosure may be a binder, diluent, disintegrant, lubricant, tabletting aid, stabilizer, texturizing agent, fat replacer, bulking agent, anticaking agent, foaming agent, emulsifier, thickener, separating agent, gelling agent, carrier material, opacifier, or viscosity modifier. In some embodiments, the microcrystalline cellulose is a colloid VI. Products Comprising Acid Hydrolyzed Products In some embodiments, the disclosure provides a pharmaceutical product comprising a microcrystalline cellulose that has been produced from a modified kraft fiber of the disclosure that has been hydrolyzed. The pharmaceutical product may be any pharmaceutical product in which microcrystalline cellulose has traditionally been used. For example, and not by way of limitation, the pharmaceutical product may be chosen from tablets and capsules. For instance, the microcrystalline cellulose of the present disclosure may be a diluent, a disintegrant, a binder, a compression aid, coating and/or a lubricant. In other embodiments, the disclosure provides a pharmaceutical product comprising at least one modified derivatized kraft fiber of the disclosure, such as a hydrolyzed modified kraft fiber.

In some embodiments, the disclosure provides a food product comprising a bleached kraft fiber of the disclosure that has been hydrolyzed. In some embodiments, the disclosure provides a food product comprising at least one product derived from bleached kraft fiber of the disclosure. In further embodiments, the disclosure provides a food product comprising microcrystalline cellulose derived from kraft fibers of the disclosure. In some embodiments, the food product comprises colloidal microcrystalline cellulose derived from kraft fibers of the disclosure. The food product may be any food product in which microcrystalline cellulose has traditionally been used. Exemplary food categories in which microcrystalline cellulose may be used are well known to those of ordinary skill in the art, and can be found, for example, in the Codex Alimentarius, for instance at Table 3. For instance, microcrystalline cellulose derived from chemically modified kraft fibers of the disclosure may be an anticaking agent, bulking agent, emulsifier, foaming agent, stabilizer, thickener, gelling agent, and/or suspension agent.

Other products comprising cellulose derivatives and microcrystalline cellulose derived from chemically modified kraft fibers according to the disclosure may also be envisaged by persons of ordinary skill in the art. Such products may be found, for example, in cosmetic and industrial applications.

As used herein, "about" is meant to account for variations due to experimental error. All measurements are understood to be modified by the word "about", whether or not "about" is explicitly recited, unless specifically stated otherwise.

Thus, for example, the statement "a fiber having a length of 2 mm" is understood to mean "a fiber having a length of about 2 mm."

The details of one or more non-limiting embodiments of the invention are set forth in the examples below. Other embodiments of the invention should be apparent to those of ordinary skill in the art after consideration of the present disclosure.

EXAMPLES

A. Test Protocols
1. Caustic solubility (R10, S10, R18, S18) is measured according to TAPPI T235-cm00.
2. Carboxyl content is measured according to TAPPI T237-cm98.
3. Aldehyde content is measured according to Econotech Services LTD, proprietary procedure ESM 055B.
4. Copper Number is measured according to TAPPI T430-cm99.
5. Carbonyl content is calculated from Copper Number according to the formula: carbonyl=(Cu. No.−0.07)/0.6, from *Biomacromolecules* 2002, 3, 969-975.
6. 0.5% Capillary CED Viscosity is measured according to TAPPI T230-om99.
7. Intrinsic Viscosity is measured according to ASTM D1795 (2007).
8. DP is calculated from 0.5% Capillary CED Viscosity according to the formula: $DPw=-449.6+598.4 \ln(0.5\%$ Capillary CED$)+118.02 \ln^2 (0.5\%$ Capillary CED$)$, from the 1994 Cellucon Conference published in *The Chemistry and Processing Of Wood And Plant Fibrous Materials*, p. 155, Woodhead Publishing Ltd, Abington Hall, Abington, Cambridge CBI 6AH, England, J. F. Kennedy, et al. editors.
9. Carbohydrates are measured according to TAPPI T249-cm00 with analysis by Dionex ion chromatography.
10. Cellulose content is calculated from carbohydrate composition according to the formula: Cellulose=Glucan−(Mannan/3), from *TAPPI Journal* 65(12):78-80 1982.
11. Hemicellulose content is calculated from the sum of sugars minus the cellulose content.
12. Fiber length and coarseness is determined on a Fiber Quality Analyzer™ from OPTEST, Hawkesbury, Ontario, according to the manufacturer's standard procedures.
13. Wet Zero Span Tensile is determined according to TAPPI T273-pm99.
14. Freeness is determined according to TAPPI T227-om99.
15. Water Retention Value is determined according to TAPPI UM 256.
16. DCM (dichloromethane) extractives are determined according to TAPPI T204-cm97.
17. Iron content is determined by acid digestion and analysis by ICP.
18. Ash content is determined according to TAPPI T211-om02.
19. Peroxide residual is determined according to Interox procedure.
20. Brightness is determined according to TAPPI T525-om02.
21. Porosity is determined according to TAPPI 460-om02.
22. Burst factor is determined according to TAPPI T403-om02.
23. Tear factor is determined according to TAPPI T414-om98.
24. Breaking length and stretch are determined according to TAPPI T494-om01.
25. Opacity is determined according to TAPPI T425-om01.
26. Frazier porosity is determined on a Frazier Low Air Permeability Instrument from Frazier Instruments, Hagerstown, Md., according to the manufacturer's procedures.
27. Fiber Length and shape factor are determined on an L&W Fiber Tester from Lorentzen & Wettre, Kista, Sweden, according to the manufacturer's standard procedures.
28. Dirt and shives are determined according to TAPPI T213-om01

B. Exemplary Method for Making Modified Cellulose Fiber

A semi-bleached or mostly bleached kraft pulp may be treated with an acid, iron and hydrogen peroxide for the purposes of reducing the fiber's viscosity or DP. The fiber may be adjusted to a pH of from about 2 to about 5 (if not already in this range) with sulfuric, hydrochloric, acetic acid, or filtrate from the washer of an acidic bleach stage, such as a chlorine dioxide stage. Iron may be added in the form of $Fe^{+2}$, for example iron may be added as ferrous sulfate heptahydrate ($FeSO_4.7H_2O$). The ferrous sulfate may be dissolved in water at a concentration ranging from about 0.1 to about 48.5 g/L. The ferrous sulfate solution may be added at an application rate ranging from about 25 to about 200 ppm as $Fe^{+2}$ based on the dry weight of pulp. The ferrous sulfate solution may then be mixed thoroughly with the pH-adjusted pulp at a consistency of from about 1% to about 15% measured as dry pulp content of the total wet pulp mass. Hydrogen peroxide ($H_2O_2$) may then be added as a solution with a concentration of from about 1% to about 50% by weight of $H_2O_2$ in water, at an amount of from about 0.1% to about 3% based on the dry weight of the pulp. The pulp at a pH of from about 2 to about 5 mixed with the ferrous sulfate and peroxide may be allowed to react for a time ranging from about 40 to about 80 minutes at a temperature of from about 60 to about 80 degrees C. The degree of viscosity (or DP) reduction is dependent on the amount of peroxide consumed in the reaction, which is a function of the concentration and amount of peroxide and iron applied and the retention time and temperature.

The treatment may be accomplished in a typical five-stage bleach plant with the standard sequence of $D_0$ E1 D1E2 D2. With that scheme, no additional tanks, pumps, mixers, towers, or washers are required. The fourth or E2 stage may be preferably used for the treatment. The fiber on the D1 stage washer may be adjusted to a pH of from about 2 to about 5, as needed by addition of acid or of filtrate from the D2 stage. A ferrous sulfate solution may be added to the pulp either (1) by spraying it on the D1 stage washer mat through the existing shower headers or a new header, (2) added through a spray mechanism at the repulper, or (3) added through an addition point before a mixer or pump for the fourth stage. The peroxide as a solution may be added following the ferrous sulfate at an addition point in a mixer or pump before the fourth stage tower. Steam may also be added as needed before the tower in a steam mixer. The pulp may then be reacted in the tower for an appropriate retention time. The chemically modified pulp may then be washed on the fourth stage washer in a normal fashion. Additional bleaching may be optionally accomplished following the treatment by the fifth or D2 stage operated in a normal fashion.

Example 1

Methods of Preparing Fibers of the Disclosure
A. Mill Method A

Southern pine cellulose was digested and oxygen delignified in a conventional two-stage oxygen delignification step to a kappa number of from about 9 to about 10. The delignified pulp was bleached in a five-stage bleach plant, with a sequence of $D_0(EO)D1E2D2$. Before the fourth or E2 stage, the pH of the pulp was adjusted to a range of from about 2 to about 5 with filtrate from a D stage of the sequence. After the pH was adjusted, 0.2% hydrogen peroxide based on the dry weight of the pulp and 25 ppm $Fe^{+2}$ in the form of $FeSO_4 \cdot 7H_2O$ based on the dry weight of the pulp were added to the kraft fibers in the E2 stage tower and reacted for about 90 minutes at a temperature of from about 78 to about 82 degrees C. The reacted fibers were then washed on the fourth stage washer, and then bleached with chlorine dioxide in the fifth (D2) stage.

B. Mill Method B

Fibers were prepared as described in Mill Method A, except that the pulp was treated with 0.6% peroxide and 75 ppm $Fe^{+2}$.

C. Mill Method C

Fibers were prepared as described in Mill Method A, except that the pulp was treated with 1.4% peroxide and 100 ppm $Fe^{+2}$.

Properties of Exemplary Fibers

Samples of fibers prepared according to Mill Methods A (sample 2), B (sample 3), and C (sample 4) were collected following the five-stage bleaching sequence described above. Several properties of these samples along with a standard fluff grade fiber (GP Leaf River Cellulose, New Augusta, Miss.; Sample 1), and a commercially available sample (PEACH™, sold by Weyerhaeuser Co.; Sample 5), were measured according to the protocols described above. The results of these measurements are reported in Table 1 below.

TABLE 1

| Fiber Measurement | | Sample 1 GP Leaf River Cellulose, fluff grade fiber | Sample 2 Mill Method A | Sample 3 Mill Method B | Sample 4 Mill Method C | Sample 5 Weyerhaeuser Co. PEACH |
|---|---|---|---|---|---|---|
| R10 | % | 86.8 | 85.2 | 82.4 | 72.5 | 78.4 |
| S10 | % | 13.2 | 14.8 | 17.6 | 27.5 | 21.6 |
| R18 | % | 87.0 | 87.2 | 85.4 | 78.7 | 84.4 |
| S18 | % | 13.0 | 12.8 | 14.6 | 21.3 | 15.6 |
| ΔR | | 0.2 | 2.0 | 3.0 | 6.2 | 6.0 |
| Carboxyl | meq/100 g | 3.13 | 3.53 | 3.70 | 3.94 | 3.74 |
| Aldehydes | meq/100 g | 0.97 | 1.24 | 2.15 | 4.21 | 0.87 |
| Copper No. | | 0.51 | 1.2 | 1.3 | 4.25 | 1.9 |
| Calculated Carbonyl | mmole/100 g | 0.73 | 1.88 | 2.05 | 6.97 | 3.05 |
| Calculated carbonyl/Aldehyde ratio | | 0.75 | 1.52 | 0.95 | 1.66 | 3.5 |
| 0.5% Capillary CED Viscosity | mPa · s | 15.0 | 8.9 | 6.5 | 3.50 | 4.16 |
| Intrinsic Viscosity | [η] dl/g | 7.14 | 5.44 | 4.33 | 2.49 | 3.00 |
| Calculated DP | $DP_w$ | 2036 | 1423 | 1084 | 485 | 643 |
| Glucan | % | 83.0 | 85.9 | 84.6 | 85.4 | 82 |
| Xylan | % | 9.0 | 8.8 | 9.4 | 8.2 | 8.4 |
| Galactan | % | 0.2 | 0.2 | 0.2 | 0.2 | 0.2 |
| Mannan | % | 5.9 | 5.4 | 5.3 | 5.5 | 6.2 |
| Arabinan | % | 0.4 | 0.3 | 0.3 | 0.4 | 0.3 |
| Calculated Cellulose | % | 81.0 | 84.1 | 82.8 | 83.6 | 79.9 |
| Calculated Hemicellulose | % | 17.5 | 16.5 | 17.0 | 16.1 | 17.2 |
| Lwl Fiber Length | mm | 2.34 | 2.57 | 2.53 | 2.30 | 2.19 |
| Lww Fiber Length | mm | 3.39 | 3.34 | 3.34 | | 3.01 |
| Coarseness | | | 0.222 | 0.234 | 0.19 | 0.254 |
| Wet Zero Span Breaking Length | km | 9.38 | | 6.83 | 5.01 | 2.3 |
| DCM extractives | | | 0.006 | 0.006 | | |
| Iron | ppm | | 5.5 | 4.4 | | |
| WRV | | | 0.98 | 0.99 | | 0.85 |
| Brightness | % ISO | 89.6 | 89.0 | 88.2 | 88.5 | 88.5 |

As reported in Table 1, iron content of the control fiber, Sample 1, was not measured. However, the iron content of four mill-made pulp samples treated under the same conditions as those reported for Sample 1 were taken. The iron content of those samples averaged 2.6 ppm. Accordingly, for Sample 1, one would expect the iron content to be on the order of about 2.5 ppm.

As can be seen from Table 1, modified fiber according to the present invention is unexpectedly different from both the control fiber, Sample 1, and an alternative commercially available oxidized fiber, Sample 5, in the total carbonyl content as well as the carboxyl content and aldehyde content. To the extent there is a difference between the total carbonyl groups and aldehyde groups, additional carbonyl functionality may be in the form of other ketones. The data shows that we achieve relatively high levels of aldehydes while retaining carboxylic acid groups and while retaining a near unity ratio of aldehydes to total carbonyl groups (as seen in Table 1, about 1.0 (0.95) to 1.6). This is more surprising in a fiber that exhibits high brightness and that is also relatively strong and absorbent.

As can be seen in Table 1, the standard fluff grade fiber (Sample 1) had a carboxyl content of 3.13 meq/100 g, and an aldehyde content of 0.97 meq/100 g. After a low-dose treatment with 0.2% $H_2O_2$ and 25 ppm $Fe^{+2}$ (Sample 2) or a higher-dose treatment with 0.6% $H_2O_2$ and 75 ppm $Fe^{+2}$ (Sample 3), or a higher-dose treatment with 1.4% $H_2O_2$ and 100 ppm $Fe^{+2}$ (Sample 4), the fiber length and calculated cellulose content were relatively unchanged, and fiber strength as measured by the wet zero span method was diminished somewhat, yet the carboxyl, carbonyl, and aldehyde contents were all elevated, indicating extensive oxidation of the cellulose.

In comparison, a commercially available sample of oxidized kraft softwood southern pine fiber manufactured by an alternative method (Sample 5), shows significant reduction in fiber length and about a 70 percent loss in fiber strength as measured by the wet zero span method as compared to the fluff grade fiber reported as Sample 1. The aldehyde content of Sample 5 was virtually unchanged compared to the standard fluff grade fibers, while the inventive fibers prepared by mill methods A-C (Samples 2-4) had highly elevated aldehyde levels representing from about 70 to about 100 percent of the total calculated carbonyl content of the cellulose. In contrast, the PEACH® aldehyde level was less than 30 percent of the total calculated carbonyl content of the cellulose. The ratio of total carbonyl to aldehyde would appear to be a good indicator of a fiber that has the broad applicability of the modified fibers within the scope of this disclosure, particularly if the ratio is in the range of about 1 to about 2, as are Samples 2-4. Low viscosity fibers, such as Samples 3 and 4, and with carbonyl/aldehyde ratios of about 1.5 to less than 2.0, maintained fiber length, while those of the comparative Sample 5 did not.

The freeness, density, and strength of the standard fiber described above (Sample 1) were compared with Sample 3 described above. The results of this analysis are depicted in Table 2.

TABLE 2

Pulp, Paper & Fiber Properties of Standard & Modified Kraft Fiber

| | PFI refining revs | Freeness (CSF) | Density g/cm³ | Breaking Length km | Wet Zero Span Breaking Length km |
|---|---|---|---|---|---|
| Standard Leaf River Fluff having 0.5% Capillary CED viscosity of about 15 mPa · s (Sample 1) | 0 | 737 | 0.538 | 2.16 | 9.38 |
| | 300 | 721 | 0.589 | 3.57 | |
| Modified cellulose fiber as in (ULDP) having 0.5% Capillary CED viscosity 6.5 mPa · s (Sample 3) | 0 | 742 | 0.544 | 2.19 | 6.83 |
| | 300 | 702 | 0.595 | 3.75 | |

As can be seen in the above Table 2, the modified cellulose fibers according to this disclosure may have a freeness comparable to standard fluff fibers that have not undergone an oxidation treatment in the bleaching sequence.

Example 2

A sample of Southern pine pulp from the D1 stage of a OD(EOP)D(EP)D bleach plant with a 0.5% Capillary CED viscosity of about 14.6 mPa·s was treated at about 10% consistency with hydrogen peroxide applications of from 0.25% to 1.5% and either 50 or 100 ppm of $Fe^{+2}$ added as $FeSO_4 \cdot 7H_2O$. The $Fe^{+2}$ was added as a solution in water and mixed thoroughly with the pulp. The hydrogen peroxide as a 3% solution in water was then mixed with the pulp. The mixed pulp was held in a water bath for 1 hour at 78° C. After the reaction time, the pulp was filtered and the filtrate measured for pH and residual peroxide. The pulp was washed and the 0.5% Capillary CED viscosity determined according to TAPPI T230. The results are shown in Table 3.

TABLE 3

| $H_2O_2$ added % on pulp | $H_2O_2$ consumed % on pulp | $Fe^{+2}$ ppm on pulp | pH final | 0.5% Capillary CED Viscosity mPa · s | ΔViscosity | DPw |
|---|---|---|---|---|---|---|
| Control | | | | 14.6 | | 2003 |
| 0.25 | 0.25 | 100 | 4.8 | 8.6 | 6.0 | 1384 |
| 0.50 | 0.34 | 50 | 4.7 | 8.9 | 5.7 | 1423 |
| 0.50 | 0.50 | 100 | 4.8 | 6.8 | 7.8 | 1131 |
| 0.75 | 0.19 | 50 | 4.6 | 10.6 | 4.0 | 1621 |
| 0.75 | 0.75 | 100 | 4.7 | 5.8 | 8.8 | 967 |
| 1.0 | 0.20 | 50 | 4.6 | 9.0 | 5.6 | 1435 |
| 1.0 | 0.40 | 100 | 4.7 | 7.8 | 6.8 | 1278 |
| 1.5 | 0.30 | 50 | 4.6 | 10.0 | 4.6 | 1554 |
| 1.5 | 0.40 | 100 | 4.6 | 7.5 | 7.1 | 1235 |

Example 3

A sample of D1 pulp from the bleach plant described in Example 2, with a 0.5% Capillary CED viscosity of 15.8 mPa·s (DPw 2101) was treated with 0.75% hydrogen peroxide applied and $Fe^{+2}$ was added from 50 to 200 ppm in the same manner as Example 2, except the retention times were also varied from 45 to 80 minutes. The results are shown in Table 4.

TABLE 4

| Treatment time minutes | $H_2O_2$ added % on pulp | $H_2O_2$ consumed % on pulp | $Fe^{+2}$ ppm on pulp | pH final | 0.5% Capillary CED Viscosity mPa · s | ΔViscosity | DPw 2101 |
|---|---|---|---|---|---|---|---|
| Control | | | | | 15.8 | | 1291 |
| 45 | 0.75 | 0.72 | 100 | 4.4 | 7.9 | 7.9 | 1035 |
| 60 | 0.75 | 0.75 | 200 | 4.1 | 6.2 | 9.6 | 1384 |
| 80 | 0.75 | 0.27 | 50 | | 8.6 | 7.2 | 1018 |
| 80 | 0.75 | 0.75 | 100 | 4.6 | 6.1 | 9.7 | 2101 |

Example 4

A sample of D1 pulp from the bleach plant described in Example 2, with a 0.5% Capillary CED viscosity of 14.8 mPa·s (DPw 2020) was treated with 0.75% hydrogen peroxide and 150 ppm of $Fe^{+2}$ in the same manner as described in Example 2, except that the treatment time was 80 minutes. The results are shown in Table 5.

TABLE 5

| Treatment time minutes | $H_2O_2$ added % on pulp | $H_2O_2$ consumed % on pulp | $Fe^{+2}$ ppm on pulp | pH final | 0.5% Capillary CED Viscosity mPa · s | ΔViscosity | DPw |
|---|---|---|---|---|---|---|---|
| Control | | | | | 14.8 | | 2020 |
| 80 | 0.75 | 0.75 | 150 | 3.9 | 5.2 | 9.6 | 858 |

Example 5

A Southern pine pulp from the D1 stage of a $OD_0(E0)D1(EP)D2$ sequence with a 0.5% Capillary CED viscosity of 15.6 mPa·s (DPw 2085) was treated at 10% consistency with hydrogen peroxide applications of either 0.25% or 0.5% by weight on pulp and 25, 50, or 100 ppm of $Fe^{+2}$ added as $FeSO_4 \cdot 7H_2O$. The $Fe^{+2}$ was added as a solution in water and mixed thoroughly with the pulp. The hydrogen peroxide was a 3% solution in water that was then mixed with the pulp, and the mixed pulp was held in a water bath for 1 hour at 78° C. After the reaction time, the pulp was filtered and the filtrate measured for pH and residual peroxide. The pulp was washed and the 0.5% Capillary CED viscosity determined according to TAPPI T230. The results are shown in Table 6.

TABLE 6

| $H_2O_2$ added % on pulp | $H_2O_2$ consumed % on pulp | $Fe^{+2}$ ppm on pulp | pH final | 0.5% Capillary CED Viscosity mPa·s | ΔViscosity | DPw |
|---|---|---|---|---|---|---|
| Control | | | | 15.6 | | 2085 |
| 0.25 | 0.25 | 25 | 3.5 | 6.4 | 9.2 | 1068 |
| 0.50 | 0.50 | 50 | 2.9 | 4.5 | 11.1 | 717 |
| 0.50 | 0.50 | 100 | 2.7 | 4.5 | 11.1 | 717 |

Example 6

Another sample of D1 pulp, with a 0.5% Capillary CED viscosity of 15.2 mPa·s (DPw 2053) was treated with 0.10, 0.25, 0.50, or 0.65% hydrogen peroxide and 25, 50, or 75 ppm of $Fe^{+2}$ in the same manner as Example 5. The results are shown in Table 7.

TABLE 7

| Treatment time minutes | $H_2O_2$ added % on pulp | $H_2O_2$ consumed % on pulp | $Fe^{+2}$ ppm on pulp | pH final | 0.5% Capillary CED Viscosity mPa·s | ΔViscosity | DPw |
|---|---|---|---|---|---|---|---|
| Control | | | | | 15.2 | | 2053 |
| 60 | 0.10 | 0.10 | 25 | 4.1 | 9.6 | 5.6 | 1508 |
| 60 | 0.25 | 0.19 | 25 | 4.0 | 7.9 | 7.3 | 1291 |
| 60 | 0.50 | 0.40 | 50 | 3.5 | 6.7 | 8.5 | 1116 |
| 80 | 0.65 | 0.65 | 75 | 3.3 | 4.4 | 10.8 | 696 |

Example 7

A Southern pine pulp was collected from the D1 stage of a OD(EO)D(EP)D bleaching sequence, after the extent of delignification in the kraft and oxygen stages was increased to produce a pulp with a lower DPw or 0.5% Capillary CED viscosity. The starting 0.5% Capillary CED viscosity was 12.7 mPa·s (DPw 1834). Either 0.50 or 1.0% hydrogen peroxide was added with 100 ppm of $Fe^{+2}$. Other treatment conditions were 10% consistency, 78° C., and 1 hour treatment time. The results are shown in Table 8.

TABLE 8

| $H_2O_2$ added % on pulp | $H_2O_2$ consumed % on pulp | $Fe^{+2}$ ppm on pulp | pH final | 0.5% Capillary CED Viscosity mPa·s | ΔViscosity | DPw |
|---|---|---|---|---|---|---|
| Control | | | | 12.7 | | 1834 |
| 0.50 | 0.50 | 100 | 2.1 | 5.6 | 7.1 | 932 |
| 1.0 | 0.37 | 100 | 2.6 | 4.2 | 8.5 | 652 |

Example 8

A low viscosity sample of D1 pulp from the D1 stage of a OD(EO)D(EP)D sequence, with a 0.5% Capillary CED viscosity of 11.5 mPa·s (DPw 1716), was treated with either 0.75 or 1.0% hydrogen peroxide and 75 or 150 ppm of $Fe^{+2}$ in a manner similar to Example 7, except the treatment time was 80 minutes. The results are shown in Table 9.

TABLE 9

| $H_2O_2$ added % on pulp | $H_2O_2$ consumed % on pulp | $Fe^{+2}$ ppm on pulp | pH final | 0.5% Capillary CED Viscosity mPa·s | ΔViscosity | DPw |
|---|---|---|---|---|---|---|
| Control | | | | 11.5 | | 1716 |
| 0.75 | 0.75 | 75 | 3.2 | 3.6 | 7.9 | 511 |
| 0.75 | 0.75 | 150 | 3.0 | 3.8 | 7.7 | 560 |
| 1 | 1 | 75 | 2.6 | 3.4 | 8.1 | 459 |
| 1 | 1 | 150 | 2.6 | 3.4 | 8.1 | 459 |

Example 9

A Southern pine pulp was collected from the D1 stage of a OD(EO)D(EP)D sequence. The starting 0.5% Capillary CED viscosity was 11.6 mPa·s (DPw 1726). Either 1.0%, 1.5%, or 2% hydrogen peroxide was added with 75, 150, or 200 ppm of $Fe^{+2}$. Other treatment conditions were 10% consistency, 78° C., and 1.5 hour treatment time. The results are shown in Table 10.

TABLE 10

| $H_2O_2$ added % on pulp | $H_2O_2$ consumed % on pulp | $Fe^{+2}$ ppm on pulp | pH final | 0.5% Capillary CED Viscosity mPa·s | ΔViscosity | DPw | Carboxyl meq/ 100 g | Aldehyde meq/ 100 g | Copper no. |
|---|---|---|---|---|---|---|---|---|---|
| Control | | | | 11.6 | | 1726 | 3.67 | 0.35 | 0.52 |
| 1.0 | 0.98 | 75 | 3.4 | 3.5 | 8.1 | 485 | 3.73 | 4.06 | 3.05 |
| 1.5 | 1.49 | 150 | 2.7 | 3.2 | 8.4 | 406 | 3.78 | 5.06 | 2.57 |
| 2.0 | 2.0 | 200 | 2.9 | 3.0 | 8.6 | 350 | 3.67 | 5.23 | 2.06 |

Example 10

A Southern pine pulp was collected from the D1 stage of a OD(EO)D(EP)D sequence. The starting 0.5% Capillary CED viscosity was 14.4 mPa·s (DPw 1986). Either 1.0%, 1.5%, or 2% hydrogen peroxide was added with 75, 150, or 200 ppm of $Fe^{+2}$. Other treatment conditions were 10% consistency, 78° C., and 1.5 hour reaction time. The results are shown in Table 11.

TABLE 11

| $H_2O_2$ added % on pulp | $H_2O_2$ consumed % on pulp | $Fe^{+2}$ ppm on pulp | pH final | 0.5% Capillary CED Viscosity mPa·s | ΔViscosity | DPw | Carboxyl meq/100 g | Aldehyde meq/100 g | Copper no. |
|---|---|---|---|---|---|---|---|---|---|
| Control | | | | 14.4 | | 1986 | 3.52 | 0.23 | 0.67 |
| 1.0 | 0.95 | 75 | 3.3 | 3.8 | 10.6 | 560 | 3.65 | 3.48 | 2.47 |
| 1.5 | 1.5 | 150 | 2.4 | 3.7 | 10.7 | 535 | 4.13 | 4.70 | 2.32 |
| 2.0 | 2.0 | 200 | 2.8 | 3.2 | 11.2 | 406 | 3.93 | 5.91 | 1.88 |

Example 11

A Southern pine pulp was collected from the D1 stage of a OD(EO)D(EP)D sequence. The starting 0.5% Capillary CED viscosity was 15.3 mPa·s (DPw 2061). Hydrogen peroxide was added at 3% on pulp with 200 ppm of $Fe^{+2}$. Other treatment conditions were 10% consistency, 80° C., and 1.5 hour reaction time. The results are shown in Table 12.

TABLE 12

| $H_2O_2$ added % on pulp | $H_2O_2$ consumed % on pulp | $Fe^{+2}$ ppm on pulp | pH final | 0.5% Capillary CED Viscosity mPa·s | ΔViscosity | DPw | Carboxyl meq/100 g | Aldehyde meq/100 g | Copper no. |
|---|---|---|---|---|---|---|---|---|---|
| Control | | | | 15.3 | | 2061 | | | |
| 3.0 | 2.9 | 200 | 2.8 | 2.94 | 12.4 | 333 | 4.66 | 6.74 | 5.14 |

The above Examples 2-11 show that a significant decrease in 0.5% Capillary CED viscosity and/or degree of polymerization can be achieved with the acidic, catalyzed, peroxide treatment of the present disclosure. The final viscosity or DPw appears to be dependent on the amount of peroxide that is consumed by the reaction, as shown in FIG. 1, which reports the viscosity of pulp from two different mills ("Brunswick" and Leaf River ("LR")) as a function of the percent peroxide consumed. The peroxide consumption is a function of the amounts and concentrations of peroxide and iron applied, the reaction time, and the reaction temperature.

Example 12

A Southern pine pulp was collected from the D1 stage of a OD(EO)D(EP)D sequence. The starting 0.5% Capillary CED viscosity was 14.8 mPa·s (DPw 2020). Hydrogen peroxide was added at 1% on pulp with either 100, 150, or 200 pm of $Cu^{+2}$ added as $CuSO_4.5H_2O$. Other treatment conditions were 10% consistency, 80° C., and 3.5 hours reaction time. The results are shown in Table 13.

The use of copper instead of iron resulted in a slower reaction and a lower reduction in viscosity, but still a significant change in viscosity, carboxyl content, and aldehyde content over the control, untreated pulp.

Example 13

The E2 (EP) stage of an OD(EOP)D(EP)D sequence was altered to produce the ultra low degree of polymerization pulp. A solution of $FeSO_4.7H_2O$ was sprayed on the pulp at the washer repulper of the D1 stage at an application rate of 150 ppm as $Fe^{+2}$. No caustic (NaOH) was added to the E2 stage and the peroxide application was increased to 0.75%. The retention time was approximately 1 hour and the temperature was 79° C. The pH was 2.9. The treated pulp was washed on a vacuum drum washer and subsequently treated in the final D2 stage with 0.7% $ClO_2$ for approximately 2 hours at 91° C. The 0.5% Capillary CED viscosity of the final bleached pulp was 6.5 mPa·s (DPw 1084) and the ISO brightness was 87.

Example 14

The pulp produced in Example 13 was made into a pulp board on a Fourdrinier type pulp dryer with standard dryer cans. Samples of a control pulp and the pulp of the present invention (ULDP) were collected and analyzed for chemical composition and fiber properties. The results are shown in Table 14.

TABLE 14

| Property | | Standard | ULDP |
|---|---|---|---|
| R10 | % | 85.2 | 81.5 |
| S10 | % | 14.8 | 18.5 |
| R18 | % | 86.4 | 84.4 |

TABLE 13

| $H_2O_2$ added % on pulp | $H_2O_2$ consumed % on pulp | $Cu^{+2}$ ppm on pulp | pH final | 0.5% Capillary CED Viscosity mPa·s | ΔViscosity | Dpw | Carboxyl meq/100 g | Aldehyde meq/100 g | Copper no. |
|---|---|---|---|---|---|---|---|---|---|
| Control | | | | 14.8 | | 2020 | 3.36 | 0.37 | 0.51 |
| 1.0 | 0.82 | 100 | 2.4 | 6.1 | 8.7 | 1018 | | | |
| 1.0 | 0.94 | 150 | 2.3 | 5.9 | 8.9 | 984 | | | |
| 1.0 | 0.94 | 200 | 2.4 | 6.0 | 8.8 | 1001 | 3.37 | 2.71 | 1.8 |

TABLE 14-continued

| Property | | Standard | ULDP |
|---|---|---|---|
| S18 | % | 13.6 | 15.6 |
| ΔR | | 1.2 | 2.9 |
| Carboxyl | meq/100 g | 4.06 | 4.27 |
| Aldehydes | meq/100 g | 0.43 | 1.34 |
| Copper No. | | 0.32 | 1.57 |
| Calculated Carbonyl | mmole/100 g | 0.42 | 2.50 |
| 0.5% Capillary CED Viscosity | mPa · s | 14.2 | 7.3 |
| Intrinsic Viscosity | dl/g | 6.76 | 4.37 |
| Calculated DP | $DP_w$ | 1969 | 1206 |
| Glucan | % | 83.6 | 83.6 |
| Xylan | % | 9.2 | 9.0 |
| Galactan | % | 0.2 | 0.2 |
| Mannan | % | 6.3 | 6.4 |
| Arabinan | % | 0.4 | 0.4 |
| Calculated Cellulose | % | 81.5 | 81.5 |
| Calculated Hemicellulose | % | 18.2 | 18.1 |
| Lwl Fiber Length | mm | 2.51 | 2.53 |
| Lww Fiber Length | mm | 3.28 | 3.26 |
| Coarseness | mg/m | 0.218 | 0.213 |
| Wet Zero Span Tensile | km | 9.86 | 6.99 |
| Freeness (CSF) | mls | 720 | 742 |
| Water Retention Value | g $H_2O$/g pulp | 0.96 | 0.84 |
| DCM extractives | | 0.008 | 0.007 |
| Iron | ppm | 3.5 | 10.7 |
| Ash | % | 0.20 | 0.22 |
| Brightness | % ISO | 90.4 | 86.5 |

The treated pulp (ULDP) had a higher alkali solubility in 10% and 18% NaOH and a higher aldehyde and total carbonyl content. The ULDP was significantly lower in DP as measured by 0.5% Capillary CED viscosity. The decrease in fiber integrity was also determined by a reduction in wet zero span tensile strength. Despite the significant reduction in DPw, the fiber length and freeness were essentially unchanged. There were no deleterious effects on drainage or board making on the machine.

Example 15

The E2 (EP) stage of a OD(EO)D(EP)D sequence was altered to produce the ultra low degree of polymerization pulp in a similar manner as Example 13. In this example, the $FeSO_4.7H_2O$ was added at 75 ppm as $Fe^{+2}$ and the hydrogen peroxide applied in the E2 stage was 0.6%. The pH of the treatment stage was 3.0, the temperature was 82° C., and the retention time was approximately 80 minutes. The pulp was washed and then treated in a D2 stage with 0.2% $ClO_2$ at 92° C. for approximately 150 minutes. The 0.5% Capillary CED viscosity of the fully bleached pulp was 5.5 mPa·s (DPw 914) and the ISO brightness was 88.2.

Example 16

The pulp produced in Example 15 was made into a pulp board on a Fourdrinier type pulp dryer with an airborne Flakt™ dryer section. Samples of a standard pulp and the pulp of the present invention (ULDP) were collected and analyzed for chemical composition and fiber properties. The results are shown in Table 15.

TABLE 15

| Property | | Standard | ULDP |
|---|---|---|---|
| R10 | % | 86.8 | 82.4 |
| S10 | % | 13.2 | 17.6 |
| R18 | % | 87.0 | 85.4 |
| S18 | % | 13.0 | 14.6 |
| ΔR | | 0.2 | 3.0 |

TABLE 15-continued

| Property | | Standard | ULDP |
|---|---|---|---|
| Carboxyl | meq/100 g | 3.13 | 3.70 |
| Aldehydes | meq/100 g | 0.97 | 2.15 |
| Copper No. | | 0.51 | 1.3 |
| Calculated Carbonyl | mmole/100 g | 0.73 | 2.05 |
| 0.5% Capillary CED Viscosity | mPa · s | 15.0 | 6.5 |
| Intrinsic Viscosity | dl/g | 7.14 | 4.33 |
| Calculated DP | $DP_w$ | 2036 | 1084 |
| Glucan | % | 83.0 | 84.6 |
| Xylan | % | 9.0 | 9.4 |
| Galactan | % | 0.2 | 0.2 |
| Mannan | % | 5.9 | 5.3 |
| Arabinan | % | 0.4 | 0.3 |
| Calculated Cellulose | % | 81.0 | 82.8 |
| Calculated Hemicellulose | % | 17.5 | 17.0 |
| Lwl Fiber Length | mm | 2.55 | 2.53 |
| Lww Fiber Length | mm | 3.29 | 3.34 |
| Coarseness | mg/m | 0.218 | 0.234 |
| Wet Zero Span Tensile | km | 9.38 | 6.83 |
| Freeness (CSF) | mls | 738 | 737 |
| Iron | ppm | 1.6 | 4.4 |
| Brightness | % ISO | 89.6 | 88.2 |

The treated pulp (ULDP) had a higher alkali solubility in 10% and 18% NaOH and a higher aldehyde and total carbonyl content. The ULDP was significantly lower in DP as measured by 0.5% Capillary CED viscosity and lower wet zero span breaking length. The brightness was still an acceptable value of 88.2. The treatment preserved the fiber length and freeness and there were no operational issues forming and drying the board.

Example 17

The E2 (EP) stage of a OD(E0)D(EP)D sequence was altered to produce a low degree of polymerization pulp in a similar manner as Example 13. In this case the $FeSO_4.7H_2O$ was added at 25 ppm as $Fe^{+2}$ and the hydrogen peroxide applied in the E2 stage was 0.2%. The pH of the treatment stage was 3.0, the temperature was 82° C. and the retention time was approximately 80 minutes. The pulp was washed then treated in a D2 stage with 0.2% $ClO_2$ at 92° C. for approximately 150 minutes. The 0.5% Capillary CED viscosity of the fully bleached pulp was 8.9 mPa·s (DPw 1423) and the ISO brightness was 89.

Example 18

The pulp produced in Example 15 was made into a pulp board on a Fourdrinier type pulp dryer with an airborne Flakt™ dryer section. Samples of a standard pulp and the low degree of polymerization pulp of the present invention (LDP) were collected and analyzed for chemical composition and fiber properties. The results are shown in Table 16.

TABLE 16

| Property | | Standard | LDP |
|---|---|---|---|
| R10 | % | 86.8 | 85.2 |
| S10 | % | 13.2 | 14.8 |
| R18 | % | 87.0 | 87.2 |
| S18 | % | 13.0 | 12.8 |
| ΔR | | 0.2 | 2.0 |
| Carboxyl | meq/100 g | 3.13 | 3.53 |
| Aldehydes | meq/100 g | 0.97 | 1.24 |
| Copper No. | | 0.51 | 1.2 |
| Calculated Carbonyl | mmole/100 g | 0.73 | 1.88 |
| 0.5% Capillary CED | mPa · s | 15.0 | 8.9 |

TABLE 16-continued

| Property | | Standard | LDP |
|---|---|---|---|
| Viscosity | | | |
| Intrinsic Viscosity | dl/g | 7.14 | 5.44 |
| Calculated DP | $DP_w$ | 2036 | 1423 |
| Glucan | % | 83.0 | 85.9 |
| Xylan | % | 9.0 | 8.8 |
| Galactan | % | 0.2 | 0.2 |
| Mannan | % | 5.9 | 5.4 |
| Arabinan | % | 0.4 | 0.3 |
| Calculated Cellulose | % | 81.0 | 84.1 |
| Calculated Hemicelllulose | % | 17.5 | 16.5 |
| Lwl Fiber Length | mm | 2.55 | 2.57 |
| Lww Fiber Length | mm | 3.29 | 3.34 |
| Coarseness | mg/m | 0.218 | 0.222 |
| Iron | ppm | 1.6 | 5.5 |
| Brightness | % ISO | 89.6 | 89.0 |

The treated pulp (LDP) had a higher alkali solubility in 10% and 18% NaOH and a higher aldehyde and total carbonyl content. The LDP was lower in DP as measured by 0.5% Capillary CED viscosity. There was a minimal loss in brightness. The treatment preserved the fiber length and there were no operational issues forming and drying the board.

Example 19

The pulp boards described in Example 14 were fiberized and airformed into 4"×7" pads using a Kamas Laboratory Hammermill (Kamas Industries, Sweden). The airformed pads were then compressed at various gauge pressures using a laboratory press. After pressing, the pad caliper was measured using an Emveco microgage caliper gage model 200-A with a foot pressure of 0.089 psi. Pad density was calculated from the pad weight and caliper. The results are depicted in Table 17.

TABLE 17

| | Gauge Pressure | | | | | | | | |
|---|---|---|---|---|---|---|---|---|---|
| | 5 psi | | | 10 psi | | | 20 psi | | |
| | Caliper mm | Pad Wt g | Density g/cc | Caliper mm | Pad Wt g | Density g/cc | Caliper mm | Pad Wt g | Density g/cc |
| Standard Kraft Southern Pine Fiber | 2.62 | 5.14 | 0.108 | 2.29 | 5.27 | 0.127 | 1.49 | 5.29 | 0.196 |
| | 2.81 | 5.14 | 0.101 | 2.26 | 5.19 | 0.127 | 1.42 | 5.23 | 0.203 |
| Modified Kraft Southern Pine Fiber | 2.51 | 5.16 | 0.114 | 2.13 | 5.33 | 0.138 | 1.23 | 5.39 | 0.242 |
| | 2.56 | 5.26 | 0.114 | 1.93 | 5.37 | 0.154 | 1.32 | 5.26 | 0.220 |
| Percent Increase in Density | | | 8.43 | | | 14.94 | | | 15.67 |

The data in Table 17 show that the modified fibers produced within the scope of this disclosure were more compressible, resulting in thinner and higher density structures more suitable for today's disposable absorbent product designs.

Without being bound by theory, it is believed that the oxidation of the cellulose disrupts the crystalline structure of the polymer, rendering it less stiff and more conformable. The fibers composed of the modified cellulose structure then become more compressible, allowing for the production of higher density absorbent structures.

Example 20

A Southern pine pulp was collected from the D1 stage of a OD(EO)D(EP)D sequence. The starting 0.5% Capillary CED viscosity was 14.9 mPa·s (DPw 2028). Either 1.0% or 2% hydrogen peroxide was added with 100 or 200 ppm of $Fe^{+2}$ respectively. Other treatment conditions were 10% consistency, 80° C., and 1 hour retention time. These fluff pulps were then slurried with deionized water, wetlaid on a screen to form a fiber mat, dewatered via roller press, and dried at 250° F. The dry sheets were defibrated and airformed into 4"×7" airlaid pads weighing 8.5 grams (air dried) using a Kamas Laboratory Hammermill (Kamas Industries, Sweden). A single, complete coverage sheet of nonwoven coverstock was applied to one face of each pad and the samples were densified using a Carver hydraulic platen press applying a load of 145 psig.

These pads were placed in individual 1.6 L airtight plastic containers having a removable lid fitted with a check valve and sampling port of ¼" ID Tygon® tubing. Before securing the lid of the container, an insult of 60 grams deionized water and 0.12 gram 50% $NH_4OH$ at room temperature was poured into a centered 1" ID vertical tube on a delivery device capable of applying a 0.1 psi load across the entirety of the sample. Upon full absorption of the insult, the delivery device was removed from the sample, the lid, with sealed sampling port, was fitted to the container, and a countdown timer started. At the conclusion of 45 minutes, a headspace sample was taken from the sampling port with an ammonia-selective short-term gas detection tube and ACCURO® bellows pump, both available from Draeger Safety Inc., Pittsburgh, Pa. The data in Table 18 show that the modified fibers produced within the scope of this disclosure were able to reduce the amount of ammonia gas in the headspace, resulting in a structure that provides suppression of a volatile malodorous compound often cited as unpleasant in wetted incontinence products.

TABLE 18

| Insult-60 g $H_2O$/ 0.12 g 50% $NH_4OH$ | 0.5% CED Viscosity (mPa · s) | Aldehyde Content meq/100 g | Air Laid Pad Weight (g) | Ammonia (ppm) @ 45 mins |
|---|---|---|---|---|
| Standard Kraft Southern Pine Fiber | 14.9 | 0.23 | 9.16 | 210 |
| Modified Kraft Southern Pine Fiber-1.0% $H_2O_2$/100 ppm Fe | 4.7 | 3.26 | 9.11 | 133 |
| Modified Kraft Southern Pine Fiber-2.0% $H_2O_2$/200 ppm Fe | 3.8 | 4.32 | 9.23 | 107 |

Example 21

The E2 stage of a OD(EO)D(EP)D sequence of a commercial kraft pulping facility was altered to produce the low degree of polymerization pulp in a similar manner as Example 14. In this example, the $FeSO_4.7H_2O$ was added at 100 ppm as $Fe^{+2}$ and the hydrogen peroxide applied in the E2 stage was 1.4%. The pulp properties are shown in Table 19.

TABLE 19

| Property | | ULDP |
|---|---|---|
| R10 | % | 72.5 |
| S10 | % | 27.5 |
| R18 | % | 78.7 |
| S18 | % | 21.3 |
| ΔR | | 6.2 |
| Carboxyl | meq/100 g | 3.94 |
| Aldehydes | meq/100 g | 4.21 |
| Copper No. | | 4.25 |
| Calculated Carbonyl | mmole/100 g | 6.97 |
| 0.5% Capillary CED Viscosity | mPa · s | 3.50 |
| Intrinsic Viscosity | dl/g | 2.49 |
| Calculated DP | $DP_w$ | 485 |
| Lwl Fiber Length | mm | 2.31 |
| Coarseness | mg/m | 0.19 |
| Brightness | % ISO | 88.5 |

The modified chemical cellulose produced was made into a pulp board on a Fourdrinier type pulp dryer with an airborne Flakt™ dryer section. Samples of this product and control kraft pulp board were defibrated using the Kamas laboratory hammermill. Optical analysis of fiber properties were performed on both pre and post Kamas mill samples via HiRes Fiber Quality Analyzer available from Optest Equipment, Inc., Hawkesbury, ON, Canada, according to the manufacturer's protocols. The results are depicted in the table below.

TABLE 20

| Property | Control | ULDP | Control post-hammermill | ULDP post-hammermill |
|---|---|---|---|---|
| Kink index | 1.79 | 2.29 | 1.51 | 2.32 |
| Kink angle | 59.15 | 79.56 | 48.52 | 80.26 |
| Kinks per mm | 0.81 | 1.07 | 0.68 | 1.06 |
| Curl Index (length weighted) | 0.171 | 0.211 | 0.149 | 0.225 |

As can be seen in Table 20, the ULDP fibers prepared in accordance with the disclosure have higher kink and curl than control fibers not treated with iron and peroxide.

The defibrated fibers above were airformed into 4"×7" pads weighing 4.25 grams (air-dried). Sodium polyacrylate superabsorbent (SAP) granules sourced from BASF were applied evenly between two 4.25 gram pads. A full coverage nonwoven coverstock was applied to the top face of the fiber/SAP matrix and the pad was densified by a load of 145 psig applied via Carver platen press.

Synthetic urine was prepared by dissolving 2% Urea, 0.9% Sodium Chloride, and 0.24% nutrient broth (Criterion™ brand available through Hardy Diagnostics, Santa Maria, Calif.) in deionized water, and adding an aliquot of Proteus Vulgaris resulting in a starting bacterial concentration of $1.4 \times 10^7$ CFU/ml. The pad described above was then placed in a headspace chamber as described in Example 20 and insulted with 80 ml of the synthetic urine solution. Immediately after insult, the chamber was sealed and placed in an environment with a temperature of 30° C. Dräger sampling was performed in series at time intervals of four hours and seven hours. The experiment was repeated three times, and the average results are reported in Table 21.

TABLE 21

| | % SAP add on | Ammonia (ppm) @ 4 hrs | % reduction over control | Ammonia (ppm) @ 7 hrs | % reduction over control |
|---|---|---|---|---|---|
| Modified Kraft Southern Pine Fiber | 23 | 2.5 | | 29 | |
| Control Kraft Southern Pine Fiber | 23 | 21.5 | 88 | 175 | 83 |
| Modified Kraft Southern Pine Fiber | 16.5 | 6.5 | | 123 | |
| Control Kraft Southern Pine Fiber | 16.5 | 36.5 | 82 | 550 | 78 |
| Modified Kraft Southern Pine Fiber | 0 | 70 | | 317 | |
| Control Kraft Southern Pine Fiber | 0 | 197.5 | 65 | 575 | 45 |

As can be seen from the data, atmospheric ammonia resulting from bacterial hydrolysis of urea is lower in composite structures (similar in construction to retail urinary incontinence products) incorporating modified cellulose fibers produced within the scope of this disclosure versus composite structures produced with standard kraft southern pine fibers. Thus, structures comprising modified cellulose fibers according to the disclosure had better odor control properties than standard kraft southern pine fibers.

Example 22

Comparison of 4Th Stage to Post-Bleach Treatment

A Southern pine pulp was collected from the D1 stage of a OD(E0)D1(EP)D2 sequence. The starting 0.5% Capillary CED viscosity was 14.1 mPa·s. Hydrogen peroxide was added as 1.5% based on the dry weight of the pulp with 150 ppm of $Fe^{+2}$. As used herein, "P*" is used to indicate an iron and hydrogen peroxide treatment stage The treatment was conducted at 10% consistency at a temperature of 78° C. for 1 hour in the fourth stage of the sequence. This treated pulp was then washed and bleached in D2 stage with 0.25% $ClO_2$ for 2 hours at 78° C. The results are shown in Table 22.

TABLE 22

| Stage | Chemical added % on pulp | | pH final | 0.5% Capillary CED Viscosity mPa·s | ΔViscosity | DPw | Brightness % ISO | Length weighted Fiber Length mm |
|---|---|---|---|---|---|---|---|---|
| D1 | | | | 14.1 | | 1960 | 83.5 | |
| P* | 1.5% $H_2O_2$ | 150 ppm $Fe^{+2}$ | 3.1 | | | | 82.0 | |
| D2 | 0.25% $ClO_2$ | | 2.7 | 3.7 | 10.4 | 540 | 89.5 | 2.20 |

The D2 sample above was also tested for brightness reversion by placing it in an oven at 105° C. for 1 hour. The brightness as well as L* (whiteness), a* (red to green), and b* (blue to yellow) values were measured by a Hunterlab MiniScan, according to the manufacturer's protocols, before and after the reversion treatment. The results are shown in Table 23 below. More positive b values indicate a more yellow color. Thus, higher b values are undesirable in most paper and pulp applications. Post color number, reported below, represents the difference in the ratio k/s before and after aging, where k=absorption coefficient and s=scattering coefficient. i.e., post color no.=$100\{(k/s)_{after\ aging}-(k/S)_{before\ aging}\}$. See, e.g., H. W. Giertz, *Svensk Papperstid.*, 48(13), 317 (1945).

TABLE 23

| | Brightness Reversion | | | | | |
|---|---|---|---|---|---|---|
| Stage | L* | a* | b* | Brightness | ΔBrightness | Post Color No. |
| D1 | 96.89 | −0.28 | 5.13 | 85.8 | | |
| DP*D initial | 97.89 | −0.47 | 2.96 | 90.8 | | |
| DP*D reverted | 96.08 | −0.55 | 8.01 | 80.4 | 10.4 | 1.92 |

A Southern pine pulp was collected from the D2 stage of the same bleach plant as above with the same starting Capillary CED viscosity and was treated with hydrogen peroxide and $Fe^{+2}$ as described above. Hydrogen peroxide was added as 1.5% based on the dry weight of the pulp with 150 ppm of Fe+$^2$. The properties of this treated pulp are depicted in Table 24.

TABLE 24

| Stage | Chemical added % on pulp | | pH final | 0.5% Capillary CED Viscosity mPa·s | ΔViscosity | DPw | Brightness % ISO | Length weighted Fiber Length mm |
|---|---|---|---|---|---|---|---|---|
| D2 | | | | 14.1 | | 1960 | 90.2 | |
| P* | 1.5% $H_2O_2$ | 150 ppm $Fe^{+2}$ | 2.8 | 3.5 | 10.6 | 485 | 86.8 | 2.17 |

The P* pulp was tested for brightness reversion as described above. The results are depicted in Table 25 below.

TABLE 25

| | Brightness Reversion | | | | | |
|---|---|---|---|---|---|---|
| Stage | L* | a* | b* | Brightness | ΔBrightness | Post Color No. |
| D2 Initial | 98.34 | −0.61 | 2.54 | 92.54 | | |
| D2 Reverted | 97.87 | −0.57 | 3.67 | 89.92 | 2.62 | 0.26 |

TABLE 25-continued

| | Brightness Reversion | | | | | |
|---|---|---|---|---|---|---|
| Stage | L* | a* | b* | Brightness | ΔBrightness | Post Color No. |
| D(EP)DP* initial | 97.39 | −0.47 | 4.49 | 87.68 | | |
| D(EP)DP* reverted | 95.25 | −0.34 | 9.78 | 76.45 | 11.2 | 2.76 |

As can be seen from the above data, acidic catalyzed peroxide treatment in the fourth stage of a five-stage bleach plant compared to treatment following the final stage of a five-stage bleach plant results in beneficial brightness properties. In the fourth stage treatment, any brightness loss from the treatment stage can be compensated for with the final D2 bleaching stage so that a high brightness pulp is still obtained. In the case of post-bleach treatment, there is a significant brightness loss of 3.4 points that cannot be compensated for. After an accelerated brightness reversion treatment, the latter case still has a significantly lower brightness.

Example 23

Strength Data

The strength of fluff pulp produced from modified cellulose with a viscosity of 5.1 mPa·s according to the disclosure was compared with conventional fluff pulp having a viscosity of 15.4 mPa·s. The results are depicted in Table 26 below.

TABLE 26

|  | Control Fluff | Modified Cellulose |
|---|---|---|
| Basis Wt., gm/m² AD | 65.12 | 68.15 |
| Basis Wt., gm/m² OD | 60.56 | 63.38 |
| Freeness CSF, mls | 732 | 717 |
| Caliper, in/1000 | 4.88 | 5.09 |
| Bulk, cm³/gm | 1.90 | 1.90 |
| Apparent Density, gm/cm³ | 0.53 | 0.53 |
| Porosity, sec/100 mls air | 0.59 | 0.67 |
| Burst Factor, (gm/cm²)/(gm/m²) | 16.6 | 14.0 |
| Tear Factor, gf*m²/gm | 242 | 198 |
| Breaking Length, km | 2.52 | 2.49 |
| Stretch, % | 2.76 | 2.48 |
| Opacity, % | 72.1 | 73.5 |
| Dirt and Shives, mm²/m² | 0.3 | 1.5 |
| Viscosity, cP | 15.4 | 5.1 |
| ISO Brightness | 88.9 | 88.9 |
| Frazier Porosity, cfm | 45.4 | 55.1 |
| Fiber Length, mm | 2.636 | 2.661 |
| Shape Factor, % | 85.8 | 85.8 |

Example 24

Derivatization of Modified Cellulose

A sample of ULDP from Example 21 was acid hydrolyzed with 0.05 M HCl at 5% consistency for 3 hours at 122° C. The initial pulp from the D1 stage, the ULDP, and the acid hydrolyzed ULDP were tested for average molecular weight or degree of polymerization by the method below.

Three pulp samples were grounded to pass a 20 mesh screen. Cellulose samples (15 mg) were placed in separate test tubes equipped with micro stir bars and dried overnight under vacuum at 40° C. The test tubes were then capped with rubber septa. Anhydrous pyridine (4.00 mL) and phenyl isocyanate (0.50 mL) were added sequentially via syringe. The test tubes were placed in an oil bath at 70° C. and allowed to stir for 48 h. Methanol (1.00 mL) was added to quench any remaining phenyl isocyanate. The contents of each test tube were then added dropwise to a 7:3 methanol/water mixture (100 mL) to promote precipitation of the derivatized cellulose. The solids were collected by filtration and then washed with methanol/water (1×50 mL) followed by water (2×50 mL). The derivatized cellulose was then dried overnight under vacuum at 40° C. Prior to GPC analysis the derivatized cellulose was dissolved in THF (1 mg/mL), filtered through a 0.45 μm filter, and placed in a 2 mL auto-sampler vial. The resulting DPw and DPn (number average degree of polymerization) are reported in Table 27 below.

TABLE 27

DPn and DPw test results

| Sample | Mn (g/mol) | Mw (g/mol) | DPn | DPw |
|---|---|---|---|---|
| D1 | 1.4601e5 | 2.2702e6 | 281 | 4374 |
| ULDP | 4.0775e4 | 7.4566e5 | 78 | 1436 |
| Acid Hydrolyzed ULDP | 2.52.5e4 | 1.8966e5 | 48 | 365 |

As can be seen in the above table, modified cellulose after acid hydrolysis according to the disclosure can have a DPn of 48.

Example 25

Leaf River ULDP fibers and standard softwood fibers were made into handsheets by slurrying the fiber, adjusting the pH to about 5.5, and then adding, as a temporary wet strength agent, a glyoxylated polyacrylamide from Kemira Chemicals. The fibers were then formed, pressed into sheets and dried. The characteristics of the sheets were measured by known methods. The results are reported in Table 28 below.

TABLE 28

Handsheet properties

|  |  | LR SW (Control) | | | | ULDP | | | |
|---|---|---|---|---|---|---|---|---|---|
| TWS | #T | 0 | 10 | 20 | 40 | 0 | 10 | 20 | 40 |
| Titratable Charge | mL/10 mL 10-3N | −0.166 | +0.204 | +0.389 | +2.899 | −0.143 | −0.134 | +0.474 | +1.919 |
| Basis Weight | #R | 15.11 | 16.19 | 15.59 | 14.64 | 15.75 | 14.83 | 13.08 | 15.3 |
|  | g/m2 | 24.59 | 26.35 | 25.37 | 23.83 | 25.63 | 24.14 | 21.29 | 24.9 |
| Bulk | 1-ply Caliper, mils | 3.68 | 3.78 | 3.80 | 4.04 | 3.80 | 3.72 | 4.12 | 4.08 |
|  | Bulk, cm3/g | 3.80 | 3.64 | 3.80 | 4.31 | 3.77 | 3.91 | 4.92 | 4.16 |
| Dry Tensile | Tensile, g/1" | 747 | 1335 | 1187 | 1118 | 716 | 825 | 866 | 864 |
|  | Breaking Length, km | 1.196 | 1.995 | 1.842 | 1.847 | 1.100 | 1.346 | 1.602 | 1.366 |
|  | Stretch, % | 2.6 | 3.2 | 2.9 | 3.0 | 2.2 | 2.7 | 3.3 | 2.9 |
|  | T.E.A., mm-gm/mm² | 0.10 | 0.28 | 0.21 | 0.21 | 0.06 | 0.11 | 0.17 | 0.12 |
| Wet Tensile | Tensile, g/1" | 4 | 209 | 218 | 256 | 23 | 148 | 200 | 168 |
|  | Breaking Length, km | 0.0064 | 0.3123 | 0.3383 | 0.423 | 0.0353 | 0.2414 | 0.3699 | 0.2656 |
| SAT | Capacity, g/m² | 205.9 | 194.7 | 187.0 | 190.9 | 185.0 | 173.0 | 182.0 | 202.0 |
|  | Rate, g/s$^{0.5}$ | 0.06 | 0.08 | 0.07 | 0.05 | 0.08 | 0.07 | 0.07 | 0.10 |
|  | Time, s | 89.6 | 59.1 | 59.2 | 83.8 | 55.5 | 50.0 | 57.7 | 49.9 |
| Wet/Dry ratio |  | 1% | 16% | 18% | 23% | 3% | 18% | 23% | 19% |

As can be seen in the above Table 28, ULDP according to the disclosure may be used in production of wet pressed paper. As is shown in FIG. 2, the wet/dry ratio of the handsheets formed from ULDP is higher than the wet/dry ratio of comparative sheets made from only standard southern softwood.

Example 26

Wicking, Rewet, and Strength Data

The synthetic urine wicking capability of sheets of various densities (0.15, 0.25, and 0.35 g/cm³) and basis weights (60, 150, 300 gsm) made from pulp produced from modified cellulose according to the disclosure and 10% bicomponent fiber was compared with sheets made from conventional kraft pulp. Tests were conducted by Materials Testing Service of Kalamazoo, Mich., using their own test equipment and procedures. The synthetic urine wicking capability of the products was tested using 6.0 cm×16.0 cm samples and a 600 second pin read time. The results are depicted in Table 29 below.

TABLE 29

Synthetic Urine 45° Wicking Data

| Basis Wt. | Bottom Pin Wicking Time (sec) | | Top Pin Wicking Time (sec) | | Total Wicking Time (sec) | |
| --- | --- | --- | --- | --- | --- | --- |
| | Conventional | Modified | Conventional | Modified | Conventional | Modified |
| Density 0.15 g/cm³ | | | | | | |
| 60 gsm | 36.86 | 31.24 | 365.4 | 306.63 | 394.71 | 337.87 |
| 150 gsm | 30.13 | 30.80 | 270.43 | 292.56 | 296.53 | 319.57 |
| 300 gsm | 25.98 | 25.05 | 105.86 | 88.03 | 131.84 | 113.08 |
| Density 0.25 g/cm³ | | | | | | |
| 60 gsm | 40.25 | 45.65 | 220.7 | 226.59 | 260.95 | 272.24 |
| 150 gsm | 31.13 | 27.14 | 119.70 | 156.15 | 150.83 | 183.29 |
| 300 gsm | 39.18 | 37.58 | 118.44 | 123.11 | 157.62 | 160.68 |
| Density 0.35 g/cm³ | | | | | | |
| 60 gsm | 42.24 | 40.44 | 206.08 | 186.27 | 248.32 | 226.71 |
| 150 gsm | 43.32 | 35.55 | 148.91 | 127.45 | 192.23 | 163.00 |
| 300 gsm | 50.84 | 55.65 | 176.74 | 183.59 | 227.57 | 239.24 |

The amount retained, change in thickness, and wicking height were also determined. The results are depicted in Table 30 below:

TABLE 30

| | Wet Wt. (g) | Dry Wt. (g) | Amount Retained (g) | Beginning Thickness (mm) | End Thickness (mm) | % Change | Wicking Height (g) |
| --- | --- | --- | --- | --- | --- | --- | --- |
| Conventional | | | | | | | |
| 60 GSM-0.15 DENSITY | 5.26 | 0.62 | 4.63 | 0.40 | 0.66 | 66.0 | 15.2 |
| 60 GSM-0.25 DENSITY | 4.62 | 0.61 | 4.01 | 0.24 | 0.54 | 122.9 | 15.7 |
| 60 GSM-0.35 DENSITY | 4.32 | 0.62 | 3.70 | 0.17 | 0.53 | 213.5 | 16.0 |
| 150 GSM-0.15 DENSITY | 15.63 | 1.73 | 13.91 | 1.00 | 1.67 | 67.2 | 16.0 |
| 150 GSM-0.25 DENSITY | 12.07 | 1.72 | 10.35 | 0.60 | 1.30 | 116.0 | 16.0 |
| 150 GSM-0.35 DENSITY | 9.42 | 1.78 | 7.64 | 0.43 | 0.92 | 114.9 | 16.0 |
| 300 GSM-0.15 DENSITY | 29.64 | 3.51 | 26.14 | 1.95 | 3.12 | 59.8 | 16.0 |
| 300 GSM-0.25 DENSITY | 21.36 | 3.51 | 17.85 | 1.20 | 2.09 | 74.2 | 16.0 |
| 300 GSM-0.35 DENSITY | 13.70 | 3.49 | 10.22 | 0.87 | 1.73 | 99.3 | 16.0 |
| Modified | | | | | | | |
| 60 GSM-0.15 DENSITY | 5.17 | 0.60 | 4.57 | 0.40 | 0.79 | 98.3 | 15.5 |
| 60 GSM-0.25 DENSITY | 4.07 | 0.61 | 3.46 | 0.24 | 0.54 | 125.4 | 15.9 |
| 60 GSM-0.35 DENSITY | 3.96 | 0.60 | 3.36 | 0.17 | 0.48 | 180.6 | 16.0 |

TABLE 30-continued

| | Wet Wt. (g) | Dry Wt. (g) | Amount Retained (g) | Beginning Thickness (mm) | End Thickness (mm) | % Change | Wicking Height (g) |
|---|---|---|---|---|---|---|---|
| 150 GSM-0.15 DENSITY | 15.08 | 1.77 | 13.31 | 1.00 | 1.76 | 75.5 | 16.0 |
| 150 GSM-0.25 DENSITY | 13.02 | 1.72 | 11.29 | 0.60 | 1.47 | 145.3 | 16.0 |
| 150 GSM-0.35 DENSITY | 10.53 | 1.76 | 8.77 | 0.43 | 1.21 | 180.7 | 16.0 |
| 300 GSM-0.15 DENSITY | 32.73 | 3.59 | 29.14 | 1.95 | 2.58 | 32.2 | 16.0 |
| 300 GSM-0.25 DENSITY | 22.98 | 3.55 | 19.43 | 1.20 | 2.14 | 78.0 | 16.0 |
| 300 GSM-0.35 DENSITY | 12.41 | 3.50 | 8.91 | 0.87 | 1.73 | 98.4 | 16.0 |

The same sheets were also subjected to rewet testing. The rewet of the products was tested with 9.0 cm×20.3 cm sample cutouts using the dosing tube method and one dose of 10 ml of 0.9% saline solution. 120 seconds after the dose the dosing tube was removed and a recorded preweighed 6"×6" sheet of Verigood blotter paper was placed on top and a 3 kpa load was applied for 60 seconds. The results are depicted in Table 31 below.

TABLE 31

| | Rewet Data | |
|---|---|---|
| | Rewet (GMS) | |
| Basis Wt. | Conventional | Modified |
| Density 0.15 g/cm³ | | |
| 60 gsm | 5.89 | 6.13 |
| 150 gsm | 5.19 | 5.52 |
| 300 gsm | 3.98 | 3.49 |
| Density 0.25 g/cm³ | | |
| 60 gsm | 6.01 | 6.20 |
| 150 gsm | 4.46 | 5.00 |
| 300 gsm | 3.59 | 4.14 |
| Density 0.35 g/cm³ | | |
| 60 gsm | 6.06 | 6.50 |
| 150 gsm | 3.66 | 4.11 |
| 300 gsm | 2.64 | 2.59 |

The same sheets were also subjected to dry and wet tensile strength and percent elongation testing. Tensile strength and percent elongation were determined for each product in the machine direction using a gauge length of 5.00 cms, a sample width of 1.3 cms., a crosshead speed of 2.5 cm/min and a load cell of 30 kg. The results are depicted in Tables 32 and 33 below.

TABLE 32

| | Dry Tensile Strength and Percent Elongation Summary | | | | | |
|---|---|---|---|---|---|---|
| | Peak (KGS) | | Elongation (%) | | TEA (JLS/M2) | |
| Basis Wt. | Conventional | Modified | Conventional | Modified | Conventional | Modified |
| Density 0.15 g/cm³ | | | | | | |
| 60 gsm | 0.21 | 0.24 | 30.11 | 24.66 | 23.73 | 29.80 |
| 150 gsm | 0.54 | 0.45 | 34.78 | 30.62 | 71.23 | 57.85 |
| 300 gsm | 1.03 | 1.46 | 31.35 | 21.70 | 132.12 | 157.90 |
| Density 0.25 g/cm³ | | | | | | |
| 60 gsm | 0.23 | 0.24 | 30.59 | 22.90 | 27.02 | 29.13 |
| 150 gsm | 1.04 | 0.52 | 27.66 | 37.13 | 135.89 | 74.44 |
| 300 gsm | 1.61 | 1.38 | 23.81 | 22.63 | 177.01 | 161.93 |
| Density 0.35 g/cm³ | | | | | | |
| 60 gsm | 0.18 | 0.16 | 30.25 | 20.75 | 20.50 | 17.78 |
| 150 gsm | 0.78 | 0.88 | 26.44 | 27.60 | 101.51 | 111.05 |
| 300 gsm | 4.36 | 3.82 | 11.22 | 8.25 | 201.33 | 182.50 |

TABLE 33

Wet Tensile Strength and Percent Elongation Summary

| Basis Wt. | Peak (KGS) Conventional | Peak (KGS) Modified | Elongation (%) Conventional | Elongation (%) Modified | TEA (JLS/M2) Conventional | TEA (JLS/M2) Modified |
|---|---|---|---|---|---|---|
| Density 0.15 g/cm³ | | | | | | |
| 60 gsm | 0.07 | 0.09 | 20.91 | 23.13 | 6.75 | 10.28 |
| 150 gsm | 0.21 | 0.16 | 46.85 | 25.12 | 25.89 | 20.70 |
| 300 gsm | 0.40 | 0.60 | 45.23 | 20.20 | 48.94 | 66.69 |
| Density 0.25 g/cm³ | | | | | | |
| 60 gsm | 0.08 | 0.09 | 22.57 | 21.10 | 8.19 | 9.18 |
| 150 gsm | 0.36 | 0.21 | 39.03 | 24.96 | 48.09 | 27.25 |
| 300 gsm | 0.73 | 0.60 | 26.82 | 19.44 | 83.21 | 68.20 |
| Density 0.35 g/cm³ | | | | | | |
| 60 gsm | 0.07 | 0.06 | 21.67 | 22.55 | 7.56 | 7.11 |
| 150 gsm | 0.33 | 0.31 | 20.88 | 22.69 | 39.20 | 39.11 |
| 300 gsm | 1.85 | 1.97 | 22.58 | 15.84 | 206.55 | 186.85 |

Example 27

Wettability, Vertical Wicking and Horizontal Wicking Data

The wettability, vertical wicking, and horizontal wicking of sheets of various densities (0.15, 0.30, and 0.45 g/cm³) made from pulp produced from modified cellulose according to the disclosure was compared with sheets made from conventional pulp. Tests were conducted by Materials Testing Service of Kalamazoo, Mich., using their own test equipment and procedures.

The demand wettability characteristics were determined using 10 50 cm² samples. The results are depicted in Tables 34-36 below.

TABLE 34

Demand Wettability Test Final Absorption Rate

| Density g/cm³ | Absorption Rate (ML/G*sec^.5) Conventional | Absorption Rate (ML/G*sec^.5) Modified |
|---|---|---|
| 0.15 | 0.80 | 0.92 |
| 0.30 | 0.55 | 0.62 |
| 0.45 | 0.42 | 0.46 |

TABLE 35

Demand Wettability Test Total Absorption Amount

| Density g/cm³ | Absorption (MLS) Conventional | Absorption (MLS) Modified |
|---|---|---|
| 0.15 | 18.99 | 21.53 |
| 0.30 | 14.33 | 15.11 |
| 0.45 | 11.91 | 12.04 |

TABLE 36

Demand Wettability Test Absorption Capacity Index

| Density g/cm³ | Absorption Capacity (ML/G) Conventional | Absorption Capacity (ML/G) Modified |
|---|---|---|
| 0.15 | 6.33 | 7.18 |
| 0.30 | 4.78 | 5.04 |
| 0.45 | 3.97 | 4.01 |

The vertical wicking characteristics were determined using 10 samples and a 600 second probe read time. The results are depicted in Tables 37-38 below.

TABLE 37

Vertical Wicking Test Total Wicking Time

| Density g/cm³ | Average Total Wicking Time (seconds) Conventional | Average Total Wicking Time (seconds) Modified |
|---|---|---|
| 0.15 | 29.68 | 29.14 |
| 0.30 | 29.36 | 24.34 |
| 0.45 | 51.40 | 39.72 |

TABLE 38

Vertical Wicking Test Total Amount Retained

| Density g/cm³ | Amount Retained (ML) Conventional | Amount Retained (ML) Modified |
|---|---|---|
| 0.15 | 13.49 | 13.43 |
| 0.30 | 11.36 | 11.48 |
| 0.45 | 7.79 | 8.70 |

The horizontal wicking characteristics were determined using 10 samples, a 600 second probe read time, and one 30 ml dose at 7 ml/sec. The results are depicted in Table 39 below.

TABLE 39

Horizontal Wicking Time

| Level | Average Wicking Time (seconds) Conventional | Modified |
|---|---|---|
| \multicolumn{3}{l}{Density 0.15 g/cm³} | | |
| 1 | 1.07 | 0.97 |
| 2 | 2.47 | 2.30 |
| 3 | 4.80 | 4.47 |
| 4 | 23.80 | 15.46 |
| 5 | 131.70 | 154.96 |
| \multicolumn{3}{l}{Density 0.30 g/cm³} | | |
| 1 | 1.02 | 1.14 |
| 2 | 2.44 | 2.48 |
| 3 | 4.77 | 4.57 |
| 4 | 25.18 | 18.21 |
| 5 | 163.45 | 81.93 |
| \multicolumn{3}{l}{Density 0.45 g/cm³} | | |
| 1 | 1.05 | 0.99 |
| 2 | 2.61 | 2.33 |
| 3 | 5.08 | 4.36 |
| 4 | 31.08 | 9.75 |
| 5 | 165.95 | 75.90 |

Example 28

Multilayer Absorbent Sheets

Five different airlaid multilayer sheets were prepared and cut into 200 4×8 inch rectangles. The differing sets were labeled as shown in Table 40. Where noted, conventional sheets were treated with TQ-2021 and modified sheets were treated with TQ-2028, both surface active agents supplied by Ashland, Inc.

TABLE 40

| Sheet | Top Layer | Middle Layer | Bottom Layer |
|---|---|---|---|
| Standard MR4 | Conventional with TQ-2021 | Non GP untreated | Conventional with TQ-2021 |
| Trial MR5 | Conventional with TQ-2021 | Non GP untreated | Modified with TQ-2028* |
| Trial MR6 | Conventional with TQ-2021 | Modified | Modified with TQ-2028* |
| Trial MR7 | Modified with TQ-2028* | Modified | Conventional with TQ-2021 |
| Trial MR8 | Modified with TQ-2028* | Non GP untreated | Conventional with TQ-2021 |

The products were tested for fluid acquisition, profile, and capacity. The fluid acquisition was done by applying 5 ml of 0.9% saline solution to the sample then letting the fluid wick for 5 minutes. After 5 minutes, the rewet was taken for 2 minutes using standard laboratory filter paper. The products had the characteristics shown in Tables 41 and 42.

TABLE 41

| Product Profile | | Front | Front Middle | Back Middle | Back |
|---|---|---|---|---|---|
| Standard MR4 | Basis Wt. (g/m2) | 173 | 171 | 174 | 168 |
| | Density (g/cc) | 0.20 | 0.19 | 0.20 | 0.19 |
| | Caliper (cm) | 0.09 | 0.09 | 0.09 | 0.09 |
| Trial MR5 | Basis Wt. (g/m2) | 175 | 171 | 172 | 174 |
| | Density (g/cc) | 0.20 | 0.19 | 0.19 | 0.20 |
| | Caliper (cm) | 0.09 | 0.09 | 0.09 | 0.09 |
| Trial MR6 | Basis Wt. (g/m2) | 168 | 171 | 170 | 172 |
| | Density (g/cc) | 0.20 | 0.19 | 0.19 | 0.20 |
| | Caliper (cm) | 0.09 | 0.09 | 0.09 | 0.09 |
| Trial MR7 | Basis Wt. (g/m2) | 174 | 173 | 173 | 167 |
| | Density (g/cc) | 0.20 | 0.20 | 0.20 | 0.19 |
| | Caliper (cm) | 0.09 | 0.09 | 0.09 | 0.09 |
| Trial MR8 | Basis Wt. (g/m2) | 181 | 182 | 177 | 177 |
| | Density (g/cc) | 0.20 | 0.20 | 0.20 | 0.20 |
| | Caliper (cm) | 0.09 | 0.09 | 0.09 | 0.09 |

TABLE 42

| | Standard MR4 | Trial MR5 | Trial MR6 | Trial MR7 | Trial MR8 |
|---|---|---|---|---|---|
| \multicolumn{6}{l}{Product Properties} | | | | | |
| Product Wt. (g) | 3.51 | 3.53 | 3.51 | 3.55 | 3.56 |
| Core Weight (g) | 3.52 | 3.46 | 3.47 | 3.52 | 3.54 |
| Pulp Wt. (g) | 3.05 | 3.05 | 3.10 | 3.21 | 3.20 |
| SAP Wt. (g) | 0.48 | 0.46 | 0.39 | 0.34 | 0.34 |
| SAP/Core Ratio (%) | 13.5 | 13.1 | 11.2 | 9.5 | 9.5 |
| Basis Wt. (g/m²) | 174.2 Std. Dev. 5.8 | 172.8 Std. Dev. 4.0 | 173 Std. Dev. 3.9 | 179.6 Std. Dev. 4.4 | 172 Std. Dev. 2.5 |
| Density (g/cm³) | .203 Std. Dev. .009 | .195 Std. Dev. .006 | .193 Std. Dev. .007 | .210 Std. Dev. .004 | .204 Std. Dev. .003 |
| \multicolumn{6}{l}{Product Performance} | | | | | |
| Absorbent Capacity | 40.9 | 41.4 | 37.2 | 35.0 | 34.4 |
| Absorbent Capacity Index (g/g) | 11.6 | 12.0 | 10.7 | 9.9 | 9.7 |
| Retention Capacity | 29.4 | 27.6 | 26.1 | 24.7 | 25.2 |
| Retention Capacity Index (g/g) | 8.4 | 8.0 | 7.5 | 7.0 | 7.1 |
| \multicolumn{6}{l}{Rewet and Strike Thru} | | | | | |
| Primary Strike Thru (sec) | 16.4 | 21.2 | 18.4 | 16.4 | 16.7 |
| Primary Rewet (g) | 0.1 | 0.1 | 0.1 | 0.1 | 0.1 |
| Secondary Strike Thru (sec) | 24.4 | 23.1 | 24.5 | 22.6 | 29.1 |
| Secondary Rewet (g) | 0.5 | 0.5 | 0.5 | 0.5 | 0.4 |
| Tertiary Strike Thru (sec) | 14.0 | 14.2 | 15.4 | 13.2 | 14.8 |
| Tertiary Rewet (g) | 1.4 | 1.5 | 1.6 | 1.4 | 1.3 |

The synthetic urine wicking capability of the products was tested using ten 6.0 cm×16.0 cm samples and a 600 second pin read time. Tests were conducted by Materials Testing Service of Kalamazoo, Mich., using their own test equipment and procedures. The results are depicted in Tables 43 and 44 below.

TABLE 43

Average 45° Wicking Time In Seconds

| Product | Bottom Pin Wicking Time | Top Pin Wicking Time | Total Wicking Time |
|---|---|---|---|
| Standard MR4 | 199.90 | 600.00* | 600.00* |
| Trial MR5 | 141.53 | 600.00* | 600.00* |
| Trial MR6 | 144.64 | 600.00* | 600.00* |
| Trial MR7 | 169.48 | 600.00* | 600.00* |
| Trial MR8 | 163.71 | 600.00* | 600.00* |

*600 seconds was entered if the wicking did not reach the pin level

TABLE 44

| | Retention | | | Thickness | | | |
|---|---|---|---|---|---|---|---|
| Product | Wet Wt. (g) | Dry Wt. (g) | Amount Retained (g) | Beginning Thickness (mm) | End Thickness (mm) | Percent Change | Wicking Height (cm) |
| Standard MR4 | 11.59 | 1.66 | 9.93 | 0.70 | 2.36 | 236.9 | 10.3 |
| Trial MR5 | 11.76 | 1.65 | 10.10 | 0.74 | 1.99 | 169.2 | 10.8 |
| Trial MR6 | 10.74 | 1.59 | 9.14 | 0.70 | 1.94 | 176.7 | 10.6 |
| Trial MR7 | 10.06 | 1.68 | 8.38 | 0.81 | 2.04 | 154.7 | 10.0 |
| Trial MR8 | 10.46 | 1.61 | 8.85 | 0.83 | 2.11 | 153.9 | 10.2 |

Materials Testing Service tested the rewet of the products using ten 9.0 cm×20.3 cm sample cutouts, the dosing tube method, and one dose of 10 ml of 0.9% saline solution. The results are shown in Table 45.

TABLE 45

| Product | Dry Blotter (g) | Wet Blotter (g) | Rewet (g) |
|---|---|---|---|
| Standard MR4 | 7.67 | 8.29 | 0.61 |
| Trial MR5 | 7.87 | 8.60 | 0.72 |
| Trial MR6 | 7.35 | 8.13 | 0.78 |
| Trial MR7 | 7.84 | 8.79 | 0.95 |
| Trial MR8 | 7.68 | 8.48 | 0.80 |

Materials Testing Service tested the wet tensile strength for each product in the machine direction using ten samples, a gauge length of 5.00 cms, a sample width of 1.3 cms., a crosshead speed of 2.5 cm/min and a load cell of 30 kg. The results are shown in Table 46.

TABLE 46

| Product | Peak (kg) | Elongation (%) | TEA (JLS/M$^2$) |
|---|---|---|---|
| Standard MR4 | 0.243 | 15.78 | 16.268 |
| Trial MR5 | 0.266 | 16.67 | 19.247 |
| Trial MR6 | 0.259 | 18.20 | 19.900 |
| Trial MR7 | 0.336 | 20.62 | 28.268 |
| Trial MR8 | 0.342 | 20.78 | 28.799 |

Materials Testing Service tested the dry tensile strength and percent elongation for each product in the machine direction using ten samples, a gauge length of 5.00 cms, a sample width of 1.3 cms., a crosshead speed of 2.5 cm/min and a load cell of 30 kg. The results are shown in Table 47.

TABLE 47

| Product | Peak (kg) | Elongation (%) | TEA (JLS/M$^2$) |
|---|---|---|---|
| Standard MR4 | 1.009 | 7.56 | 34.807 |
| Trial MR5 | 1.009 | 7.89 | 34.585 |
| Trial MR6 | 0.898 | 8.59 | 33.700 |
| Trial MR7 | 1.144 | 9.60 | 48.128 |
| Trial MR8 | 1.091 | 9.56 | 46.308 |

Other Inventive Embodiments

Although the Applicants' presently desired inventions are defined in the attached claims, it is to be understood that the invention may also be defined in accordance with the following embodiments, which are not necessarily exclusive or limiting of those claimed:

A. A fiber derived from a bleached softwood or hardwood kraft pulp, in which the fiber has a 0.5% capillary CED viscosity of about 13 mPa·s or less, preferably less than about 10 mPa·s, more preferably less than 8 mPa·s, still more preferably less than about 5 mPa·s, or further still more preferably less than about 4 mPa·s.

B. A fiber derived from a bleached softwood kraft pulp, in which the fiber has an average fiber length of at least about 2 mm, preferably at least about 2.2 mm, for instance at least about 2.3 mm, or for example at least about 2.4 mm, or for example about 2.5 mm, more preferably from about 2 mm to about 3.7 mm, still more preferably from about 2.2 mm to about 3.7 mm.

C. A fiber derived from a bleached hardwood kraft pulp, in which the fiber has an average fiber length of at least about 0.75 mm, preferably at least about 0.85 mm, or at least about 0.95 mm, or more preferably at least about 1.15, or ranging from about 0.75 mm to about 1.25 mm.

D. A fiber derived from a bleached softwood kraft pulp, in which the fiber has a 0.5% capillary CED viscosity of about 13 mPa·s or less, an average fiber length of at least about 2 mm, and an ISO brightness ranging from about 85 to about 95.

E. A fiber according any of the embodiments A-D, in which the viscosity ranges from about 3.0 mPa·s to about 13 mPa·s, for example from about 4.5 mPa·s to about 13 mPa·s, preferably from about 7 mPa·s to about 13 mPa·s, or for example from about 3.0 mPa·s to about 7 mPa·s, preferably from about 3.0 mPa·s to about 5.5 mPa·s.

F. A fiber according to embodiments A-D, in which the viscosity is less than about 7 mPa·s.

G. A fiber according to embodiments A-D, in which the viscosity is at least about 3.5 mPa·s.

H. A fiber according to embodiments A-D, in which the viscosity is less than about 4.5 mPa·s.

I. A fiber according to embodiments A-D, in which the viscosity is at least about 5.5 mPa·s J. A fiber according to embodiment E, in which the viscosity is no more than about 6 mPa·s.

K. A fiber according to one of the embodiments above, in which the viscosity is less than about 13 mPa·s.

L. A fiber according to one of embodiments A-B and D-K, in which the average fiber length is at least about 2.2 mm.

M. A fiber according to one of embodiments A-B and D-L, in which the average fiber length is no more than about 3.7 mm.

N. A fiber according to one of embodiments A-M, in which the fiber has an S10 caustic solubility ranging from about 16% to about 30%, preferably from about 16% to about 20%.
O. A fiber according to one of embodiments A-M, in which the fiber has an S10 caustic solubility ranging from about 14% to about 16%.
P. A fiber according to one of embodiments A-O, in which the fiber has an S18 caustic solubility ranging from about 14% to about 22%, preferably from about 14% to about 18%, more preferably from about 14% to about 16%.
Q. A fiber according to one of embodiments A-P, in which the fiber has an S18 caustic solubility ranging from about 14% to about 16%.
R. A fiber according to one of embodiments A-Q, in which the fiber has a ΔR of about 2.9 or greater.
S. A fiber according to one of embodiments A-Q, in which the fiber has a ΔR or about 3.0 or greater, preferably about 6.0 or greater.
T. A fiber according to one of embodiments A-S, in which the fiber has a carboxyl content ranging from about 2 meq/100 g to about 8 meq/100 g, preferably from about 2 meq/100 g to about 6 meq/100 g, more preferably from about 3 meq/100 g to about 6 meq/100 g.
U. A fiber according to one of embodiments A-S, in which the fiber has a carboxyl content of at least about 2 meq/100 g.
V. A fiber according to one of embodiments A-S, in which the fiber has a carboxyl content of at least about 2.5 meq/100 g.
W. A fiber according to one of embodiments A-S, in which the fiber has a carboxyl content of at least about 3 meq/100 g.
X. A fiber according to one of embodiments A-S, in which the fiber has a carboxyl content of at least about 3.5 meq/100 g.
Y. A fiber according to one of embodiments A-S, in which the fiber has a carboxyl content of at least about 4 meq/100 g.
Z. A fiber according to one of embodiments A-S, in which the fiber has a carboxyl content of at least about 4.5 meq/100 g.
AA. A fiber according to one of embodiments A-S, in which the fiber has a carboxyl content of at least about 5 meq/100 g.
BB. A fiber according to one of embodiments A-S, in which the fiber has a carboxyl content of about 4 meq/100 g.
CC. A fiber according to one of embodiments A-BB, in which the fiber has an aldehyde content ranging from about 1 meq/100 g to about 9 meq/100 g, preferably from about 1 meq/100 g to about 3 meq/100 g.
DD. A fiber according to one of embodiments A-BB, in which the fiber has an aldehyde content of at least about 1.5 meq/100 g.
EE.
FF. A fiber according to one of embodiments A-BB, in which the fiber has an aldehyde content of at least about 2.0 meq/100 g.
GG. A fiber according to one of embodiments A-BB, in which the fiber has an aldehyde content of at least about 2.5 meq/100 g.
HH. A fiber according to one of embodiments A-BB, in which the fiber has an aldehyde content of at least about 3.0 meq/100 g.
II. A fiber according to one of embodiments A-BB, in which the fiber has an aldehyde content of at least about 3.5 meq/100 g.
JJ. A fiber according to one of embodiments A-BB, in which the fiber has an aldehyde content of at least about 4.0 meq/100 g.
KK. A fiber according to one of embodiments A-BB, in which the fiber has an aldehyde content of at least about 5.5 meq/100 g.
LL. A fiber according to one of embodiments A-BB, in which the fiber has an aldehyde content of at least about 5.0 meq/100 g.
MM. A fiber according to one of embodiments A-MM, in which the fiber has a carbonyl content as determined by copper number of greater than about 2, preferably greater than about 2.5, more preferably greater than about 3, or a carbonyl content as determined by copper number of from about 2.5 to about 5.5, preferably from about 3 to about 5.5, more preferably from about 3 to about 5.5, or the fiber has a carbonyl content as determined by copper number of from about 1 to about 4.
NN. A fiber according to one of embodiments A-NN, in which the carbonyl content ranges from about 2 to about 3.
OO. A fiber according to one of embodiments A-NN, in which the fiber has a carbonyl content as determined by copper number of about 3 or greater.
PP. A fiber according to one of embodiments A-NN, in which the fiber has a ratio of total carbonyl to aldehyde content ranging from about 0.9 to about 1.6.
QQ. A fiber according to one of embodiments A-NN, in which the ratio of total carbonyl to aldehyde content ranges from about 0.8 to about 1.0.
RR. A fiber according to one of the embodiments above, in which the fiber has a Canadian Standard Freeness ("freeness") of at least about 690 mls, preferably at least about 700 mls, more preferably at least about 710 mls, or for example at least about 720 mls or about 730 mls.
SS. A fiber according to one of the embodiments above, in which the fiber has a freeness of at least about 710 mls.
TT. A fiber according to one of the embodiments above, in which the fiber has a freeness of at least about 720 mls.
UU. A fiber according to any one of embodiments above, in which the fiber has a freeness of at least about 730 mls.
VV. A fiber according to one of the embodiments above, in which the fiber has a freeness of no more than about 760 mls.
WW. A fiber according to one of embodiments A-WW, in which the fiber has a fiber strength, as measured by wet zero span breaking length, ranging from about 4 km to about 10 km.
XX. A fiber according to one of embodiments A-WW, in which the fiber has a fiber strength ranging from about 5 km to about 8 km.
YY. A fiber according to one of embodiments A-WW, in which the fiber has a fiber strength, measured by wet zero span breaking length, of at least about 4 km.
ZZ. A fiber according to one of embodiments A-WW, in which the fiber has a fiber strength, measured by wet zero span breaking length, of at least about 5 km.

AAA. A fiber according to one of embodiments A-WW, in which the fiber has a fiber strength, measured by wet zero span breaking length, of at least about 6 km.
BBB. A fiber according to one of embodiments A-WW, in which the fiber has a fiber strength, measured by wet zero span breaking length, of at least about 7 km.
CCC. A fiber according to one of embodiments A-WW, in which the fiber has a fiber strength, measured by wet zero span breaking length, of at least about 8 km.
DDD. A fiber according to one of embodiments A-WW, in which the fiber has a fiber strength, measured by wet zero span breaking length, ranging from about 5 km to about 7 km.
EEE. A fiber according to one of embodiments A-WW, in which the fiber has a fiber strength, measured by wet zero span breaking length, ranging from about 6 km to about 7 km.
FFF. A fiber according to one of the embodiments above, in which the ISO brightness ranges from about 85 to about 92, preferably from about 86 to about 90, more preferably from about 87 to about 90 or from about 88 to about 90 ISO.
GGG. A fiber according to one of the embodiments above, in which the ISO brightness is at least about 85, preferably at least about 86, more preferably at least about 87, particularly at least about 88, more particularly at least about 89 or about 90 ISO.
HHH. A fiber according to one of embodiments A-FFF, in which the ISO brightness is at least about 87.
III. A fiber according to one of embodiments A-FFF, in which the ISO brightness is at least about 88.
JJJ. A fiber according to one of embodiments A-FFF, in which the ISO brightness is at least about 89.
KKK. A fiber according to one of embodiments A-FFF, in which the ISO brightness is at least about 90.
LLL. A fiber according to any of the embodiments above, wherein the fiber has about the same length as standard kraft fiber.
MMM. A fiber according to one of embodiments A-S and SS-MMM, having higher carboxyl content than standard kraft fiber.
NNN. A fiber according to one of embodiments A-S and SS-NNN, having higher aldehyde content than standard kraft fiber.
OOO. A fiber according to embodiments A-S and SS-MMM, having a ratio of total aldehyde to carboxyl content of greater than about 0.3, preferably greater than about 0.5, more preferably greater than about 1.4, or for example ranging from about 0.3 to about 0.5, or ranging from about 0.5 to about 1, or ranging from about 1 to about 1.5.
PPP. A fiber according to any of the embodiments above, having a higher kink index than standard kraft fiber, for example having a kink index ranging from about 1.3 to about 2.3, preferably from about 1.7 to about 2.3, more preferably from about 1.8 to about 2.3 or ranging from about 2.0 to about 2.3.
QQQ. A fiber according to any of the embodiments above, having a length weighted curl index ranging from about 0.11 to about 0.2, preferably from about 0.15 to about 0.2.
RRR. A fiber according to any of the embodiments above, having a lower crystallinity index than standard kraft fiber, for example a crystallinity index reduced from about 5% to about 20% relative to standard kraft fiber, preferably from about 10% to about 20%, more preferably reduced from 15% to 20% relative to standard kraft fiber.
SSS. A fiber according to any of the embodiments above, in which the R10 value ranges from about 65% to about 85%, preferably from about 70% to about 85%, more preferably from about 75% to about 85%.
TTT. A fiber according to any of the embodiments above, in which the R18 value ranges from about 75% to about 90%, preferably from about 80% to about 90%, more preferably from about 80% to about 87%.
UUU. A fiber according to any of the embodiments above, in which the fiber has odor control properties.
VVV. A fiber according to any of the embodiments above, in which the fiber reduces atmospheric ammonia concentration at least 40% more than standard kraft fiber, preferably at least about 50% more, more preferably at least about 60% more, in particular at least about 70% more, or at least about 75% more, more particularly at least about 80% more or about 90% more.
WWW. A fiber according to any of the embodiments above, in which the fiber absorbs from about 5 to about 10 ppm ammonia per gram of fiber, preferably from about 7 to about 10 ppm, more preferably from about 8 to about 10 ppm ammonia per gram of fiber.
XXX. A fiber according to any of the embodiments above, in which the fiber has an MEM Elution Cytotoxicity Test value of less than 2, preferably less than about 1.5, more preferably less than about 1.
YYY. A fiber according to any of the embodiments above, in which the copper number is less than 2, preferably less than 1.9, more preferably less than 1.8, still more preferably less than 1.7.
ZZZ. A fiber according to any of embodiments A-YYY having a kappa number ranging from about 0.1 to about 1, preferably from about 0.1 to about 0.9, more preferably from about 0.1 to about 0.8, for instance from about 0.1 to about 0.7 or from about 0.1 to about 0.6 or from about 0.1 to about 0.5, more preferably from about 0.2 to about 0.5.
AAAA. A fiber according to any of the embodiments above, having a hemicellulose content substantially the same as standard kraft fiber, for instance, ranging from about 16% to about 18% when the fiber is a softwood fiber or ranging from about 18% to about 25% when the fiber is a hardwood fiber.
BBBB. A fiber according to any of the embodiments above, in which the fiber exhibits antimicrobial and/or antiviral activity.
CCCC. A fiber according to any of embodiments B-C or L-CCCC, in which the DP ranges from about 350 to about 1860, for example from about 710 to about 1860, preferably from about 350 to about 910, or for example from about 1160 to about 1860.
DDDD. A fiber according to any of embodiments B-C or L-CCCC, in which the DP is less than about 1860, preferably less than about 1550, more preferably less than about 1300, still more preferably less than about 820, or less than about 600.
EEEE. A fiber according to any of the embodiments above, in which the fiber is more compressible and/or embossible than standard kraft fiber.
FFFF. A fiber according to embodiments A-OOO, in which the fiber may be compressed to a density of at least about 0.210 g/cc, preferably at least about 0.220 g/cc, more preferably at least about 0.230 g/cc, particularly at least about 0.240 g/cc.

GGGG. A fiber according to embodiments A-OOO, in which the fiber can be compressed to a density of at least about 8% higher than the density of standard kraft fiber, particularly ranging from about 8% to about 16% higher than the density of standard kraft fiber, preferably from about 8% to about 10%, or from about 12% to about 16% higher, more preferably from about 13% to about 16% higher, more preferably from about 14% to about 16% higher, in particular from about 15% to about 16% higher.

A number of embodiments have been described. Nevertheless, it will be understood that various modifications may be made without departing from the spirit and scope of the disclosure. Accordingly, other embodiments are within the scope of the following claims.

We claim:

1. A diaper, incontinence device, or other urine absorbing product comprising a modified kraft fiber produced by bleaching a cellulosic kraft pulp using a multi-stage bleaching process; and oxidizing the kraft pulp during at least one stage of the multi-stage bleaching process with a peroxide and a catalyst under acidic condition, wherein the multi-stage bleaching process comprises at least one bleaching stage following the oxidation stage, wherein the ISO brightness of the kraft pulp fiber at the end of the multi-stage bleaching process comprising the at least one oxidation stage is at least about 88, wherein the modified kraft fiber exhibits a hemicellulose content from about 16% to about 25%, an aldehyde content ranging from about 1 meq/100 g to about 9 meq/100 g, and a carboxyl content of at least about 3 meq/100 g, and wherein the kraft fiber does not comprise an optical brightening agent.

2. The urine absorbing product of claim 1 having improved urine wicking when compared to the same product made from fiber not subjected to the at least one oxidation stage.

3. The urine absorbing product of claim 2 having at least a 10% improvement in vertical wicking, horizontal wicking, or 45 degree wicking.

4. The urine absorbing product of claim 2 having at least a 15% improvement in vertical wicking, horizontal wicking, or 45 degree wicking.

5. The urine absorbing product of claim 2 having at least a 20% improvement in vertical wicking, horizontal wicking, or 45 degree wicking.

6. The urine absorbing product of claim 1 wherein the modified kraft fiber is further treated with a surface active agent.

7. The urine absorbing product of claim 1 wherein the product contains multiple layers of absorbent fiber, and wherein one or more of the layers comprises the modified kraft fiber.

8. The urine absorbing product of claim 7 wherein one or more of the layers comprises the modified kraft fiber, further treated with a surface active agent.

9. The urine absorbing product of claim 7 wherein at least two layers comprise the modified kraft fiber.

10. The urine absorbing product of claim 9 wherein at least one of the at least two layers comprises the modified kraft fiber, further treated with a surface active agent.

11. The urine absorbing product of claim 9 wherein at least two layers comprise the modified kraft fiber, further treated with a surface active agent.

12. The urine absorbing product of claim 7 having improved urine wicking when compared to the same product made from fiber not subjected to the at least one oxidation stage.

13. The urine absorbing product of claim 12 having at least a 10% improvement in vertical wicking, horizontal wicking, or 45 degree wicking.

14. The urine absorbing product of claim 12 having at least a 15% improvement in vertical wicking, horizontal wicking, or 45 degree wicking.

15. The urine absorbing product of claim 12 having at least a 20% improvement in vertical wicking, horizontal wicking, or 45 degree wicking.

16. The urine absorbing product of claim 1, wherein the ISO brightness is at least 89.

17. The urine absorbing product of claim 1, wherein the at least one catalyst is iron-containing, wherein the at least one peroxide is hydrogen peroxide, and wherein the pH of the at least one oxidation stage ranges from about 2 to about 6.

18. The urine absorbing product of claim 1, wherein the multi-stage bleaching process has no alkaline stage following the at least one oxidation stage.

19. The urine absorbing product of claim 1, wherein the multi-stage bleaching process comprises at least three successive acidic stages.

20. The urine absorbing product of claim 1, wherein the modified kraft fiber has a copper number greater than 2.

21. The urine absorbing product of claim 1, wherein the modified kraft fiber exhibits a hemicellulose content from about 16% to about 18%.

22. The urine absorbing product of claim 6, wherein the surface active agent is cationic.

23. The urine absorbing product of claim 22, wherein the cationic surface active agent is a fatty acid quaternary ammonium salt.

* * * * *